US008389533B2

(12) United States Patent
Connors et al.

(10) Patent No.: US 8,389,533 B2
(45) Date of Patent: Mar. 5, 2013

(54) GEM-DISUBSTITUTED AND SPIROCYCLIC AMINO PYRIDINES/PYRIMIDINES AS CELL CYCLE INHIBITORS

(75) Inventors: Richard V. Connors, Pacifica, CA (US); Kang Dai, Albany, CA (US); John Eksterowicz, San Francisco, CA (US); Pingchen Fan, Fremont, CA (US); Benjamin Fisher, San Mateo, CA (US); Jiasheng Fu, Foster City, CA (US); Kexue Li, Mountain View, CA (US); Zhihong Li, Millbrae, CA (US); Lawrence R. McGee, Pacifica, CA (US); Rajiv Sharma, Mumbai (IN); Xiaodong Wang, Millbrae, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/936,725

(22) PCT Filed: Apr. 6, 2009

(86) PCT No.: PCT/US2009/039678
§ 371 (c)(1),
(2), (4) Date: Dec. 1, 2010

(87) PCT Pub. No.: WO2009/126584
PCT Pub. Date: Oct. 15, 2009

(65) Prior Publication Data
US 2011/0097305 A1    Apr. 28, 2011

Related U.S. Application Data

(60) Provisional application No. 61/123,279, filed on Apr. 7, 2008.

(51) Int. Cl.
  *A01N 43/54*   (2006.01)
  *A61K 31/505*  (2006.01)
  *C07D 237/00*  (2006.01)
  *C07D 239/00*  (2006.01)
  *C07D 241/00*  (2006.01)

(52) U.S. Cl. ........................... 514/267; 544/230
(58) Field of Classification Search .................. None
See application file for complete search history.

(56) References Cited

U.S. PATENT DOCUMENTS

| | | | |
|---|---|---|---|
| 3,452,013 A | 6/1969 | Gladych et al. |
| 6,498,163 B1 | 12/2002 | Boschelli et al. |
| 6,627,637 B2 | 9/2003 | Ritzeler et al. |
| 7,026,313 B2 | 4/2006 | Repine |
| 7,208,489 B2 | 4/2007 | Barvian et al. |
| 7,452,887 B2 | 11/2008 | Dickson et al. |
| 2003/0203907 A1 | 10/2003 | Hayama et al. |
| 2004/0236084 A1 | 11/2004 | Biwersi et al. |
| 2005/0059670 A1 | 3/2005 | Beylin et al. |
| 2005/0137214 A1 | 6/2005 | Barvian et al. |
| 2005/0182078 A1 | 8/2005 | Barvian et al. |
| 2005/0222163 A1 | 10/2005 | Eck et al. |
| 2005/0272755 A1 | 12/2005 | Denis et al. |
| 2006/0047118 A1 | 3/2006 | Stadtmueller et al. |
| 2006/0074102 A1 | 4/2006 | Cusack et al. |
| 2006/0142312 A1 | 6/2006 | Flamme et al. |
| 2006/0194805 A1 | 8/2006 | Bakthavatchalam et al. |
| 2007/0004684 A1 | 1/2007 | Sennhenn et al. |
| 2007/0060566 A1 | 3/2007 | Bailey et al. |
| 2007/0072863 A1 | 3/2007 | Bennett et al. |
| 2007/0072882 A1 | 3/2007 | Guzi et al. |
| 2007/0082900 A1 | 4/2007 | Guzi et al. |
| 2007/0185143 A1 | 8/2007 | Traquandi et al. |
| 2007/0270362 A1 | 11/2007 | Harlan et al. |
| 2007/0281943 A1 | 12/2007 | Andrews et al. |
| 2007/0293558 A1 | 12/2007 | Gao et al. |
| 2008/0070914 A1 | 3/2008 | Freyne et al. |
| 2008/0125588 A1 | 5/2008 | Erdman et al. |
| 2008/0182853 A1 | 7/2008 | Kruman et al. |
| 2009/0030005 A1 | 1/2009 | Kamb et al. |
| 2009/0062318 A1 | 3/2009 | Gangjee |
| 2009/0082374 A1 | 3/2009 | Gangjee |
| 2009/0142337 A1 | 6/2009 | Squires |
| 2011/0142796 A1 | 6/2011 | Connors et al. |

FOREIGN PATENT DOCUMENTS

| | | |
|---|---|---|
| WO | WO 83/01446 | 4/1983 |
| WO | WO 01/38315 A1 | 5/2001 |
| WO | WO 01/70741 A1 | 9/2001 |
| WO | WO 01/72717 A1 | 10/2001 |
| WO | WO 02/02550 A1 | 1/2002 |
| WO | WO 02/076396 A2 | 10/2002 |
| WO | WO 03/062236 A1 | 7/2003 |
| WO | WO 03/080064 A | 10/2003 |
| WO | WO 2004/065378 A1 | 8/2004 |
| WO | WO 2005/077951 A2 | 8/2005 |
| WO | WO 2006/021547 A1 | 3/2006 |
| WO | WO 2006/042102 A2 | 4/2006 |
| WO | WO 2006/074985 A1 | 7/2006 |
| WO | WO 2006/077428 A1 | 7/2006 |
| WO | WO 2006/131552 A1 | 12/2006 |
| WO | WO 2007/024680 A1 | 3/2007 |
| WO | WO 2007/120752 A2 | 10/2007 |

(Continued)

OTHER PUBLICATIONS

Vippagunta et. al. Advanced Drug Delivery Reviews 48 (2001) 3-26.*
International Search Report for parent PCT Application No. PCT/US2009/039678, mailed on Aug. 18, 2009.
Written Opinion for parent PCT Application No. PCT/US2009/039678, dated Oct. 7, 2010.
International Preliminary Report on Patentability for parent PCT Application No. PCT/US2009/039678, dated Oct. 12, 2010.
Barbara, J-G et al., "Quantal release at a neuronal nicotinic synapse from rat adrenal gland," Proc. Natl. Acad. Science 93(18), 9905-9909 (1996).

(Continued)

*Primary Examiner* — Jeffrey Murray
(74) *Attorney, Agent, or Firm* — Bernard P. Friedrichsen

(57) ABSTRACT

Compounds, pharmaceutical compositions and methods are provided that are useful in the treatment of CDK4-mediated disorders, such as cancer. The subject compounds are gem-disubstituted or spirocyclic pyridine, pyrimidine and triazine derivatives.

20 Claims, No Drawings

FOREIGN PATENT DOCUMENTS

| | | |
|---|---|---|
| WO | WO 2007/125405 A2 | 11/2007 |
| WO | WO 2007/140222 A2 | 12/2007 |
| WO | WO 2008/001076 A1 | 1/2008 |
| WO | WO 2008/082490 A2 | 7/2008 |
| WO | WO 2008/115974 A2 | 9/2008 |
| WO | WO 2009/061345 A2 | 5/2009 |
| WO | WO 2009/061781 A1 | 5/2009 |
| WO | WO 2009/083780 A1 | 7/2009 |
| WO | WO 2009/085185 A1 | 7/2009 |
| WO | WO 2009/087225 A2 | 7/2009 |

OTHER PUBLICATIONS

Bathini, Y et al., "2-Aminoquinazoline Inhibitors of Cyclin-Dependent Kinases," Bioorg. Med. Chem. Lett., 15(17), pp. 3881-3885 (2005).

Baughn, L. B. et al., "A Novel Orally Active Small Molecule Potently Induces $G_1$ Arrest in Primary Myeloma Cells and Prevents Tumor Growth by Specific Inhibition of Cyclin-Dependent Kinase," Cancer Research 66(15), 7661-7667 (2006).

Brooks, E.E. et al., "CVT-313, a specific and Potent Inhibitor of CDK2 That Prevents Neointimal Proliferation", The Journal of Biological Chemistry 272(46), 29207-29211 (1997).

Bukanov, N.O. et al., "Long-lasting arrest of murine polycystic kidney disease with CDK inhibitor roscovitine", Nature 444(7121), 949-952 (2006).

Chang, M.W. et al., "Adenovirus-mediated Over-expression of the Cyclin/Cyclin-dependent Kinase Inhibitor, p21 Inhibits Vascular Smooth Muscle Cell Proliferation and Neointima Formation in the Rat Carotid Artery Model of Balloon Angioplasty", Journal of Clinical Investigation 96(5), 2260-2268 (1995).

Chen, X. et al., "Protection of Normal Proliferating Cells Against Chemotherapy by Staurosporine-Mediated, Selective, and Reversible $G_1$ Arrest", Journal of the National Cancer Institute 92(24), 1999-2008 (2000).

de Carcer, G. et al., "Targeting Cell Cycle Kinases for Cancer Therapy", Current Medicinal Chemistry 14(9), 969-985 (2007).

Fry, D. W. et al., "Specific inhibition of cyclin-dependent kinase 4/6 by PD 0332991 and associated antitumor activity in human tumor xenografts," Molecular Cancer Therapeutics 3(11), 1427-1438 (2004).

Gladych, J.M. Z et al. "Antiviral agents. 5H-as-Triazino[5,6-b]Indoles", Journal Medicinal Chemistry vol. 15(3), pp. 277-281 (1972).

Hassan, A.A. et al., "Novel Heterocyclics from 3-Substituted-5H-1,2,4-Triazino[5,6-b]indoles and Pi-Acceptors", Tetrahedron, vol. 50(33), pp. 9997-10010 (1994).

Kamb, A., "Cyclin-Dependent Kinase Inhibitors and Human Cancer", Current Topics in Microbiology and Immunology 227, 139-148 (1998).

Leach, A.G. et al., "Matched Molecular Pairs as a Guide in the Optimization of Pharmaceutical Properties; a Study of Aqueous Solubility, Plasma Protein Binding and Oral Exposure," Journal of Medicinal Chemistry 49(23), 6672-6682 (2006).

Lu, H. et al., "Toward Understanding the Structural Basis of Cyclin-Dependent Kinase 6 Specific Inhibition," Journal of Medicinal Chemistry 49(13), 3826-3831 (2006).

Malumbres, M. et al, "To Cycle or Not to Cycle: A Critical Decision in Cancer", Nature Rev Cancer 1, 222-231 (2001).

Mascarenhas, N.M. et al., "Combined Ligand and Structure Based Approaches for Narrowing on the Essential Physicochemical Characteristics for CDK4 Inhibition," Journal of Chemical Information and Modeling 48(7), 1325-1336 (2008).

Menu, E. et al., "A Novel Therapeutic Combination Using PD 0332991 and Bortezomib: Study in the 5T33MM Myeloma Model," Cancer Research 68(14), 5519-5523 (2008).

Menu, E. et al., "Correction on Combination Therapy Using PD 0332991 and Bortezomib," Cancer Research 69(5), 2149 (2009).

Mohammed, M.I., "Synthesis and antibacterial activity of some novel heterocycles," Bulgarian Chemical Communications 36(4), 241-248 (2004).

Morgan D.O., "Cyclin-Dependent Kinases: Engines, Clocks and Microprocessors," Annu. Rev. Cell. Dev. Biol. 13, 261-291 (1997).

Novak, M. et al., "Kinetics of Hydrolysis of 8-(Arylamino)-2'-deoxyguanosines," Journal of Organic Chemistry 67(7), 2303-2308 (2002).

Perry, B. et al., "Optimization of a series of multi-isoform PI3 kinase inhibitors," Bioorganic & Medicinal Chemistry Letters 18(19), 5299-5302 (2008).

Saab, R. et al., "Pharmacologic inhibition of cyclin-dependent kinase 4/6 activity arrests proliferation in myoblasts and rhabdomyosarcoma-derived cells," Molecular Cancer Therapeutics 5(5), 1299-1308 (2006).

Saris, C.P. et al., "Chemical properties of the ultimate metabolites of 2-amino-5-phenylpyridine (PHE-P-1) and its ortho-methyl derivative," Chemico-Biological Interactions 95(1,2), 29-40 (1995).

Schang, L.M. et al., "Requirement for cellular cyclin-dependent kinases in herpes simplex virus replication and transcription", Journal of Virology 72(7), 5626-5637 (1998).

Schmidt, M. et al., "Protection against chemotherapy-induced cytotoxicity by cyclin-dependent kinase inhibitors (CKI) in CKI-responsive cells compared with CKI-unresponsive cells," Oncogene 20(43), 6164-6171 (2001).

Taniguchi, K. et al., "Induction of the p16INK4a senescence gene as a new therapeutic strategy for the treatment of rheumatoid arthritis", Nature Medicine 5(7) 760-767 (1999).

Toogood, P.L. et al., "Discovery of a Potent and Selective Inhibitor of Cyclin-Dependent Kinase 4/6," Journal of Medicinal Chemistry 48(7), 2388-2406 (2005).

Vanderwel, et al., "Pyrido[2,3-d]pyrimidin-7-ones as Specific Inhibitors of Cyclin-Dependent Kinase 4," J. Med. Chem., 48(3), pp. 2371-2387 (2005).

Wang, L. et al., "Pharmacologic inhibition of CDK4/6: mechanistic evidence for selective activity or acquired resistance in acute myeloid leukemia," Blood 110(6), 2075-2083 (2007).

Wyatt, P. G. et al., "Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crystallography and Structure Based Drug Design," Journal of Medicinal Chemistry 51(16), 4986-4999 (2008).

Youssef, A. S. A. et al., "Synthesis of some heterocyclic systems of anticipated biological activities via 6-aryl-4-pyrazol-1-ylpyridazin-3-one," Canadian Journal of Chemistry 83(3), 251-259 (2005).

Youssef, A. S. A. et al., "Synthesis of some heterocyclic systems of anticipated biological activities via 6-aryl-4-pyrazol-1-ylpyridazin-3-one," Afinidad 61(514), 500-509 (2004).

Zhang, C. et al, "Advancing Bioluminescence Imaging Technology for the Evaluation of Anticancer Agents in the MDA-MB-435-HAL-Luc Mammary Fat Pad and Subrenal Capsule Tumor Models," Clinical Cancer Research 15(1), 238-246 (2009).

* cited by examiner

GEM-DISUBSTITUTED AND SPIROCYCLIC AMINO PYRIDINES/PYRIMIDINES AS CELL CYCLE INHIBITORS

This application is a national stage application under 35 U.S.C. §371 of International Application No. PCT/US2009/039678, having an international filing date of Apr. 6, 2009, which claims the benefit of, and priority to, U.S. Provisional Application No. 61/123,279, filed on Apr. 7, 2008.

FIELD OF THE INVENTION

This invention is in the field of pharmaceutical agents and specifically relates to compounds, compositions, uses and methods for treating cancer.

BACKGROUND OF THE INVENTION

Cyclin-dependent kinases (Cdks) are a family of serine/threonine protein kinases playing important cellular functions. The cyclins are the regulatory subunits that activate the catalytic Cdks. Cdk1/Cyclin B1, Cdk2/Cyclin A, Cdk2/Cyclin E, Cdk4/Cyclin D, Cdk6/Cyclin D are critical regulators of cell cycle progression. Cdks also regulate transcription, DNA repair, differentiation, senescence and apoptosis (Morgan D. O., *Annu. Rev. Cell. Dev. Biol.* 1997; 13:261-291).

Small molecule inhibitors of Cdks have been developed to treat cancer (de Career G et al., *Curr Med. Chem.* 2007; 14:969-85). Large amount of genetic evidence support that Cdks play critical roles in the development of most human cancers (Malumbres M et al, *Nature Rev Cancer,* 2001; 1:222-231). Genetic alterations in Cdks, their substrates or regulators have been shown to be associated with human cancer. Endogenous protein inhibitors of Cdks including p16, p21 and p27 inhibit Cdk activity and their overexpression result in cell cycle arrest and inhibition of tumor growth in preclinical models (Kamb A., *Curr. Top. Microbiolo. Immunol.,* 1998; 227:139-148).

Small molecule inhibitors of Cdks may also be used to treat variety of other diseases that result from aberrant cell proliferation, including cardiovascular disorders, renal diseases, certain infectious diseases and autoimmune diseases. Cell proliferation regulatory pathways including genes involved in the cell cycle G1 and S phase checkpoint (p53, pRb, p15, p16, and Cyclins A, D, E, Cdk 2 and Cdk4) have been associated with plaque progression, stenosis and restenosis after angioplasty. Over-expression of the Cdk inhibitor protein p21 has been shown to inhibit vascular smooth muscle proliferation and intimal hyperplasia following angioplasty (Chang M. W. et al., *J. Clin. Invest.,* 1995; 96:2260; Yang Z-Y. et al., *Proc. Natl. Acad. Sci.* (USA) 1996; 93:9905). A small molecule Cdk2 inhibitor CVT-313 (Ki=95 nM) was shown to cause in significant inhibition of neointima formation in animal models (Brooks E. E. et al., *J. Biol. Chem.* 1997; 272:29207-29211). Disregulation of cell cycle has been associated with polycystic kidney diseases, which are characterized by the growth of fluid-filled cysts in renal tubules. Treatment with small molecule inhibitors of Cdks yielded effective arrest of cystic disease in mouse models (Bukanov N. O., et al., *Nature,* 2006; 4444:949-952). Infection by a variety of infectious agents, including fungi, protozoan parasites such as *Plasmodium falciparum*, and DNA and RNA viruses may be treated with Cdk inhibitors. Cdks have been shown to be required for replication of herpes simplex virus (HSV) (Schang L. M. et al., *J. Virol.* 1998; 72:5626). Cdks are essential proteins in yeast. Synovial tissue hyperplasia plays important roles in the development of rheumatoid arthritis; inhibition of synovial tissue proliferation may suppress inflammation and prevent joint destruction. It has been shown that over-expression of Cdk inhibitor protein p16 inhibited synovial fibroblast growth (Taniguchi K. et al., *Nat. Med.* 1999; 5:760-767) and joint swelling was substantially inhibited in animal arthritis models.

Selective inhibitors of some Cdks may also be used to protect normal untransformed cells by inhibiting specific phases of cell cycle progression (Chen et al. *J. Natl. Cancer Institute,* 2000; 92:1999-2008). Pre-treatment with a selective Cdk inhibitor prior to the use of a cytotoxic agent that inhibits a different phase of the cell cycle may reduce the side effects associated with the cytotoxic chemotherapy and possibly increase the therapeutic widow. It has been shown that induction of cellular protein inhibitors of Cdks (p16, p27 and p21) conferred strong resistance to paclitaxel- or cisplatin-mediated cytotoxicity on the inhibitor-responsive cells but not on the inhibitor-unresponsive cells (Schmidt, M, *Oncogene,* 2001 20:6164-71).

DESCRIPTION OF THE INVENTION

A class of compounds useful in treating cancer is defined by the following Formula I or II

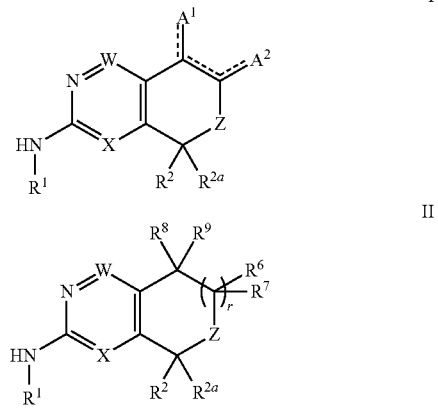

enantiomers, diastereomers, salts and solvates thereof wherein $A^1$ and $A^2$ together with ring carbon atoms to which they are attached combine to form benzene, cyclopentadiene, pyridine, pyridone, pyrimidine, pyrazine, pyridazine, 2H-pyran, pyrrole, imidazole, pyrazole, triazole, furan, oxazole, isoxazole, oxadiazole, thiophene, thiazole, isothiazole or thiadiazole any of which may be optionally partially saturated, and any of which may be optionally independently substituted with one or more $R^x$ groups as allowed by valence;

W and X are independently CH or N;

Z is absent, —O—, —S(O)$_n$—, or —NHR$^3$—;

$R^1$ is —Y—R$^a$ wherein

Y is alkyl, alkenyl, alkynyl, cycloalkyl, cycloalkenyl, heterocyclo, aryl or heteroaryl any of which may be optionally independently substituted with one or more R$^x$ groups as allowed by valence; and R$^a$ is heterocyclo, —NR$^3$R$^4$, —C(=O)NR$^3$R$^4$; —O—R$^5$, or —S(O)$_n$—R$^5$;

$R^2$ and $R^{2a}$ are each independently alkyl or alkenyl either of which may be optionally substituted with one or more R$^x$ as allowed by valance;

or $R^2$ and $R^{2a}$ together with the ring carbon atom to which they are attached combine to form a spiro-fused ring system of the following formula A

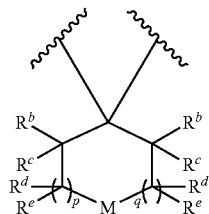

wherein
M is —$CR^dR^e$—, —O—, —$S(O)_n$—, or —$NHR^3$—;
$R^b$, $R^c$, $R^d$ and $R^e$ are each independently H or $R^x$, or alternatively $R^b$ and $R^d$ on adjacent carbon ring atoms may optionally combine to form a double bond as allowed by valance, and $R^d$ and $R^e$ on adjacent carbon ring atoms may optionally combine to form a double bond as allowed by valance;
$R^3$ and $R^4$ at each occurrence are independently
  (i) hydrogen or
  (ii) alkyl, cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance;
or $R^3$ and $R^4$ together with the nitrogen atom to which they are attached may combine to form a heterocyclo ring optionally independently substituted with one or more $R^x$ groups as allowed by valance;
$R^{3*}$ and $R^{4*}$ at each occurrence are independently
  (i) hydrogen or
  (ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance;
or $R^{3*}$ and $R^{4*}$ together with the nitrogen atom to which they are attached may combine to form a heterocyclo ring optionally independently substituted with one or more $R^x$ groups as allowed by valance;
$R^5$ and $R^{5*}$ at each occurrence is
  (i) hydrogen or
  (ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance;
$R^6$, $R^7$, $R^8$ and $R^9$ are each independently H or $R^x$, or alternatively
  (i) $R^6$ and $R^7$ together with the ring carbon atom to which they are attached may combine to form =O, =S or =$NR^3$, as allowed by valance;
  (ii) $R^8$ and $R^9$ together with the ring carbon atom to which they are attached may combine to form =O, =S or =$NR^3$, as allowed by valance;
  (iii) two $R^6$ groups on adjacent ring carbon atoms may combine to form a double bond as allowed by valance;
  (iv) $R^6$ and $R^8$ on adjacent ring carbon atoms may combine to form a double bond as allowed by valance;
$R^x$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-$OR^5$, -(alkylene)$_m$-$S(O)_nR^5$, -(alkylene)$_m$-$NR^3R^4$, -(alkylene)$_m$-C(=O)$R^5$, -(alkylene)$_m$-C(=S)$R^5$, -(alkylene)$_m$-C(=O)$OR^5$, -(alkylene)$_m$-OC(=O)$R^5$, -(alkylene)$_m$-C(=S)$OR^5$, -(alkylene)$_m$-C(=O)$NR^3R^4$, -(alkylene)$_m$-C(=S)$NR^3R^4$, -(alkylene)$_m$-N($R^3$)C(=O)$NR^3R^4$, -(alkylene)$_m$-N($R^3$)C(=S)$NR^3R^4$, -(alkylene)$_m$-N($R^3$)C(=O)$R^5$, -(alkylene)$_m$-N($R^3$)C(=S)$R^5$, -(alkylene)$_m$-OC(=O)$NR^3R^4$, -(alkylene)$_m$-OC(=S)$NR^3R^4$, -(alkylene)$_m$-$SO_2NR^3R^4$, -(alkylene)$_m$-N($R^3$)$SO_2R^5$, -(alkylene)$_m$-N($R^3$)$SO_2NR^3R^4$, -(alkylene)$_m$-N($R^3$)C(=O)$OR^5$, -(alkylene)$_m$-N($R^3$)C(=S)$OR^5$, or -(alkylene)$_m$-N($R^3$)$SO_2R^5$;
wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-$OR^{5*}$, -(alkylene)$_m$-$S(O)_nR^{5*}$, -(alkylene)$_m$-$NR^{3*}R^{4*}$, -(alkylene)$_m$-C(=O)$R^{5*}$, -(alkylene)$_m$-C(=S)$R^{5*}$, -(alkylene)$_m$-C(=O)$OR^{5*}$, -(alkylene)$_m$-OC(=O)$R^{5*}$, -(alkylene)$_m$-C(=S)$OR^{5*}$, -(alkylene)$_m$-C(=O)$NR^{3*}R^{4*}$, -(alkylene)$_m$-C(=S)$NR^{3*}R^{4*}$, -(alkylene)$_m$-N($R^{3*}$)C(=O)$NR^{3*}R^{4*}$, -(alkylene)$_m$-N($R^{3*}$)C(=S)$NR^{3*}R^{4*}$, -(alkylene)$_m$-N($R^{3*}$)C(=O)$R^{5*}$, -(alkylene)$_m$-N($R^{3*}$)C(=S)$R^{5*}$, -(alkylene)$_m$-OC(=O)$NR^{3*}R^{4*}$, -(alkylene)$_m$-OC(=S)$NR^{3*}R^{4*}$, -(alkylene)$_m$-$SO_2NR^{3*}R^{4*}$, -(alkylene)$_m$-N($R^{3*}$)$SO_2R^{5*}$, -(alkylene)$_m$-N($R^{3*}$)$SO_2NR^{3*}R^{4*}$, -(alkylene)$_m$-N($R^{3*}$)C(=O)$OR^{5*}$, -(alkylene)$_m$-N($R^{3*}$)C(=S)$OR^{5*}$, or -(alkylene)$_m$-N($R^{3*}$)$SO_2R^{5*}$;

n is 0, 1 or 2;
m is 0 or 1;
p and q are independently 0, 1 or 2; and
r is 1, 2 or 3 when Z is absent, or is 0, 1 or 2 when Z is present.

Compounds of this invention are selective inhibitors of cyclin dependent kinase Cdk4, which is to say that they inhibit Cdk4 with higher potency than they inhibit tyrosine kinases and other serine-threonine kinases including other cyclin-dependent kinases such as Cdk1. Cdk6 is structurally and functionally similar to Cdk4. Compounds of the present invention also inhibit Cdk6 at similar concentrations to those to inhibit Cdk4. Preferred embodiments of the present invention are compounds of the formula I inhibit Cdk4 at least about 100-fold more potently than they inhibit Cdk1.

The compounds of the present invention are useful for treating cancer including leukemia and solid cancer of the lung, breast, prostate, and skin such as melanoma, and other diseases with abnormal cell proliferation including but not limited to psoriasis, HSV, HIV, restenosis, and atherosclerosis.

Preferred compounds within the scope of Formula I include compounds wherein $A^1$ and $A^2$ together with the ring atoms to which they are attached combine to form

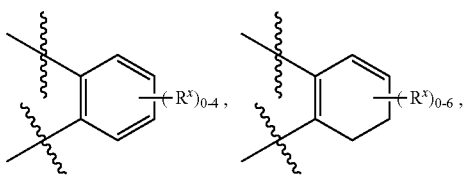

-continued

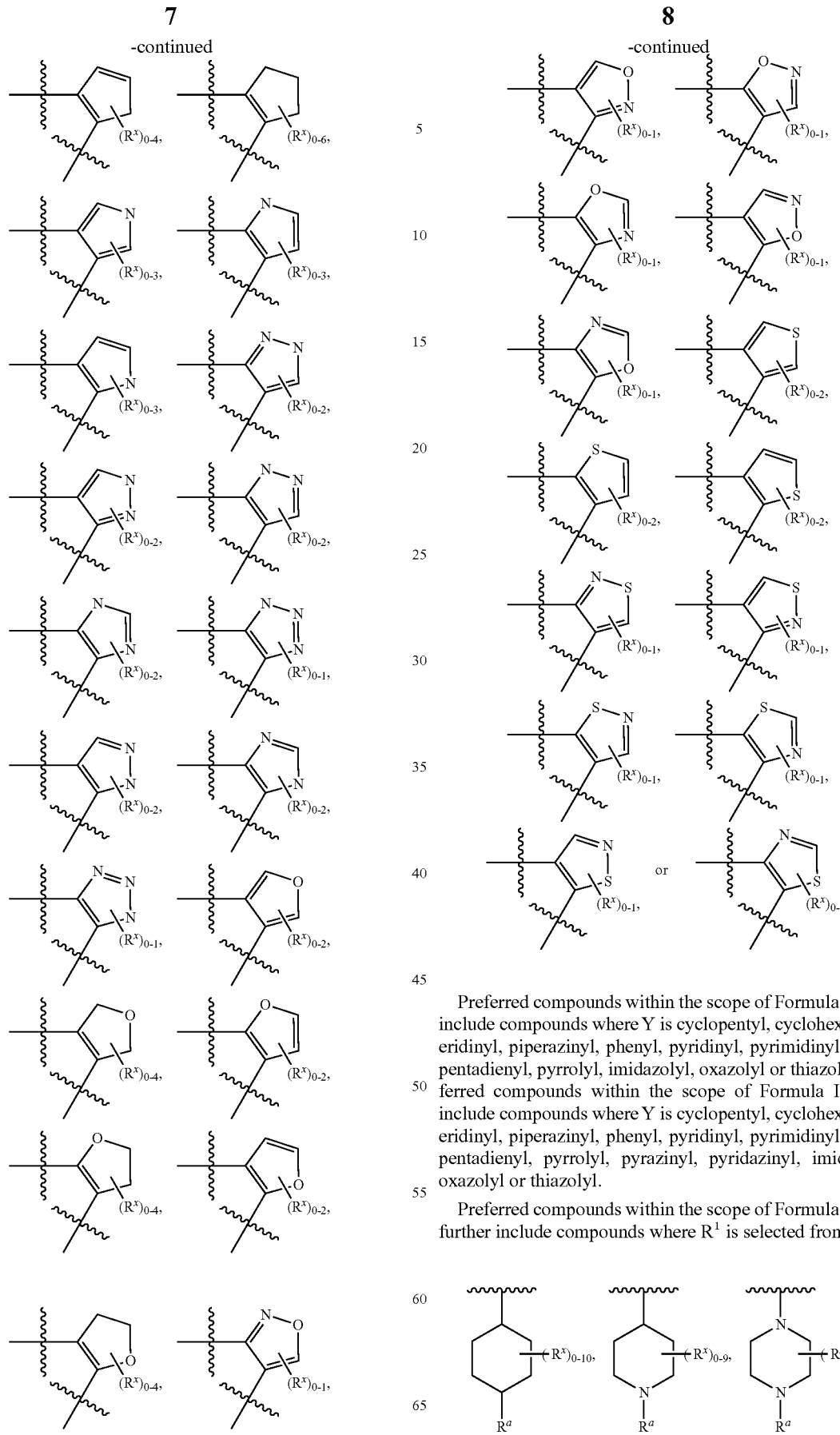

Preferred compounds within the scope of Formula I and II include compounds where Y is cyclopentyl, cyclohexyl, piperidinyl, piperazinyl, phenyl, pyridinyl, pyrimidinyl, cyclopentadienyl, pyrrolyl, imidazolyl, oxazolyl or thiazolyl. Preferred compounds within the scope of Formula I and II include compounds where Y is cyclopentyl, cyclohexyl, piperidinyl, piperazinyl, phenyl, pyridinyl, pyrimidinyl, cyclopentadienyl, pyrrolyl, pyrazinyl, pyridazinyl, imidazolyl, oxazolyl or thiazolyl.

Preferred compounds within the scope of Formula I and II further include compounds where $R^1$ is selected from

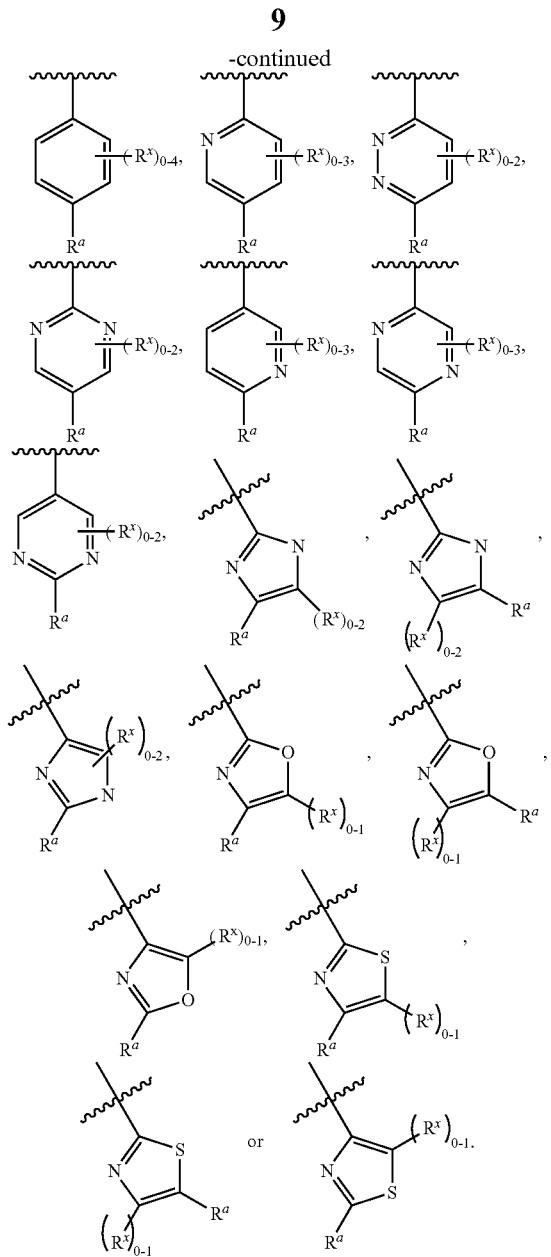

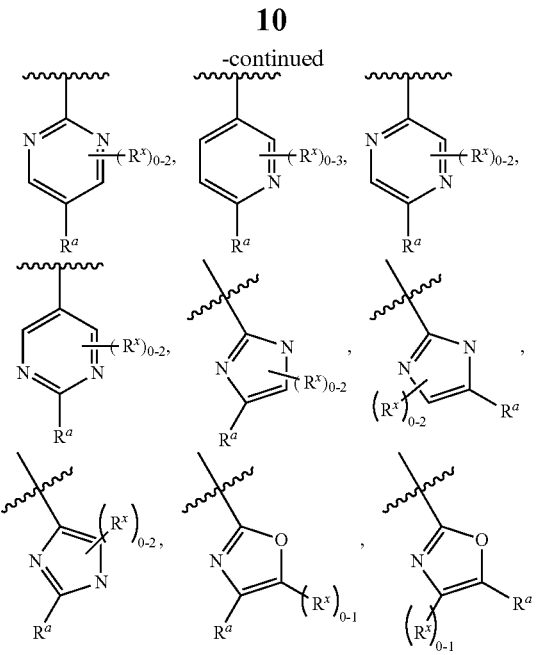

Preferred compounds within the scope of Formula I and II further include compounds where $R^1$ is selected from

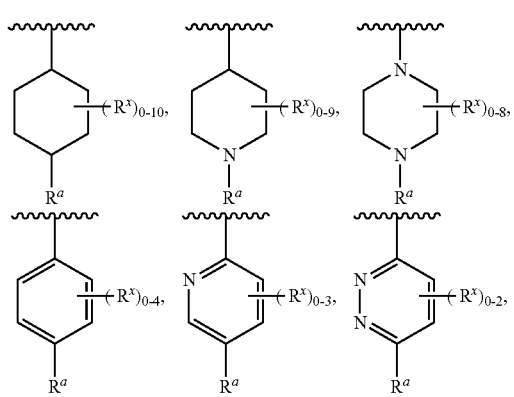

Preferred compounds within the scope of Formula I and II further include compounds where $R^1$ is selected from Preferred compounds within the scope of Formula I and II further include compounds where $R^a$ is selected from
(a) —$OR^5$ or —$S(O)_nR^5$ where $R^5$ is alkyl optionally independently substituted with one or more —$OR^{5*}$, or —$NR^{3*}R^{4*}$;
(b) —$C(=O)NR^3$, $R^4$ or —$NR^3R^4$ where $R^3$ and $R^4$ are independently alkyl optionally independently substituted with one or more —$OR^{5*}$, or —$NR^{3*}R^{4*}$;

or R³ and R⁴ together with the nitrogen atom to which they are attached combine to form

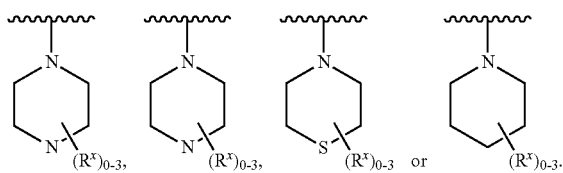

Preferred compounds within the scope of Formula I and II further include compounds where $R^2$ and $R^{2a}$ together with the ring carbon atom to which they are attached combine to form a spiro-fused ring system selected from

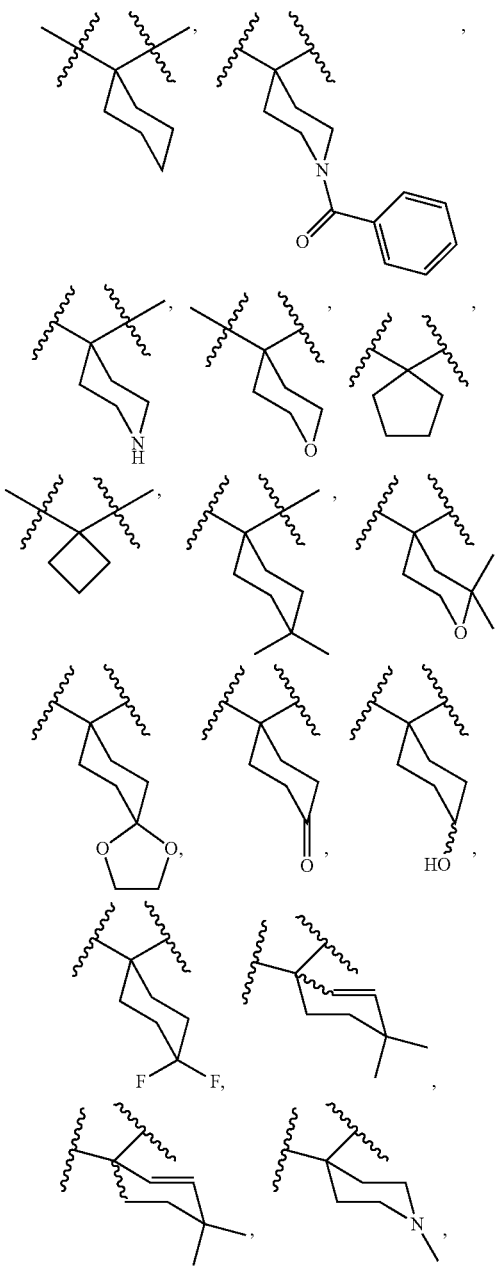

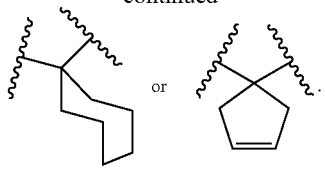

Preferred compounds within the scope of Formula I include compounds of the following formula IA

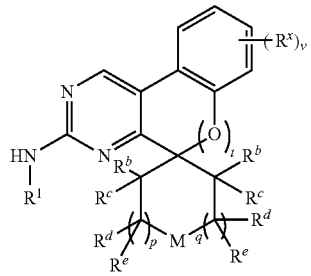

IA wherein t is 0 or 1; and v is 0, 1, 2, 3 or 4.

Preferred compounds within the scope of Formula IA include compounds having any of the preferred Y, $R^1$, $R^a$ and/or $R^2/R^{2a}$ substituents previously listed above.

Preferred compounds within the scope of Formula I include compounds having the following Formula IB

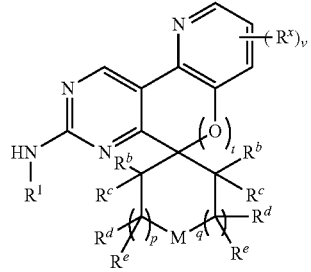

IB wherein t is 0 or 1; and v is 0, 1, 2, 3 or 4.

Preferred compounds within the scope of Formula IB include compounds having any of the preferred Y, $R^1$, $R^a$ and/or $R^2/R^{2a}$ substituents previously listed above. Preferred compounds within the scope of Formula IB include compounds where v is 0, 1 2 or 3.

Preferred compounds within the scope of Formula I include compounds having the following Formula IC

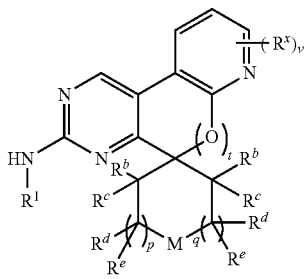

IC wherein t is 0 or 1; and v is 0, 1, 2, 3 or 4.

Preferred compounds within the scope of Formula IC include compounds having any of the preferred Y, $R^1$, $R^a$ and/or $R^2/R^{2a}$ substituents previously listed above. Preferred compounds within the scope of Formula IC include compounds where v is 0, 1 2 or 3.

Preferred compounds within the scope of Formula I include compounds having the following Formula ID

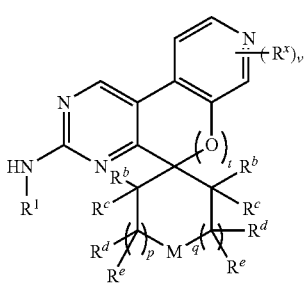

ID wherein t is 0 or 1; and v is 0, 1, 2, 3 or 4.

Preferred compounds within the scope of Formula ID include compounds having any of the preferred Y, $R^1$, $R^a$ and/or $R^2/R^{2a}$ substituents previously listed above. Preferred compounds within the scope of Formula ID include compounds where v is 0, 1 2 or 3.

Certain compounds within the scope of the present invention exist as keto-enol tautomers. For example compounds such as the following:

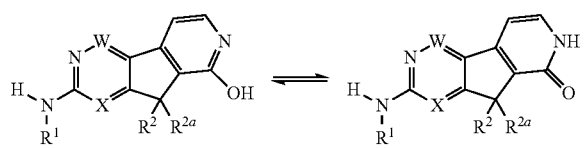

The current invention further provides a method of treating disorders or conditions consisting of abnormal cell proliferation, such as cancer, atherosclerosis, postsurgical vascular stenosis, restenosis, and endometriosis; infections, including viral infections such as DNA viruses like herpes and RNA viruses like HIV, and fungal infections; autoimmune diseases such as psoriasis, inflammation like rheumatoid arthritis, lupus, type 1 diabetes, diabetic nephropathy, multiple sclerosis, and glomerulonephritis, organ transplant rejection, including host versus graft disease, in a mammal, including human, comprising administering to said mammal an amount of a compound of formula I or II, or a pharmaceutically acceptable salt thereof, that is effective in treating such disorder or condition.

This invention further provides compounds of Formula I and II that are useful for treating abnormal cell proliferation such as cancer. The invention provides a method of treating a abnormal cell proliferation disorder such as myeloid disorders, lymphoid disorders, Hodgkin's hairy cells, leukemia, cancers of the breast, lung, colon, ovary, cervix, prostrate, testis, esophagus, stomach, skin, bone, pancreas, thyroid, biliary passages, buccal cavity and pharyns (oral), lip, tongue, mouth, pharynx, small intestine, colon-rectum, large intestine, rectum, brain and central nervous system, glioblastoma, neuroblastoma, keratocanthoma, epidermoid carcinoma, large cell carcinoma, adenocarcinoma, adenoma, adenocarcinoma, follicular carcinoma, undifferentiated carcinoma, papillary carcinoma, seminoma, melanoma, sarcoma, bladder carcinoma, liver carcinoma, and kidney carcinoma, comprising administering a therapeutically effective amount of a compound of formula I, or a pharmaceutically acceptable salt thereof, to a subject with one or more above disorders.

Embodiment of this invention is also a method of treating subjects with diseases caused by vascular smooth muscle cell proliferation. The method comprises administering to a subject with such a disorder an amount of a compound of formula I, or a pharmaceutically acceptable salt thereof.

This invention further provides a method of treating a subject suffering from gout comprising administering to said subject in need of treatment an amount of a compound of formula I, or a pharmaceutically acceptable salt thereof, sufficient to treat the condition.

The present invention further provides a method of treating a subject with kidney disease, such as polycystic kidney disease, comprising administering to said subject in need of treatment an amount of a compound of formula I and II, or a pharmaceutically acceptable salt thereof, sufficient to treat the condition.

Definitions

The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

The term "treatment" includes therapeutic treatment as well as prophylactic treatment (either preventing the onset of disorders altogether or delaying the onset of a pre-clinically evident stage of disorders in individuals).

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

Alkyl, alkylenyl, alkenyl, and alkynyl radicals may be optionally substituted with one or more functional groups such as halo, hydroxy, nitro, amino, cyano, haloalkyl, aryl, heteroaryl, heterocyclo and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 or more substituents such as lower alkyl, hydroxyl, halo, haloalkyl, nitro, cyano, alkoxy, lower alkylamino, and the like. Phenyl substituted with —O—$CH_2$—O— forms the aryl benzodioxolyl substituent.

The term "heterocyclyl" (or "heterocyclo") embraces saturated, and partially saturated and heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino, lower alkylamino, and the like.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl, dihydrothiazolyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydrobenzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term heterocyclyl, (or heterocyclo) also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydrobenzo[1,4]dioxinyl and dihydrobenzofuryl].

The term "heteroaryl" denotes aryl ring systems that contain one or more heteroatoms selected from the group O, N and S, wherein the ring nitrogen and sulfur atom(s) are optionally oxidized, and nitrogen atom(s) are optionally quarternized. Examples include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3, 4-thiadiazolyl, 1,2,5-thiadiazolyl].

The term "sulfonyl", whether used alone or linked to other terms such as alkylsulfonyl, denotes respectively divalent radicals —SO$_2$—.

The terms "sulfamyl," "aminosulfonyl" and "sulfonamidyl," denotes a sulfonyl radical substituted with an amine radical, forming a sulfonamide (—SO$_2$NH$_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, (CH$_3$S—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "aralkylamino" denotes amino groups, which have been substituted with one or two aralkyl radicals. More preferred are phenyl-C$_1$-C$_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups, which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Even more preferred are "5-6-membered cycloalkylalkyl" attached to alkyl portions having one to three carbon atoms. Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament.

The present invention comprises a pharmaceutical composition comprising a therapeutically effective amount of a compound of the current invention in association with a least one pharmaceutically acceptable carrier, adjuvant or diluent.

The present invention also comprises a method of treating angiogenesis related disorders in a subject having or susceptible to such disorder, the method comprising treating the subject with a therapeutically effective amount of a compound of the current invention.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of the current invention may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with compounds of the present invention, consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with compounds of the present invention, consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-H, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-AL esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan poly sulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with VEGFR inhibitors including N-(4-chlorophenyl)-4-(4-pyridinylmethyl)-1-phthalazinamine;

4-[4-[[[[4-chloro-3-(trifluoromethyl)phenyl]amino]carbonyl]amino]phenoxy]-N-methyl-2-pyridinecarboxamide;

N-[2-(diethylamino)ethyl]-5-[(5-fluoro-1,2-dihydro-2-oxo-3H-indol-3-ylidene)methyl]-2,4-dimethyl-1H-pyrrole-3-carboxamide;

3-[(4-bromo-2,6-difluorophenyl)methoxy]-5-[[[[4-(1-pyrrolidinyl)butyl]amino]carbonyl]amino]-4-isothiazolecarboxamide;

N-(4-bromo-2-fluorophenyl)-6-methoxy-7-[(1-methyl-4-piperidinyl)methoxy]-4-quinazolinamine;

3-[5,6,7,13-tetrahydro-9-[(1-methylethoxy)methyl]-5-oxo-12H-indeno[2,1-a]pyrrolo[3,4-c]carbazol-12-yl]propyl ester N,N-dimethyl-glycine;

N-[5-[[[5-(1,1-dimethylethyl)-2-oxazolyl]methyl]thio]-2-thiazolyl]-4-piperidinecarboxamide;

N-[3-chloro-4-[(3-fluorophenyl)methoxy]phenyl]-6-[5-[[[2-(methylsulfonyl)ethyl]amino]methyl]-2-furanyl]-4-quinazolinamine 4-[(4-Methyl-1-piperazinyl)methyl]-N-[4-methyl-3-[[4-(3-pyridinyl)-2-pyrimidinyl]amino]-phenyl]benzamide N-(3-chloro-4-fluorophenyl)-7-methoxy-6-[3-(4-morpholinyl)propoxy]-4-quinazolinamine N-(3-ethynylphenyl)-6,7-bis(2-methoxyethoxy)-4-quinazolinamine N-(3-(((((2R)-1-methyl-2-pyrrolidinyl)methyl)oxy)-5-(trifluoromethyl)phenyl)-2-((3-(1,3-oxazol-5-yl)phenyl)amino)-3-pyridinecarboxamide;

2-(((4-fluorophenyl)methyl)amino)-N-(3-(((((2R)-1-methyl-2-pyrrolidinyl)methyl)oxy)-5-(trifluoromethyl)phenyl)-3-pyridinecarboxamide;

N-[3-(Azetidin-3-ylmethoxy)-5-trifluoromethyl-phenyl]-2-(4-fluoro-benzylamino)-nicotinamide.

6-fluoro-N-(4-(1-methylethyl)phenyl)-2-(4-pyridinylmethyl)amino)-3-pyridinecarboxamide;

2-((4-pyridinylmethyl)amino)-N-(3-(((2S)-2-pyrrolidinylmethyl)oxy)-5-(trifluoromethyl)phenyl)-3-pyridinecarboxamide;

N-(3-(1,1-dimethylethyl)-1H-pyrazol-5-yl)-2-(4-pyridinylmethyl)amino)-3-pyridinecarboxamide;

N-(3,3-dimethyl-2,3-dihydro-1-benzofuran-6-yl)-2-((4-pyridinylmethyl)amino)-3-pyridinecarboxamide;

N-(3-((((2S)-1-methyl-2-pyrrolidinyl)methyl)oxy)-5-(trifluoromethyl)phenyl)-2-((4-pyridinylmethyl)amino)-3-pyridinecarboxamide;

2-((4-pyridinylmethyl)amino)-N-(3-((2-(1-pyrrolidinyl)ethyl)oxy)-4-(trifluoromethyl)phenyl)-3-pyridinecarboxamide;

N-(3,3-dimethyl-2,3-dihydro-1H-indol-6-yl)-2-(4-pyridinylmethyl)amino)-3-pyridinecarboxamide;

N-(4-(pentafluoroethyl)-3-(((2S)-2-pyrrolidinylmethyl)oxy)phenyl)-2-((4-pyridinylmethyl)amino)-3-pyridinecarboxamide;

N-(3-((3-azetidinylmethyl)oxy)-5-(trifluoromethyl)phenyl)-2-((4-pyridinylmethyl)amino)-3-pyridinecarboxamide;

N-(3-(4-piperidinyloxy)-5-(trifluoromethyl)phenyl)-2-((2-(3-pyridinyl)ethyl)amino)-3-pyridinecarboxamide;

N-(4,4-dimethyl-1,2,3,4-tetrahydro-isoquinolin-7-yl)-2-(1H-indazol-6-ylamino)-nicotinamide;

2-(1H-indazol-6-ylamino)-N-[3-(1-methylpyrrolidin-2-ylmethoxy)-5-trifluoromethyl-phenyl]-nicotinamide;

N-[1-(2-dimethylamino-acetyl)-3,3-dimethyl-2,3-dihydro-1H-indol-6-yl]-2-(1H-indazol-6-ylamino)-nicotinamide;

2-(1H-indazol-6-ylamino)-N-[3-(pyrrolidin-2-ylmethoxy)-5-trifluoromethyl-phenyl]-nicotinamide;

N-(1-acetyl-3,3-dimethyl-2,3-dihydro-1H-indol-6-yl)-2-(1H-indazol-6-ylamino)-nicotinamide;

N-(4,4-dimethyl-1-oxo-1,2,3,4-tetrahydro-isoquinolin-7-yl)-2-(1H-indazol-6-ylamino)-nicotinamide;

N-[4-(tert-butyl)-3-(3-piperidylpropyl)phenyl][2-(1H-indazol-6-ylamino)(3-pyridyl)]carboxamide;

N-[5-(tert-butyl)isoxazol-3-yl][2-(1H-indazol-6-ylamino)(3-pyridyl)]carboxamide; and N-[4-(tert-butyl)phenyl][2-(1H-indazol-6-ylamino)(3-pyridyl)]carboxamide.

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. No. 6,630,500, U.S. Pat. No. 6,515,004, U.S. Pat. No. 6,713,485, U.S. Pat. No. 5,521,184, U.S. Pat. No. 5,770,599, U.S. Pat. No. 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkin's lymphoma.

Exemplary anti-angiogenic agents include KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ERBITUX™ (IMC-C225), and VECTIBIX™ (panitumumab) IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents. The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-Met" as well as small molecules inhibitors of the c-Met kinase activity.

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); isrogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors (such as panitumumab), CDK inhibitors, TNF inhibitors, metallomatrix proteases inhibitors (MMP), COX-2 inhibitors including celecoxib, NSAID's, $\alpha_v\beta_3$ inhibitors, phosphatidylinitisol 3-kinase inhibitors, AKT/PCK inhibitors, proteasome inhibitors (such as Velcade™), Trail receptor agonists (such as AMG 655), Trail (such as AMG 951), XIAP inhibitors, BCl2 inhibitors, Aurora kinase inhibitors, Raf kinases inhibitors, ubiquitin ligase inhibitors, HGF inhibitors (such as AMG 102), and c-Met inhibitors (such as compounds described WO 06/116713 and U.S. Ser. No. 11/879,034).

Also included in the family of compounds of the current are the pharmaceutically acceptable salts and solvates thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the current invention may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of the current invention include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine All of these salts may be prepared by conventional means from the corresponding compound of the invention by reacting, for example, the appropriate acid or base with the compound of the current invention. When a basic group and an acid group are present in the same molecule, a compound of the current invention may also form internal salts.

Compounds of the current invention may be prepared by synthetic procedures reflected in the following examples, as well as other methods known to those of skill in the art. All LC-MS data were obtained using Agilent 1100 series LC/MSD, column: CAPCELL UG120 (3 um, 4.6 mm I.D.× 50 mm), solvent system: H$_2$O-MeCN with 0.1% formic acid. All preparative reverse HPLC separations were carried out using C-18 column, solvent system: MeCN/H$_2$O (each containing 0.1% TFA).

Example 1

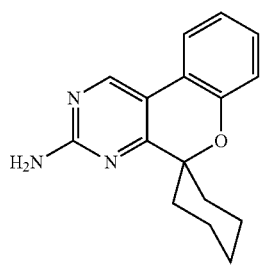

spiro[chromeno[3,4-d]pyrimidine-5,1'-cyclohexan]-3-amine

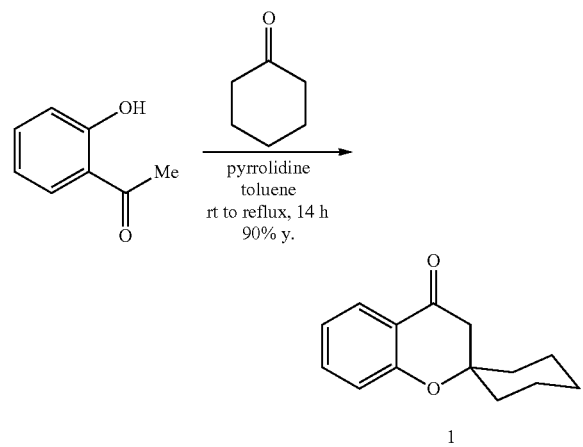

Spiro[chromene-2,1'-cyclohexan]-4(3H)-one (1) To a stirred mixture of 1-(2-hydroxyphenyl)ethanone (6.8 g, 50 mmol) and cyclohexanone (6.7 ml, 65 mmol) in toluene (25 mL) was added dropwise pyrrolidine (6.3 ml, 75 mmol) at rt. The resulting mixture was stirred at rt for 1.5 h and then refluxed for 12 h (equipped with Dean-Stark condensor). After cooling, the reaction mixture was poured into ice cold 2 N HCl aqueous solution, and extracted with EtOAc (2×). The combined organics were washed with 2 N NAOH aqueous solution (2×) followed by brine (1×), dried over Na$_2$SO$_4$, and concentrated in vacuo to give spiro[chromene-2,1'-cyclohexan]-4(3H)-one (1) (10 g, 92% yield) as a nearly colorless liquid. $^1$H NMR (400 MHz, CHLOROFORM-d) δ ppm 7.84 (1H, d, J=7.8 Hz), 7.47 (1H, t, J=7.6 Hz), 6.90-7.00 (2H, m), 2.71 (2H, s), 1.93-2.06 (2H, m), 1.59-1.78 (3H, m), 1.43-1.56 (4H, m), 1.27-1.40 (1H, m). LCMS-ESI (POS), M/Z, M+1: Found 217.1

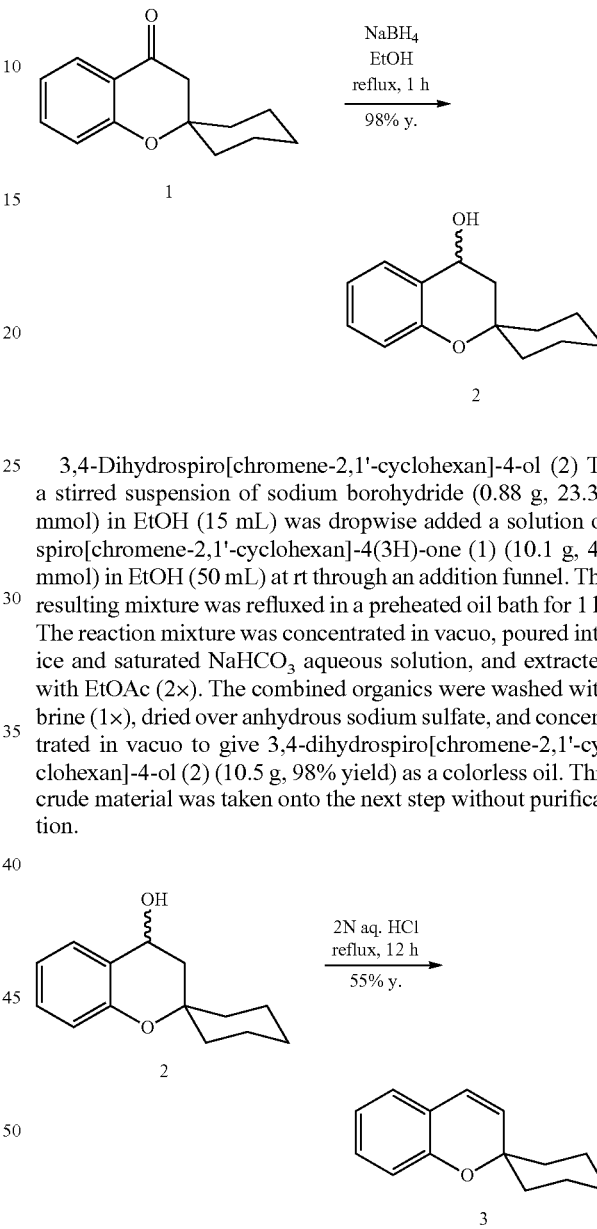

3,4-Dihydrospiro[chromene-2,1'-cyclohexan]-4-ol (2) To a stirred suspension of sodium borohydride (0.88 g, 23.35 mmol) in EtOH (15 mL) was dropwise added a solution of spiro[chromene-2,1'-cyclohexan]-4(3H)-one (1) (10.1 g, 47 mmol) in EtOH (50 mL) at rt through an addition funnel. The resulting mixture was refluxed in a preheated oil bath for 1 h. The reaction mixture was concentrated in vacuo, poured into ice and saturated NaHCO$_3$ aqueous solution, and extracted with EtOAc (2×). The combined organics were washed with brine (1×), dried over anhydrous sodium sulfate, and concentrated in vacuo to give 3,4-dihydrospiro[chromene-2,1'-cyclohexan]-4-ol (2) (10.5 g, 98% yield) as a colorless oil. This crude material was taken onto the next step without purification.

Spiro[chromene-2,1'-cyclohexane] (3) A mixture of crude 3,4-dihydrospiro[chromene-2,1'-cyclohexan]-4-ol (2) (10.4 g, 47 mmol) and 2 N hydrogen chloride (55 ml, 220 mmol) was heated at reflux for 12 h. The reaction mixture was then cooled to rt, poured into H$_2$O, and extracted with EtOAc (2×). (Note: the reaction wasn't complete when worked up.) The combined organics were washed with brine (1×), dried over Na$_2$SO$_4$ and concentrated in vacuo. The crude residue was subjected to combi-flash column chromatography (EtOAc/Hexanes) to give spiro[chromene-2,1'-cyclohexane] (3) (5.1 g, 55% yield) as a colorless crystalline solid. $^1$H NMR (400 MHz, DMSO-d$_6$) δ ppm 7.09 (1H, td, J=7.6, 1.6 Hz), 7.04

(1H, dd, J=7.4, 1.6 Hz), 6.83 (1H, td, J=7.4, 1.2 Hz), 6.76 (1H, d, J=8.2 Hz), 6.41 (1H, d, J=9.8 Hz), 5.76 (1H, d, J=9.8 Hz), 1.73-1.86 (2H, m), 1.40-1.71 (7H, m), 1.27-1.38 (1H, m). LCMS-ESI (POS), M/Z, M+1: Found 201.1

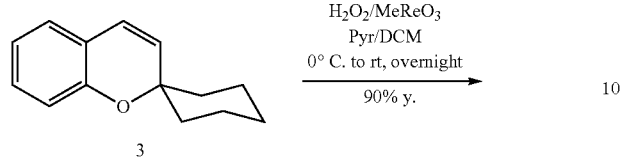

1a',7b'-Dihydrospiro[cyclohexane-1,2'-oxireno[c]chromene] (4) To a stirred ice-cooled solution of crude spiro[chromene-2,1'-cyclohexane] (3) (2.2 g, 11 mmol) and methyltrioxorhenium(vii) (0.055 g, 0.22 mmol) in DCM (30 mL) was added pyridine (0.21 ml, 2.6 mmol) followed by dropwise addition of 31.1% hydrogen peroxide (2.7 ml, 27 mmol) under nitrogen atmosphere. The resulting mixture was stirred at 0° C. for 10 min and at rt overnight. 2.2 mL of NaClO (commercial Clorox) was added dropwise at rt. The resulting mixture was stirred at rt for 1 h. Then the reaction mixture was poured into ice $H_2O$, and extracted with DCM (2×). The combined organics were washed with brine (1 X), dried over $Na_2SO_4$. Concentration in vacuo gave crude 1a',7b'-dihydrospiro[cyclohexane-1,2'-oxireno[c]chromene] (4) (2.3 g, 96% yield). This crude material was brought onto the next step without purification. $^1$H NMR (400 MHz, DMSO-$d_6$) δ ppm 7.44 (1H, dd, J=7.4, 1.6 Hz), 7.21-7.27 (1H, m), 6.92 (1H, td, J=7.4, 1.2 Hz), 6.79 (1H, d, J=7.8 Hz), 3.99 (1H, d, J=3.9 Hz), 3.66 (1H, d, J=4.3 Hz), 1.26-1.89 (10H, m). LCMS-ESI (POS), M/Z, M+1: Found 217.1

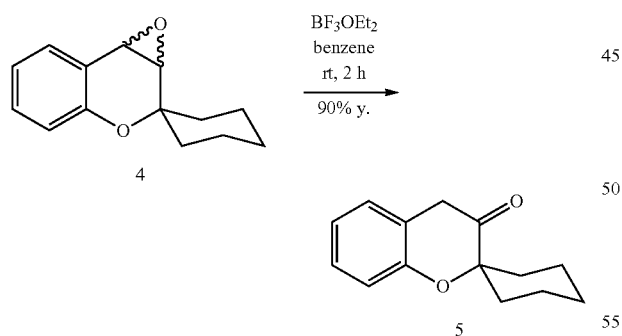

Spiro[chromene-2,1'-cyclohexan]-3(4H)-one (5) Boron trifluoride etherate (3.2 mL, 26 mmol) was added to a stirred solution of 1a',7b'-dihydrospiro[cyclohexane-1,2'-oxireno[c]chromene] (4) (2.3 g, 11 mmol) in benzene (100 mL) under a nitrogen atmosphere and maintained at rt for 2 h. Upon workup, the mixture was poured into ice and saturated $NaHCO_3$ aqueous solution and extracted with EtOAc (2×). The combined organics were washed with brine (1×), dried over $Na_2SO_4$, and concentrated in vacuo to give spiro[chromene-2,1'-cyclohexan]-3(4H)-one (5) (2.46 g, 98% yield), which was taken onto the next step without purification. LCMS-ESI (POS), M/Z, M+1: Found 217.1

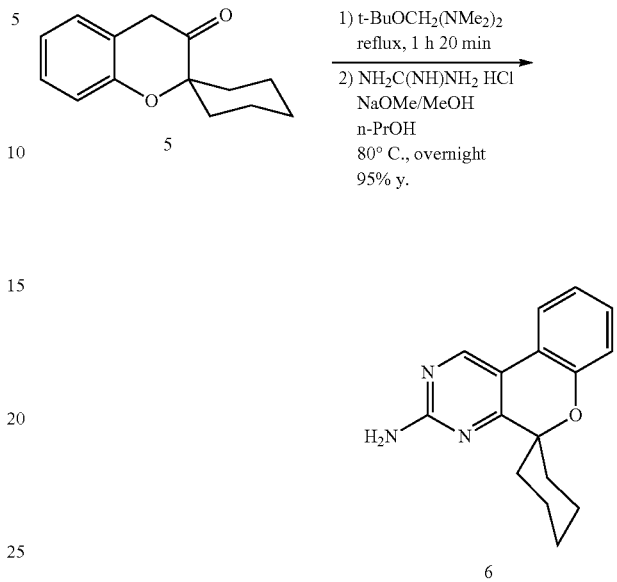

Spiro[chromeno[3,4-d]pyrimidine-5,1'-cyclohexan]-3-amine (6) A mixture of spiro[chromene-2,1'-cyclohexan]-3(4H)-one (5) (0.52 g, 2.41 mmol) and tert-butoxy-bis(dimethylamino)methane (0.75 ml, 3.61 mmol) was stirred at reflux for 80 min. The temperature was lowered to 80° C. and n-propanol (6 mL), guanidine hydrochloride (1.2 g, 12.0 mmol), and sodium methoxide in MeOH (4.37 M solution, 1.5 ml, 7.22 mmol) were added sequentially. The resulting mixture was stirred at 80° C. overnight, then poured into ice and saturated $NaHCO_3$ aqueous solution, and extracted with EtOAc (2×). The combined organics were washed with brine (1×), dried over $Na_2SO_4$ and concentrated in vacuo to give crude spiro[chromeno[3,4-d]pyrimidine-5,1'-cyclohexan]-3-amine (6) (0.67 g, 98% yield) as a orange solid. Trituration with EtOAc/Hexanes gave the pure spiro[chromeno[3,4-d]pyrimidine-5,1'-cyclohexan]-3-amine (6). $^1$H NMR (400 MHz, DMSO-$d_6$) δ ppm 8.75 (1H, s), 7.76 (1H, dd, J=7.8, 1.6 Hz), 7.17 (1H, td, J=7.6, 1.6 Hz), 6.94-7.04 (2H, m), 6.86 (2H, br. s.), 1.49-1.87 (9H, m), 1.20-1.30 (1H, m). LCMS-ESI (POS), M/Z, M+1: Found 268.1

Example 2

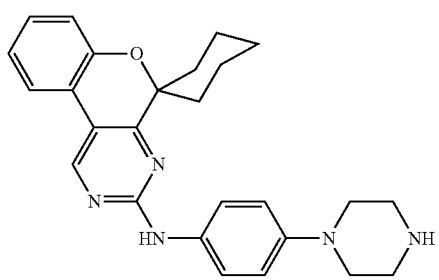

N-(4-(1-piperazinyl)phenyl)spiro[chromeno[3,4-d]pyrimidine-5,1'-cyclohexan]-3-amine

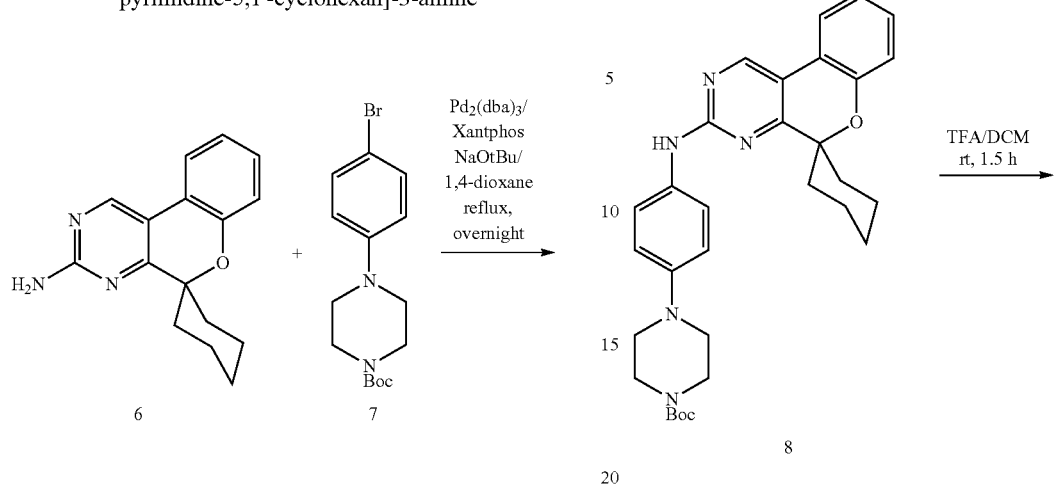

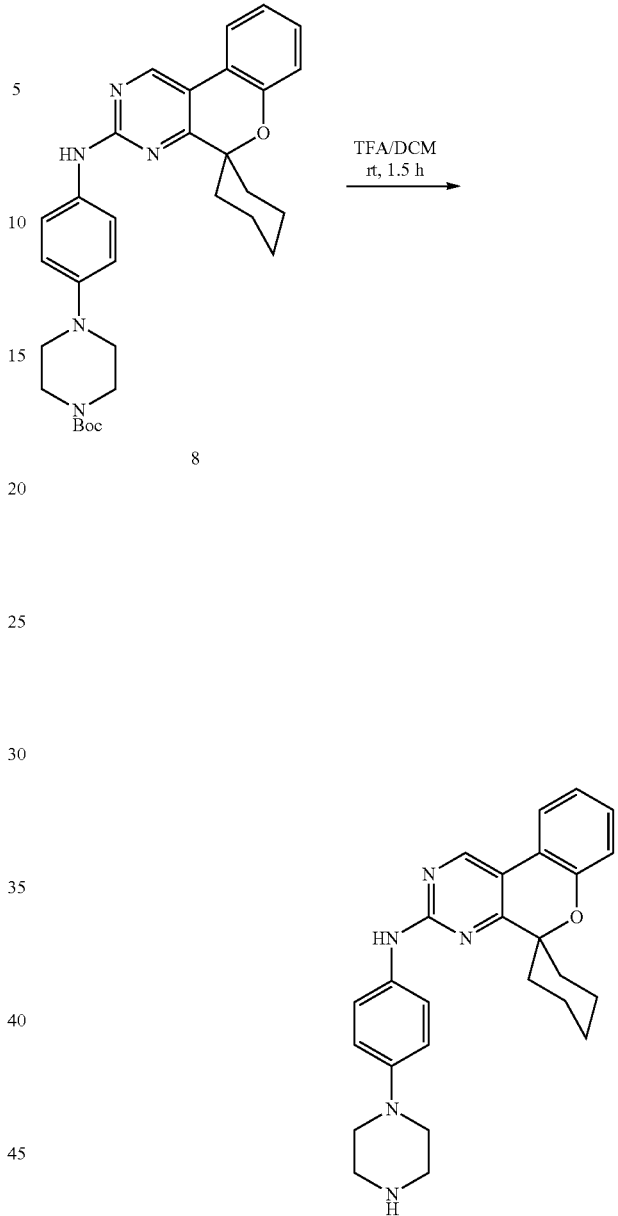

tert-Butyl 4-(4-(spiro[chromeno[3,4-d]pyrimidine-5,1'-cyclohexan]-3-ylamino)phenyl)-1-piperazinecarboxylate (8) A 10 mL single-necked RBF was charged sequentially with spiro[chromeno[3,4-d]pyrimidine-5,1'-cyclohexan]-3-amine (6) (0.29 g, 1.1 mmol), tert-butyl 4-(4-bromophenyl)piperazine-1-carboxylate (7) (0.37 g, 1.1 mmol), tris(dibenzylideneacetone)dipalladium (o) (0.012 g, 0.011 mmol), 9,9-dimethyl-4,5-bis(diphenylphosphino)xanthene (0.016 g, 0.023 mmol) (XantPhos) and sodium tert-butoxide (0.15 g, 1.52 mmol). The flask was then subjected to 3 cycles of evacuation and back-filling with $N_2$ before 1,4-dioxane (4 mL) was introduced through a syringe under $N_2$. The resulting mixture was then stirred at reflux overnight. The reaction was cooled and subjected to combi-flash column chromatography (EtOAc/Hexanes) to give tert-butyl-4-(4-(spiro[chromeno[3,4-d]pyrimidine-5,1'-cyclohexan]-3-ylamino)phenyl)-1-piperazinecarboxylate (8) (40 mg, 7% yield) as an off-white solid. LCMS-ESI (POS), M/Z, M+1: Found 528.3, Calculated 528.29.

N-(4-(1-piperazinyl)phenyl)spiro[chromeno[3,4-d]pyrimidine-5,1'-cyclohexan]-3-amine (9) TFA (1.0 ml, 13 mmol) was added dropwise to a stirred solution of tert-butyl 4-(4-(spiro[chromeno[3,4-d]pyrimidine-5,1'-cyclohexan]-3-ylamino)phenyl)-1-piperazinecarboxylate (8) (0.040 g, 0.075 mmol) in DCM (7 mL) and stirred at rt for 1.5 h. The volatiles were removed and the residue was dissolved in EtOAc and subsequently washed with ice cold 2 N NaOH aqueous solution (2×). The organic was dried over $Na_2SO_4$ and the residue after concentration in vacuo was triturated with EtOAc/Hexanes to pure N-(4-(1-piperazinyl)phenyl)spiro[chromeno[3,4-d]pyrimidine-5,1'-cyclohexan]-3-amine (9) (0.025 g, 80% yield) as a light yellow solid. $^1$H NMR (400 MHz, DMSO-$d_6$) δ ppm 9.56 (1H, br. s.), 8.93 (1H, s), 7.83 (1H, dd, J=7.8, 1.2 Hz), 7.60 (2H, d, J=9.4 Hz), 7.22 (1H, td, J=7.6, 1.6 Hz), 6.98-7.08 (2H, m), 6.89 (2H, d, J=9.4 Hz), 2.94-3.02 (4H, m), 2.77-2.87 (4H, m), 1.52-1.96 (9H, m), 1.21-1.34 (1H, m).
LCMS-ESI (POS), M/Z, M+1: Found 428.2
Example 3
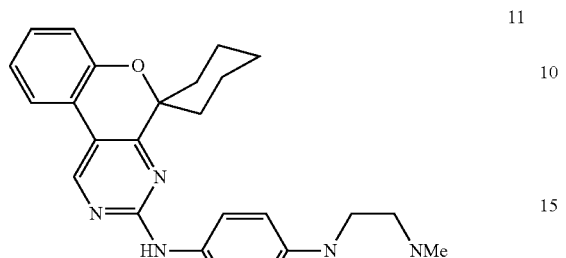
N-(4-(4-methyl-1-piperazinyl)phenyl)spiro[chromeno[3,4-d]pyrimidine-5,1'-cyclohexan]-3-amine
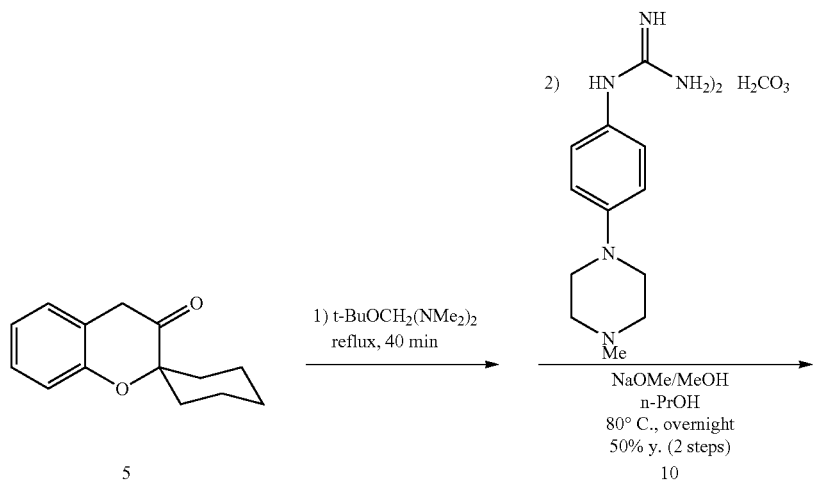
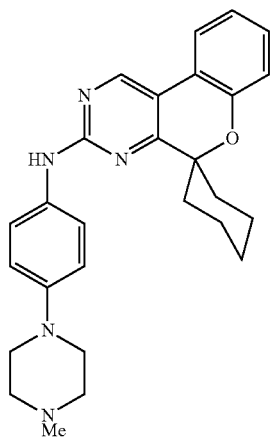

Title compound (II) was prepared using chemistry similar to that described in Example 1 except that guanidine hydrochloride was replaced by the corresponding aryl guanidine [J. Med. Chem., 1993, Vol. 36, No. 19., pg 2716] as its carbonate. $^1$H NMR (400 MHz, DMSO-d$_6$) δ ppm 9.57 (1H, br. s.), 8.93 (1H, s), 7.83 (1H, dd, J=7.8, 1.6 Hz), 7.60 (2H, d, J=9.0 Hz), 7.22 (1H, td, J=7.8, 1.6 Hz), 6.99-7.08 (2H, m), 6.91 (2H, d, J=9.0 Hz), 3.00-3.14 (4H, m), 2.42-2.48 (4H, m), 2.22 (3H, s), 1.55-1.95 (9H, m), 1.26-1.34 (1H, m). LCMS-ESI (POS), M/Z, M+1: Found 442.1.

Example 4

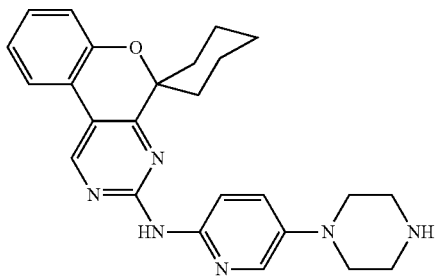

12

N-(5-(1-piperazinyl)-2-pyridinyl)spiro[chromeno[3,4-d]pyrimidine-5,1'-cyclohexan]-3-amine Title compound 12 was prepared from compound 6 using chemistry similar to that described in Example 2. $^1$H NMR (500 MHz, DMSO-d$_6$) δ ppm 10.60 (1H, br. s.), 9.07 (1H, s), 8.89 (2H, br. s.), 8.07 (1H, d, J=2.4 Hz), 7.96 (1H, d, J=9.2 Hz), 7.93 (1H, d, J=7.9 Hz), 7.81 (1H, dd, J=9.5, 2.7 Hz), 7.30 (1H, t, J=7.9 Hz), 7.10 (1H, t, J=7.6 Hz), 7.07 (1H, d, J=7.9 Hz), 3.35-3.47 (4H, m), 3.23-3.34 (4H, m), 1.84-2.03 (4H, m), 1.70-1.83 (3H, m), 1.58-1.69 (2H, m), 1.25-1.42 (1H, m); LCMS-ESI (POS), M/Z, M+1: Found 429.2

Example 5

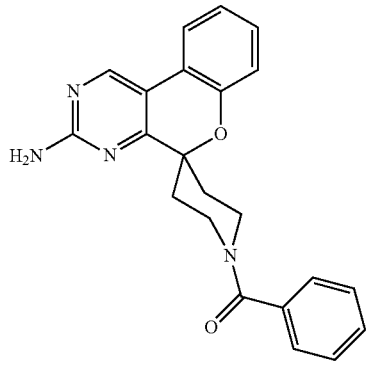

13

1'-(phenylcarbonyl)spiro[chromeno[3,4-d]pyrimidine-5,4'-piperidin]-3-amine

Title compound 13 was prepared using chemistry similar to that described in Example 1. $^1$H NMR (400 MHz, DMSO-d$_6$) δ ppm 8.81 (1H, s), 7.79 (1H, dd, J=7.6, 1.4 Hz), 7.37-7.52 (5H, m), 7.17-7.23 (1H, m), 7.01-7.09 (2H, m), 6.97 (2H, br. s.), 4.27-4.45 (2H, m), 3.50-3.59 (2H, m), 1.98-2.08 (4H, m). LCMS-ESI (POS), M/Z, M+1: Found 373.1

Example 6

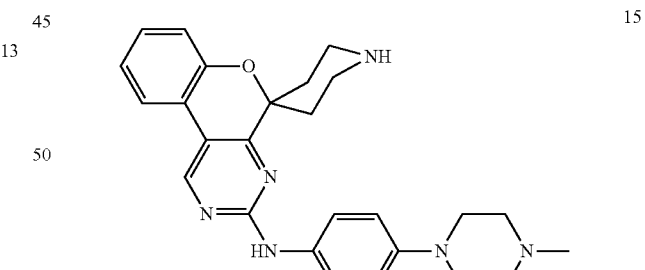

14

N-(4-(4-methyl-1-piperazinyl)phenyl)-1'-(phenylcarbonyl)spiro[chromeno[3,4-d]pyrimidine-5,4'-piperidin]-3-amine Title compound (14) was prepared using chemistry similar to that described in Example 3. Retention time on reverse phase analytical HPLC: 7.462 min LCMS-ESI (POS), M/Z, M+1: Found 547.2

Example 7

15

N-(4-(4-methyl-1-piperazinyl)phenyl)spiro[chromeno[3,4-d]pyrimidine-5,4'-piperidin]-3-amine Title compound 15 was obtained alongside compound (14) (Example 6) by in situ deprotection under the reaction conditions and then purified by chromatography. $^1$H NMR (400 MHz, DMSO-d$_6$) δ ppm 9.66 (1H, br. s.), 8.98 (1H, s), 8.25 (1H, s), 7.86 (1H, d, J=7.8 Hz), 7.60 (2H, d, J=9.0 Hz), 7.21-7.29 (1H, m), 7.03-7.12 (2H, m), 6.91 (2H, d, J=9.0 Hz), 3.00-3.18 (8H, m), 2.41-2.48 (4H, m), 2.11-2.28 (5H, m), 1.94 (2H, d, J=13.3 Hz). LCMS-ESI (POS), M/Z, M+1: Found 443.2

Example 8

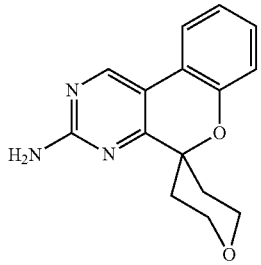

16

2',3',5',6'-tetrahydrospiro[chromeno[3,4-d]pyrimidine-5,4'-pyran]-3-amine

Title compound (16) was prepared using chemistry similar to that described in Example 1. $^1$H NMR (400 MHz, DMSO-$d_6$) δ ppm 8.79 (1H, s), 7.78 (1H, dd, J=8.2, 1.6 Hz), 7.16-7.23 (1H, m), 6.99-7.07 (2H, m), 6.94 (2H, br. s.), 3.72-3.83 (4H, m), 2.04-2.17 (2H, m), 1.65-1.77 (2H, m). LCMS-ESI (POS), M/Z, M+1: Found 270.1

Example 9

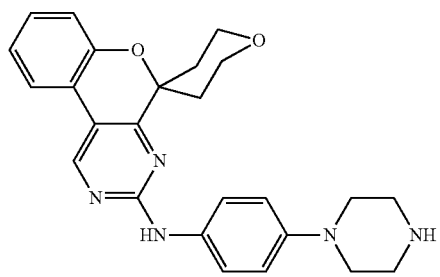

17

N-(4-(1-piperazinyl)phenyl)-2',3',5',6'-tetrahydrospiro[chromeno[3,4-d]pyrimidine-5,4'-pyran]-3-amine Title compound (17) was prepared from compound (16) using chemistry similar to that described in Example 2. $^1$H NMR (400 MHz, DMSO-$d_6$) δ ppm 9.63 (1H, br. s.), 8.97 (1H, s), 7.85 (1H, dd, J=7.6, 1.4 Hz), 7.59 (2H, d, J=9.0 Hz), 7.19-7.27 (1H, m), 7.01-7.12 (2H, m), 6.90 (2H, d, J=9.4 Hz), 3.74-3.90 (4H, m), 2.93-3.05 (4H, m), 2.77-2.87 (4H, m), 2.10-2.24 (2H, m), 1.80 (2H, d, J=12.9 Hz). LCMS-ESI (POS), M/Z, M+1: Found 430.1

Example 10

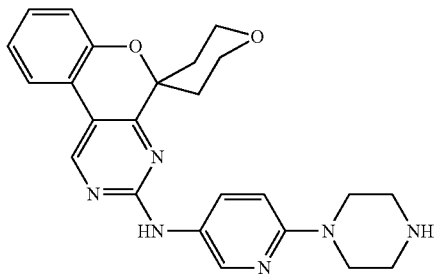

18

N-(6-(1-piperazinyl)-3-pyridinyl)-2',3',5',6'-tetrahydrospiro[chromeno[3,4-d]pyrimidine-5,4'-pyran]-3-amine Title compound (18) was prepared from compound (16) using chemistry similar to that described in Example 2. $^1$H NMR (500 MHz, DMSO-$d_6$) δ ppm 9.80 (1H, s), 9.01 (1H, s), 8.81 (2H, br. s.), 8.59 (1H, d, J=2.4 Hz), 8.01 (1H, dd, J=9.3, 2.7 Hz), 7.88 (1H, dd, J=7.7, 1.3 Hz), 7.23-7.30 (1H, m), 7.07-7.13 (2H, m), 7.05 (1H, d, J=9.3 Hz), 3.80-3.86 (4H, m), 3.65-3.72 (4H, m), 3.17-3.31 (4H, m), 2.10-2.23 (2H, m), 1.82 (2H, d, J=12.7 Hz); LCMS-ESI (POS), M/Z, M+1: Found 431.2

Example 11

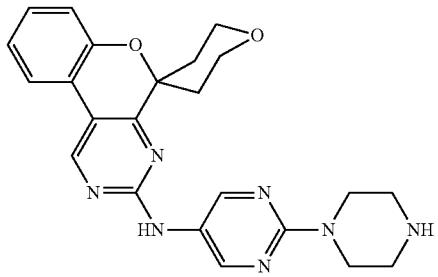

19

N-(2-(1-piperazinyl)-5-pyrimidinyl)-2',3',5',6'-tetrahydrospiro[chromeno[3,4-d]pyrimidine-5,4'-pyran]-3-amine Title compound (19) was prepared from compound (16) using chemistry similar to that described in Example 2. $^1$H NMR (500 MHz, DMSO-$d_6$) δ ppm 9.74 (1H, s), 9.00 (1H, s), 8.81 (2H, br. s.), 8.77 (2H, s), 7.87 (1H, dd, J=7.6, 1.2 Hz), 7.22-7.29 (1H, m), 7.05-7.11 (2H, m), 3.88-3.94 (4H, m), 3.78-3.84 (4H, m), 3.15-3.24 (4H, m), 2.07-2.19 (2H, m), 1.76-1.84 (5H, m)); LCMS-ESI (POS), M/Z, M+1: Found 432.2.

Example 12

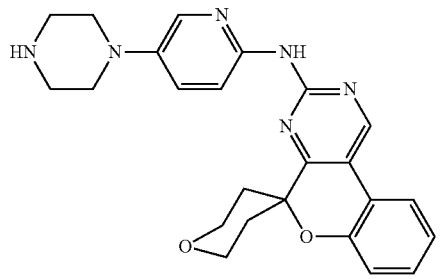

N-(5-(1-piperazinyl)-2-pyridinyl)-2',3',5',6'-tetrahydrospiro[chromeno[3,4-d]pyrimidine-5,4'-pyran]-3-amine Title compound (20) was prepared from compound (16) using chemistry similar to that described in Example 2. $^1$H NMR (400 MHz, DMSO-d$_6$) δ ppm 9.77 (1H, s), 9.03 (1H, s), 8.04 (1H, d, J=9.0 Hz), 8.00 (1H, d, J=3.1 Hz), 7.89 (1H, d, J=7.8 Hz), 7.45 (1H, dd, J=9.0, 3.1 Hz), 7.23-7.30 (1H, m), 7.04-7.12 (2H, m), 3.83 (4H, d, J=7.8 Hz), 2.96-3.11 (4H, m), 2.76-2.89 (4H, m), 2.10-2.25 (2H, m), 1.81 (2H, d, J=12.9 Hz). LCMS-ESI (POS), M/Z, M+1: Found 431.2.

Example 13

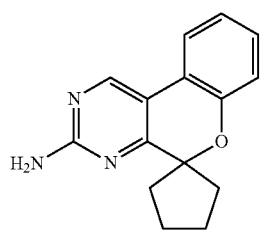

spiro[chromeno[3,4-d]pyrimidine-5,1'-cyclopentan]-3-amine

Title compound (21) was prepared using chemistry similar to that described in Example 1. $^1$H NMR (400 MHz, DMSO-d$_6$) δ ppm 8.75 (1H, s), 7.76 (1H, dd, J=7.8, 1.6 Hz), 7.15 (1H, td, J=7.6, 1.6 Hz), 7.00 (1H, td, J=7.4, 1.2 Hz), 6.84-6.93 (3H, m), 2.05-2.18 (2H, m), 1.68-2.01 (6H, m). LCMS-ESI (POS), M/Z, M+1: Found 254.1.

Example 14

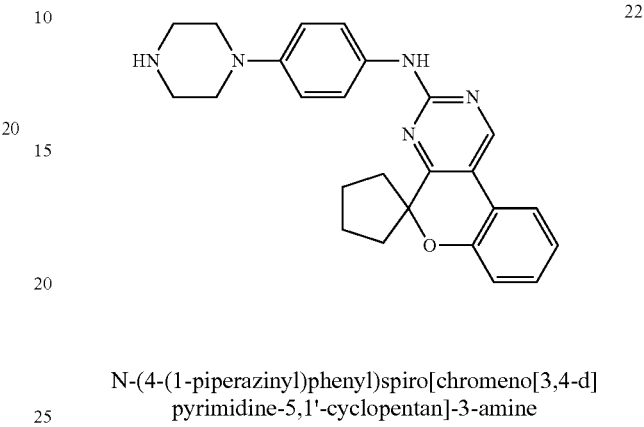

N-(4-(1-piperazinyl)phenyl)spiro[chromeno[3,4-d]pyrimidine-5,1'-cyclopentan]-3-amine Title compound (22) was prepared from compound (21) using chemistry similar to that described in Example 2. $^1$H NMR (400 MHz, DMSO-d$_6$) δ ppm 9.57 (1H, s), 8.92 (1H, s), 7.83 (1H, dd, J=7.8, 1.6 Hz), 7.59 (2H, d, J=9.0 Hz), 7.15-7.23 (1H, m), 7.01-7.08 (1H, m), 6.93 (1H, dd, J=8.0, 1.0 Hz), 6.84-6.91 (2H, m), 2.97 (4H, dd, J=6.1, 3.7 Hz), 2.82 (4H, dd, J=5.9, 3.9 Hz), 2.14-2.25 (2H, m), 1.99-2.09 (2H, m), 1.86-1.96 (2H, m, J=7.6, 4.1 Hz), 1.77-1.86 (2H, m). LCMS-ESI (POS), M/Z, M+1: Found 414.1.

Example 15

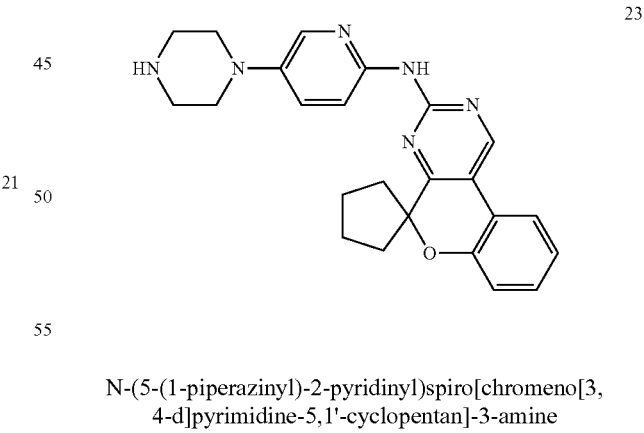

N-(5-(1-piperazinyl)-2-pyridinyl)spiro[chromeno[3,4-d]pyrimidine-5,1'-cyclopentan]-3-amine Title compound (23) was prepared from compound (21) using chemistry similar to that described in Example 2. $^1$H NMR (400 MHz, DMSO-d$_6$) δ ppm 9.62 (1H, s), 8.92 (1H, s), 7.97 (1H, d, J=9.4 Hz), 7.92 (1H, d, J=2.7 Hz), 7.80 (1H, dd, J=7.8, 1.2 Hz), 7.36 (1H, dd, J=9.0, 3.1 Hz), 7.12-7.19 (1H, m), 6.96-7.03 (1H, m), 6.88 (1H, dd, J=8.0, 1.0 Hz), 2.92-3.01 (4H, m), 2.72-2.83 (4H, m), 2.07-2.18 (2H, m), 1.96-2.04

(2H, m), 1.81-1.92 (2H, m), 1.69-1.80 (2H, m). LCMS-ESI (POS), M/Z, M+1: Found 415.1.

Example 16

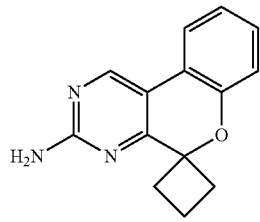

24 spiro[chromeno[3,4-d]pyrimidine-5,1'-cyclobutan]-3-amine

Title compound (24) was prepared using chemistry similar to that described in Example 1. ¹H NMR (400 MHz, DMSO-d₆) δ ppm 8.75 (1H, s), 7.76 (1H, dd, J=7.8, 1.6 Hz), 7.17 (1H, td, J=7.8, 1.6 Hz), 6.97-7.05 (2H, m), 6.94 (2H, br. s.), 2.53-2.60 (2H, m), 2.29-2.38 (2H, m), 1.81-2.03 (2H, m). LCMS-ESI (POS), M/Z, M+1: Found 240.1.

Example 17

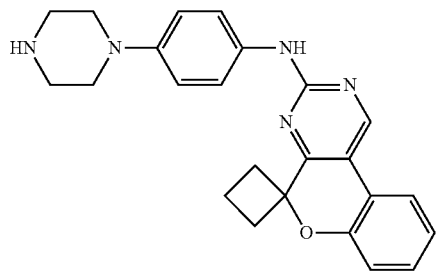

25

N-(4-(1-piperazinyl)phenyl)spiro[chromeno[3,4-d]pyrimidine-5,1'-cyclobutan]-3-amine Title compound (25) was prepared from compound (24) using chemistry similar to that described in Example 2. ¹H NMR (400 MHz, DMSO-d₆) δ ppm 9.64 (1H, s), 8.93 (1H, s), 7.83 (1H, dd, J=7.8, 1.6 Hz), 7.66 (2H, d, J=9.0 Hz), 7.17-7.25 (1H, m), 6.99-7.09 (2H, m), 6.89 (2H, d, J=9.4 Hz), 2.92-3.02 (4H, m), 2.78-2.87 (4H, m), 2.56-2.66 (2H, m), 2.36-2.47 (2H, m), 1.87-2.07 (2H, m). LCMS-ESI (POS), M/Z, M+1: Found 400.1.

Example 18

26

7-fluoro-2',3',5',6'-tetrahydrospiro[chromeno[3,4-d]pyrimidine-5,4'-pyran]-3-amine

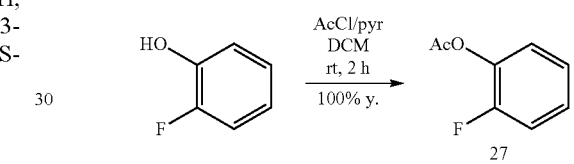

2-Fluorophenyl acetate (27) Acetyl chloride (32 mL, 446 mmol) was slowly added through an addition funnel to a stirred solution of 2-fluorophenol (45 mL, 446 mmol) and pyridine (40 mL, 491 mmol) in DCM (300 mL) at rt. After 2 h, 2 N HCl (300 mL) was added and the aqueous layer was separated and extracted with DCM (1×). The organics were combined, washed with brine (2×), dried over Na₂SO₄ and concentrated to give 2-fluorophenyl acetate (27) (69.0 g, 100% yield) as a colorless oil. ¹H NMR (400 MHz, DMSO-d₆) δ ppm 7.18-7.40 (4H, m), 2.32 (3H, s).

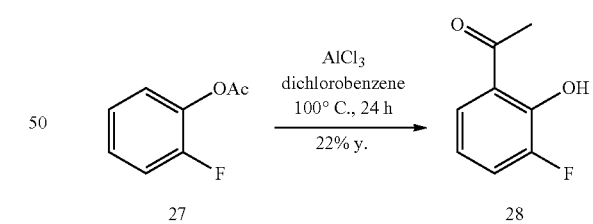

1-(3-Fluoro-2-hydroxyphenyl)ethanone (28) A solution of 2-fluorophenyl acetate (27) (69.9 g, 453.49 mmol) in dichlorobenzene (40 mL) was added dropwise to a solution of aluminum chloride (65 g) in dichlorobenzene (50 mL). After being warmed to 100° C. for 24 h, the reaction mixture was allowed to cool to room temperature, diluted with dichloromethane, and slowly poured into 2 N HCl aqueous solution cooled at 0° C. The mixture was thoroughly stirred for 20 min and the aqueous layer was separated and extracted with dichloromethane (2×). The organic extracts were combined, washed with brine (2×), dried over Na₂SO₄, and concentrated in vacuo. The residue was subjected to combi-flash column chromatography (EtOAc/Hexanes) to give 1-(3-fluoro-2-hydroxyphenyl)ethanone (28) (15.0 g, 21.5% yield) as a white solid. $^1$H NMR (400 MHz, CHLOROFORM-d) δ ppm 7.68-7.79 (2H, m), 7.07 (1H, t, J=8.4 Hz), 5.73 (1H, d, J=4.3 Hz), 2.57 (3H, s).

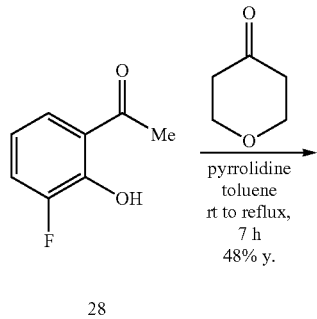

28

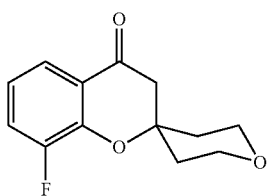

29

8-Fluoro-2',3',5',6'-tetrahydrospiro[chromene-2,4'-pyran]-4(3H)-one (29)

Pyrrolidine (4.8 ml, 58 mmol) was added to a stirred solution of 1-(3-fluoro-2-hydroxyphenyl)ethanone (28) (5.9 g, 39 mmol) and tetrahydro-4h-pyran-4-one (4.6 ml, 50 mmol) in toluene (40 mL) at rt. After the exotherm subsided, the reaction mixture was stirred at rt for 1 h. then subjected to Dean-Stark reflux conditions for 6 h. The reaction mixture was cooled, poured into ice and 2 N HCl aqueous solution, and extracted with EtOAc (2×). The combined organics were washed with 2 N HCl aqueous solution (1×), 2 N NaOH aqueous solution (2×), brine (1×), and dried over Na$_2$SO$_4$. Concentration in vacuo gave 8-fluoro-2',3',5',6'-tetrahydrospiro[chromene-2,4'-pyran]-4(3H)-one (29) (4.4 g, 48% yield) which was taken onto the next step without further purification. $^1$H NMR (400 MHz, DMSO-d$_6$) δ ppm 7.51-7.60 (2H, m), 7.00-7.07 (1H, m), 3.60-3.73 (4H, m), 2.93 (2H, s), 1.71-1.92 (4H, m).

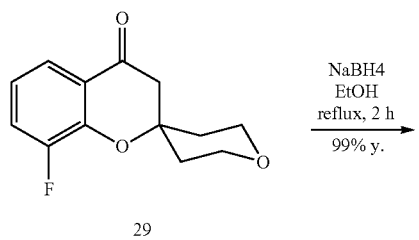

29

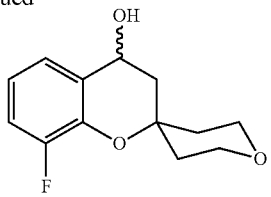

30

8-Fluoro-2',3,3',4,5',6'-hexahydrospiro[chromene-2,4'-pyran]-4-ol (30) A solution of 8-fluoro-2',3',5',6'-tetrahydrospiro[chromene-2,4'-pyran]-4(3H)-one (29) (4.4 g, 19 mmol) in EtOH (90 mL) was dropwise added into a stirred suspension of sodium borohydride (0.33 ml, 9.3 mmol) in EtOH (30 mL) at rt. The resulting mixture was stirred at reflux for 2 h and then concentrated in vacuo. The residue was dissolved in EtOAc, washed with saturated NaHCO$_3$ aqueous solution (2×), brine (1×), dried over Na$_2$SO$_4$, and concentrated in vacuo to give 8-fluoro-2',3,3',4,5',6'-hexahydrospiro[chromene-2,4'-pyran]-4-ol (30) (4.4 g, 99% yield) as a light yellow oil which was used in the next step without purification. $^1$H NMR (400 MHz, DMSO-d$_6$) δ ppm 7.22 (1H, dd, J=7.8, 0.8 Hz), 7.02-7.11 (1H, m), 6.81-6.89 (1H, m), 5.49 (1H, d, J=6.3 Hz), 4.67-4.78 (1H, m), 3.56-3.77 (4H, m), 2.14 (1H, dd, J=13.7, 5.9 Hz), 1.75-1.86 (3H, m), 1.60-1.75 (2H, m).

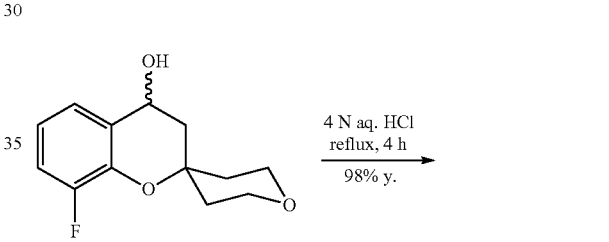

30

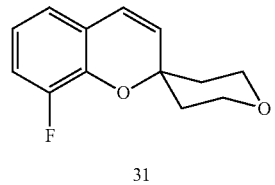

31

8-Fluoro-2',3',5',6'-tetrahydrospiro[chromene-2,4'-pyran] (31) A mixture of 8-fluoro-2',3,3',4,5',6'-hexahydrospiro[chromene-2,4'-pyran]-4-ol (30) (4.4 g, 18 mmol) and 4 N hydrogen chloride (55 ml, 220 mmol) was heated at reflux for 4 h. The reaction mixture was then cooled to rt, poured into H$_2$O, and extracted with EtOAc (2×). The combined organics were washed with brine (1×), dried over Na$_2$SO$_4$. Concentration in vacuo gave 8-fluoro-2',3',5',6'-tetrahydrospiro[chromene-2,4'-pyran] (31) (4.0 g, 98% yield) as a colorless crystalline solid. $^1$H NMR (400 MHz, DMSO-d$_6$) δ ppm 7.04-7.12 (1H, m), 6.93 (1H, m), 6.82-6.89 (1H, m), 6.54 (1H, dd, J=9.8, 2.0 Hz), 5.89 (1H, d, J=9.8 Hz), 3.62-3.78 (4H, m), 1.72-1.87 (4H, m). LCMS-ESI (POS), M/Z, M+1: Found 221.1.

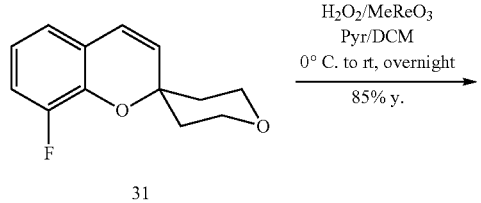

31

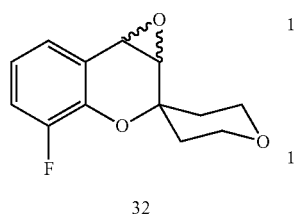

32

4-Fluoro-1a,2',3',5',6',7b-hexahydrospiro[oxireno[c]chromene-2,4'-pyran] (32) To a stirred ice-cooled solution of 8-fluoro-2',3',5',6'-tetrahydrospiro[chromene-2,4'-pyran] (31) (4.0 g, 18 mmol) and methyltrioxorhenium(VII) (0.091 g, 0.36 mmol) in DCM (50 mL) and pyridine (0.36 ml, 4.4 mmol) was added dropwise aqueous hydrogen peroxide (31%, 2.7 ml, 27 mmol) under nitrogen atmosphere. The resulting mixture was stirred at 0° C. for 10 min and at rt overnight. 3.6 mL of NaClO (commercial Clorox) was added dropwise at rt. The resulting mixture was stirred at rt for 1 h. Then the reaction mixture was poured into ice $H_2O$, and extracted with DCM (2×). The combined organics were washed with brine (1×), dried over $Na_2SO_4$. Concentration in vacuo gave 4-fluoro-1a,2',3',5',6',7b-hexahydrospiro[oxireno[c]chromene-2,4'-pyran] (32) (4.0 g, 93% yield) containing unreacted 31 (~9%). This material was used in the next step without purification. $^1$H NMR (400 MHz, DMSO-$d_6$) δ ppm 7.30-7.35 (1H, m), 7.19-7.28 (1H, m), 6.92-7.00 (1H, m), 4.12 (1H, dd, J=4.7, 2.0 Hz), 3.65-3.87 (4H, m), 3.52-3.61 (1H, m), 2.00-2.09 (1H, m), 1.73-1.85 (2H, m), 1.25-1.34 (1H, m).

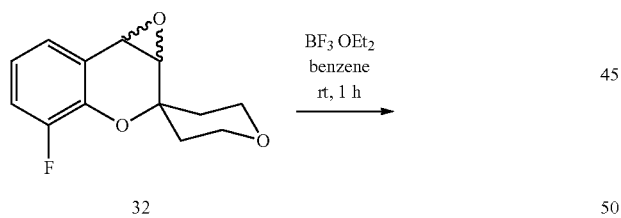

8-Fluoro-2',3',5',6'-tetrahydrospiro[chromene-2,4'-pyran]-3(4H)-one (33) Boron Trifluoride etherate (0.5 mL, 4 mmol) was added to a stirred solution of crude 4-fluoro-1a,2',3',5',6',7b-hexahydrospiro[oxireno[c]chromene-2,4'-pyran] (32) (2.0 g, 8 mmol) in benzene (40 mL) under a nitrogen atmosphere and stirred at rt for 70 min. Upon workup, the mixture was poured into ice and saturated $NaHCO_3$ aqueous solution, and extracted with EtOAc (2×). The combined organics were washed with brine (1×), dried over $Na_2SO_4$, and concentrated in vacuo to give crude 8-fluoro-2',3',5',6'-tetrahydrospiro[chromene-2,4'-pyran]-3(4H)-one (33) (1.97 g, 99% yield), which was used in the next step without purification.

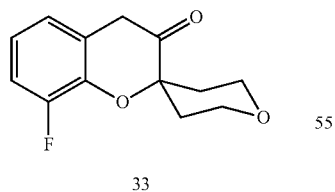

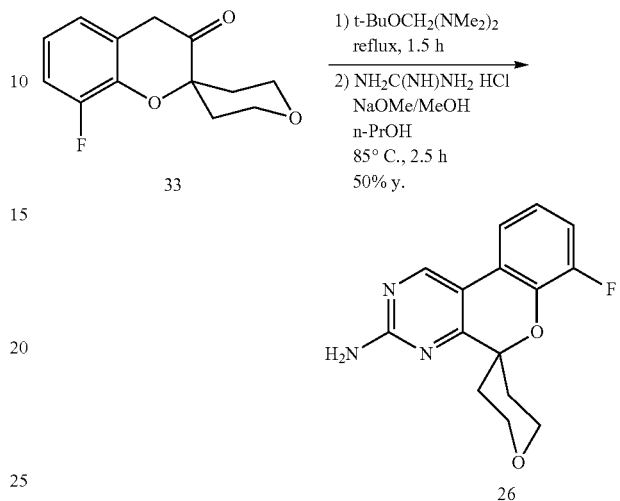

7-Fluoro-2',3',5',6'-tetrahydrospiro[chromeno[3,4-d]pyrimidine-5,4'-pyran]-3-amine (26) A solution of crude 8-fluoro-2',3',5',6'-tetrahydrospiro[chromene-2,4'-pyran]-3(4H)-one (33) (1.600 g, 6.77 mmol) and tert-butoxy-bis(dimethylamino)methane (2.10 ml, 10.2 mmol) was stirred at reflux for 1.5 h. The temperature was lowered to 85° C. and n-propanol (5 mL), guanidine hydrochloride (3.2 g, 34 mmol), and sodium methoxide in MeOH (4.37 M solution) (4.6 ml, 20 mmol) were added sequentially. The resulting mixture was stirred at 85° C. for 2.5 h, then poured into ice and saturated $NaHCO_3$ aqueous solution, and extracted with EtOAc (2×). The combined organics were washed with brine (1×) and dried over $Na_2SO_4$. The residue after concentration in vacuo was subjected to combi-flash flash column chromatography (EtOAc/Hexanes) to give 7-fluoro-2',3',5',6'-tetrahydrospiro[chromeno[3,4-d]pyrimidine-5,4'-pyran]-3-amine (26) (0.95 g, 49% yield over 2 steps) as an off-white solid. $^1$H NMR (400 MHz, DMSO-$d_6$) δ ppm 8.81 (1H, s), 7.59-7.64 (1H, m), 7.09-7.16 (1H, m), 6.98-7.08 (3H, m), 3.70-3.88 (4H, m), 2.07-2.21 (2H, m), 1.76 (2H, d, J=12.5 Hz). LCMS-ESI (POS), M/Z, M+1: Found 288.1.

Example 19

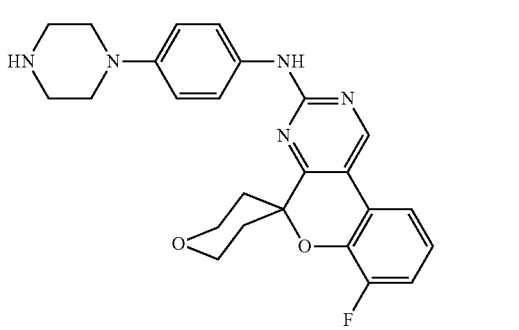

7-fluoro-N-(4-(1-piperazinyl)phenyl)-2',3',5',6'-tetrahydrospiro[chromeno[3,4-d]pyrimidine-5,4'-pyran]-3-amine Title compound (34) was prepared from compound (36) using chemistry similar to that described in Example 2. $^1$H NMR (400 MHz, DMSO-$d_6$) δ ppm 9.73 (1H, s), 8.99 (1H, s), 7.68 (1H, d, J=7.8 Hz), 7.59 (2H, d, J=9.0 Hz), 7.14-7.22 (1H, m), 7.02-7.10 (1H, m), 6.91 (2H, d, J=9.0 Hz), 3.72-3.93 (4H, m), 2.94-3.05 (4H, m), 2.79-2.88 (4H, m), 2.13-2.25 (2H, m), 1.84 (2H, d, J=13.7 Hz). LCMS-ESI (POS), M/Z, M+1: Found 448.1.

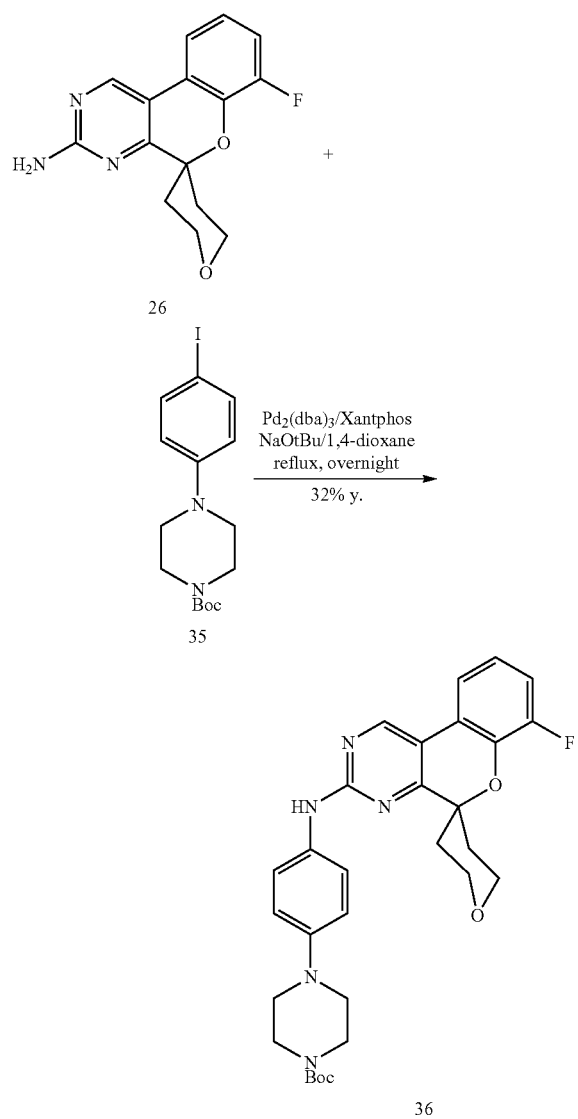

4-(4-((7-Fluoro-2',3',5',6'-tetrahydrospiro[chromeno[3,4-d]pyrimidine-5,4'-pyran]-3-yl)amino)phenyl)-1-piperazinecarboxylate (36) A 10 mL single-necked RBF was charged sequentially with (26) (0.105 g, 0.37 mmol), tert-butyl 4-(4-iodophenyl)piperazine-1-carboxylate (35) (0.14 g, 0.37 mmol), tris(dibenzylideneacetone)dipalladium (o) (0.0033 g, 0.0037 mmol), 9,9-dimethyl-4,5-bis(diphenylphosphino) xanthene (0.0047 g, 0.0080 mmol) (XantPhos) and sodium tert-butoxide (0.049 g, 0.51 mmol). The flask was then subjected to 3 cycles of evacuation and back-filling with N$_2$ before 1,4-dioxane (1.8 mL) was introduced through a syringe under N$_2$. The resulting mixture was then stirred at reflux in a preheated oil bath overnight. The reaction was cooled and subjected to combi-flash column chromatography (EtOAc/Hexanes) to give 4-(4((7-fluoro-2',3',5',6'-tetrahydrospiro[chromeno[3,4-d]pyrimidine-5,4'-pyran]-3-yl) amino)phenyl)-1-piperazinecarboxylate (36) (0.065 g, 32% yield) which was used directly in the next step. LCMS-ESI (POS), M/Z, M+1: Found 548.2.

Example 20

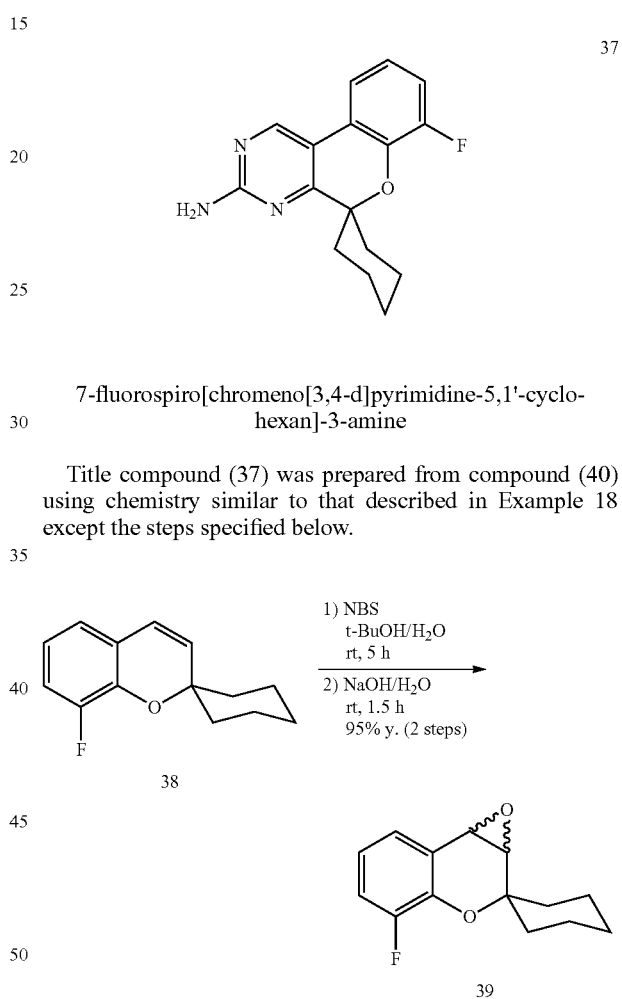

7-fluorospiro[chromeno[3,4-d]pyrimidine-5,1'-cyclohexan]-3-amine

Title compound (37) was prepared from compound (40) using chemistry similar to that described in Example 18 except the steps specified below.

4'-Fluoro-1a',7b'-dihydrospiro[cyclohexane-1,2'-oxireno [c]chromene] (39) To a stirred solution of 8-fluorospiro [chromene-2,1'-cyclohexane] (38) (1.82 g, 8.3 mmol) in a mixed solvent containing t-BuOH (30 mL) and H$_2$O (20 mL) was added at rt NBS (1.7 g, 9.6 mmol) in 3 portions over a period of 30 min Stirring continued at rt for 5 h. A solution of sodium hydroxide (1.0 g, 25 mmol) in H$_2$O (12 mL) was added at rt. Stirring continued at rt for 1.5 h. Then the mixture was poured into H$_2$O and extracted with EtOAc (2×). The combined organics were washed with brine (1×), dried over Na$_2$SO$_4$, and concentrated in vacuo to give 4'-fluoro-1a',7b'-dihydrospiro[cyclohexane-1,2'-oxireno[c]chromene] (39) (2.0 g, 102% yield) as a lightly red-colored oil, which was highly pure and taken onto the next step without further purification. ¹H NMR (400 MHz, CHLOROFORM-d) δ ppm 7.09-7.14 (1H, m), 7.02-7.09 (1H, m), 6.82-6.89 (1H, m), 3.89 (1H, dd, J=4.3, 2.0 Hz), 3.51 (1H, d, J=4.7 Hz), 2.10-2.20 (1H, m), 1.86-1.98 (1H, m), 1.31-1.78 (8H, m).

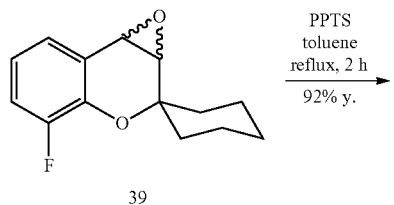

8-Fluorospiro[chromene-2,1'-cyclohexan]-3(4H)-one (40) A mixture of 4'-fluoro-1a',7b'-dihydrospiro[cyclohexane-1,2'-oxireno[c]chromene] (39) (2.0 g, 8.5 mmol) and pyridinium tosylate (2.4 g, 9.4 mmol) in toluene (50 mL) was refluxed for 2 h, then cooled and poured into ice and saturated NaHCO₃ aqueous solution, and extracted with EtOAc (2×). The combined organics were washed thoroughly with saturated NaHCO₃ aqueous solution (3×) followed by brine (1×), dried over Na₂SO₄, and concentrated in vacuo to give 8-fluorospiro[chromene-2,1'-cyclohexan]-3(4H)-one (40) (1.84 g, 92% yield) as a reddish oil which was taken onto the next step without purification. ¹H NMR (400 MHz, CHLOROFORM-d) δ ppm 7.00-7.07 (1H, m), 6.92-7.00 (1H, m), 6.84-6.90 (1H, m), 3.60 (2H, s), 1.57-1.87 (9H, m), 1.29-1.36 (1H, m).

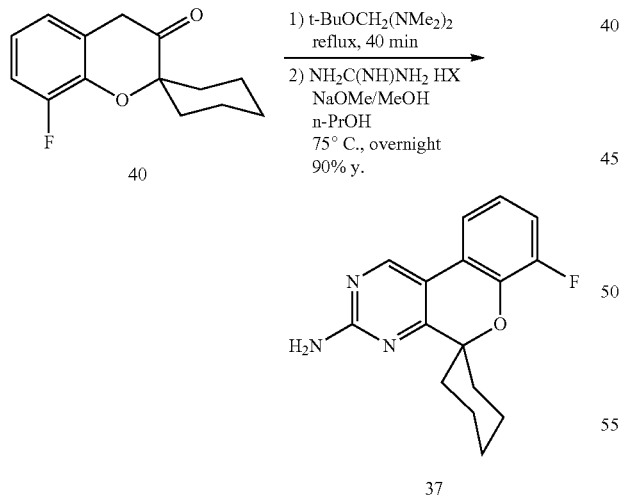

7-Fluorospiro[chromeno[3,4-d]pyrimidine-5,1'-cyclohexan]-3-amine (37) A solution of 8-fluorospiro[chromene-2,1'-cyclohexan]-3(4H)-one (40) (1.84 g, 7.85 mmol) in tert-butoxy-bis(dimethylamino)methane (3.57 ml, 17.3 mmol) was heated at reflux for 40 min. After brief cooling, n-propanol (35 mL), guanidine hydrochloride (4.50 g, 47.1 mmol), and sodium methoxide in MeOH (4.37 M) (5.39 ml, 23.6 mmol) were added sequentially. The resulting mixture was stirred at 75° C. overnight. Upon workup, the mixture was poured into ice and saturated NaHCO₃ aqueous solution and extracted with EtOAc (2×). The combined organics were washed with brine (2×), dried over Na₂SO₄, and concentrated in vacuo to give the crude 7-fluorospiro[chromeno[3,4-d]pyrimidine-5,1'-cyclohexan]-3-amine (37) (2.15 g, 95.9% yield). ¹H NMR (500 MHz, DMSO-d₆) δ ppm 8.78 (1H, s), 7.59 (1H, d, J=7.8 Hz), 7.07-7.14 (1H, m), 6.94-7.03 (3H, m), 1.56-1.89 (9H, m), 1.20-1.33 (1H, m). LCMS-ESI (POS), M/Z, M+1: Found 286.1.

Example 21

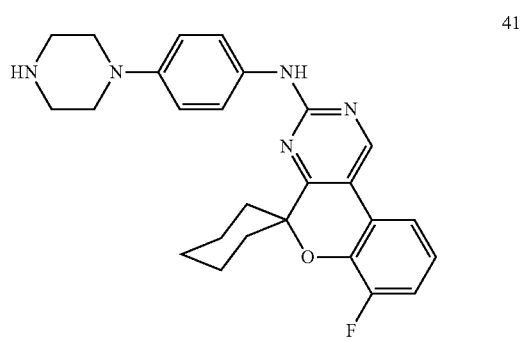 [SMILES: Fc1cccc2c1OC1(CCCCC1)c1nc(Nc3ccc(N4CCNCC4)cc3)ncc1-2]

7-fluoro-N-(4-(1-piperazinyl)phenyl)spiro[chromeno[3,4-d]pyrimidine-5,1'-cyclohexan]-3-amine Title compound (41) was prepared from compound (37) using chemistry similar to that described in Example 19. ¹H NMR (500 MHz, DMSO-d₆) δ ppm 9.66 (1H, s), 8.95 (1H, s), 7.66 (1H, d, J=7.8 Hz), 7.55-7.62 (2H, m), 7.11-7.19 (1H, m), 6.99-7.07 (1H, m), 6.86-6.92 (2H, m), 2.94-3.02 (4H, m), 2.78-2.87 (4H, m), 1.85-1.97 (4H, m), 1.59-1.81 (5H, m), 1.27-1.37 (1H, m). LCMS-ESI (POS), M/Z, M+1: Found 446.2.

Example 22

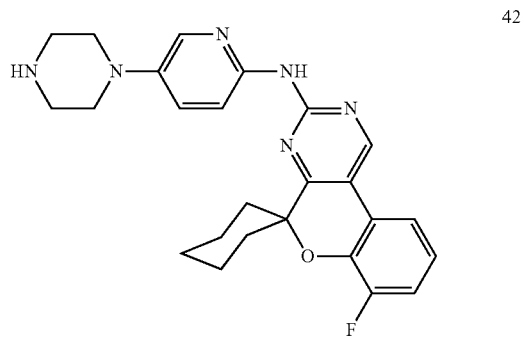 [SMILES: Fc1cccc2c1OC1(CCCCC1)c1nc(Nc3ccc(N4CCNCC4)cn3)ncc1-2]

7-fluoro-N-(5-(1-piperazinyl)-2-pyridinyl)spiro[chromeno[3,4-d]pyrimidine-5,1'-cyclohexan]-3-amine The title compound (42) was prepared from compound (37) using chemistry similar to that described in Example 19.

¹H NMR (400 MHz, DMSO-d₆) δ ppm 9.79 (1H, s), 9.01 (1H, s), 8.03 (1H, d, J=9.4 Hz), 7.99 (1H, d, J=2.7 Hz), 7.69 (1H, d, J=7.8 Hz), 7.44 (1H, dd, J=9.0, 3.1 Hz), 7.13-7.22 (1H, m), 7.01-7.09 (1H, m), 3.01-3.08 (4H, m), 2.80-2.89 (4H, m), 1.58-1.99 (9H, m), 1.26-1.42 (1H, m). LCMS-ESI (POS), M/Z, M+1: Found 447.3

Example 23

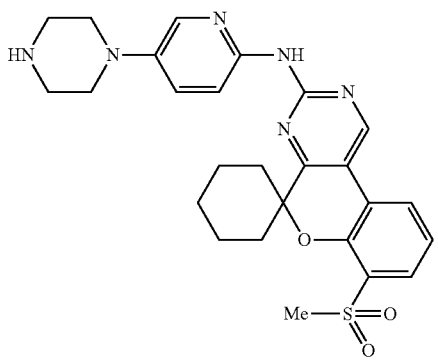

7-(methylsulfonyl)-N-(5-(1-piperazinyl)-2-pyridinyl)spiro[chromeno[3,4-d]pyrimidine-5,1'-cyclohexan]-3-amine Title compound (43) was prepared from compound (45) using chemistry similar to that described in Example 2. ¹H NMR (500 MHz, MeOD-d3) δ 9.15 (1H, s), 8.23 (1H, m), 8.21 (1H, m), 7.97 (1H, d, J=2.7 Hz), 7.95 (1H, dd, J1=7.8 Hz, J2=1.4 Hz), 7.57 (1H, d, J=9.6 Hz), 7.33 (1H, t, J=7.8 Hz), 3.54 (4H, m), 3.44 (4H, m), 3.30 (3H, s), 2.04-2.16 (6H, m), 1.84 (1H, br d, J=13.5 Hz), 1.67 (2H, m), 1.41 (1H, m); LCMS-ESI (POS), M/Z, M+1: Found 507.0.

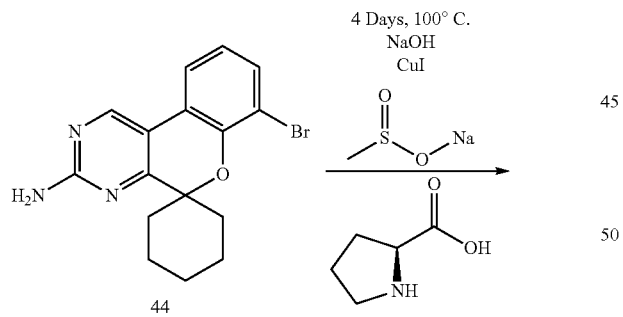

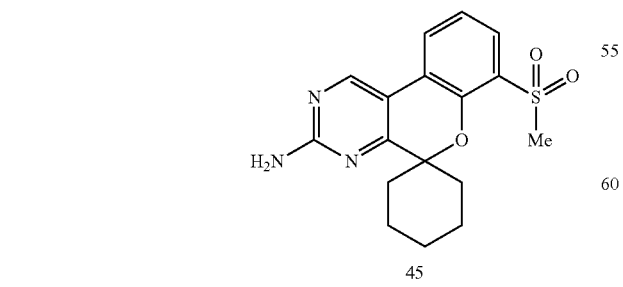

7-(bromo)spiro[chromeno[3,4-d]pyrimidine-5,1'-cyclohexan]-3-amine (44). Compound (44) was prepared using chemistry similar to that described in Example 20. ¹H NMR (500 MHz, DMSO-d6) δ 8.79 (1H, s), 7.78 (1H, dd, J1=7.9 Hz, 1.3 Hz), 7.43 (1H, dd, J1=8.1 Hz, J2=1.5 Hz), 7.00 (2H, br s), 6.95 (1H, t, J=7.8 Hz), 1.80-1.88 (6H, m), 1.75 (1H, br d, J=11.8 Hz), 1.58-1.62 (2H, m), 1.23-1.31 (1H, m); LCMS-ESI (POS), M/Z, M+1: Found 346.2.

7-(Methylsulfonyl)spiro[chromeno[3,4-d]pyrimidine-5,1'-cyclohexan]-3-amine (45). Copper (I) iodide (28 mg, 0.15 mmol, 0.4 eq) was added to a degassed solution of 7-bromo-spiro[chromeno[3,4-d]pyrimidine-5,1'-cyclohexan]-3-amine (44) (0.126 g, 0.36 mmol), (S)-pyrrolidine-2-carboxylic acid (0.034 g, 0.29 mmol), sodium methanesulfinate (0.074 g, 0.73 mmol) and sodium hydroxide (0.015 g, 0.36 mmol) in DMSO (1 mL) under Argon. The mixture was heated at 100° C., for 4 days. After workup, chromatography on silica gel afforded 15 mg of 7-(methylsulfonyl)spiro[chromeno[3,4-d]pyrimidine-5,1'-cyclohexan]-3-amine (45) as a brown solid. LCMS-ESI (POS), M/Z, M+1: Found 345.9.

Example 24

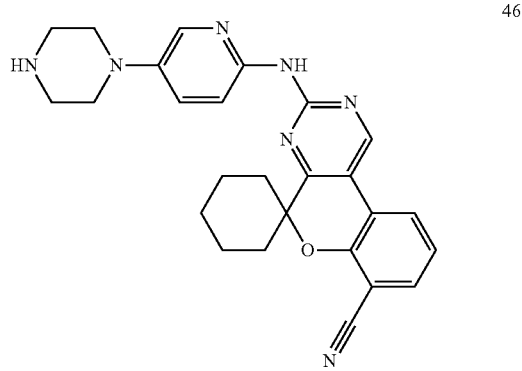 [SMILES: N#Cc1cccc2c1OC1(CCCCC1)c1nc(Nc3ccc(N4CCNCC4)cn3)ncc1-2]

3-((5-(1-piperazinyl)-2-pyridinyl)amino)spiro[chromeno[3,4-d]pyrimidine-5,1'-cyclohexane]-7-carbonitrile Title compound (46) was prepared from compound (47) using chemistry similar to that described in Example 2. ¹H NMR (500 MHz, DMSO-d6) δ 10.40 (1H, br s), 9.12 (1H, s), 8.93 (2H, br s), 8.25 (1H, dd, J1=8.1 Hz, J2=1.5 Hz), 8.08 (1H, d, J=2.9 Hz), 8.01 (1H, d, J=9.0 Hz), 7.71 (1H, dd, J1=7.5 Hz, J2=1.4 Hz), 7.68 (1H, dd. J1=9.5 Hz, J2=3.4), 7.24 (1H, t, J=7.9 Hz), 3.38 (4H, m), 3.26 (4H, m), 1.90-2.01 (4H, m), 1.77-1.85 (3H, m), 1.65-1.71 (2H, m), 1.26-1.43 (1H, m); LCMS-ESI (POS), M/Z, M+1: Found 454.3.

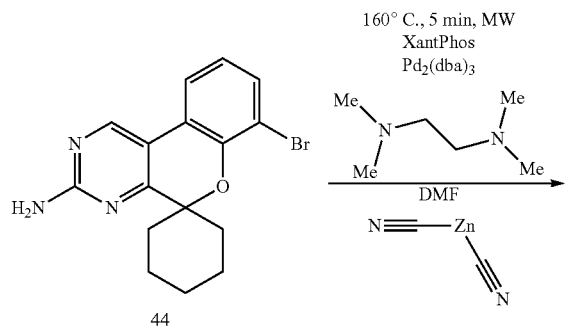

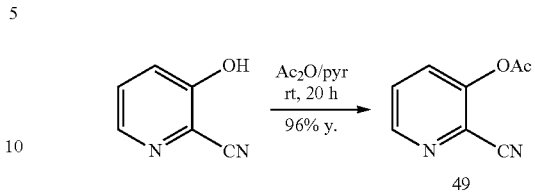

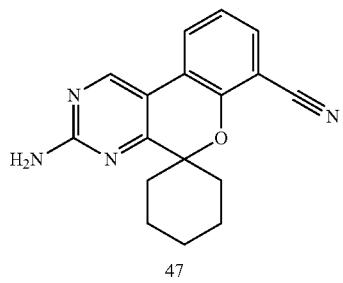

3-Aminospiro[chromeno[3,4-d]pyrimidine-5,1'-cyclohexane]-7-carbonitrile (47). A solution of 7-bromospiro[chromeno[3,4-d]pyrimidine-5,1'-cyclohexan]-3-amine (44) (0.233 g, 0.673 mmol), Zn(CN)$_2$ (0.0474 g, 0.404 mmol), and TMEDA (0.0202 ml, 0.135 mmol), in DMF (2 mL) was degassed by bubbling nitrogen through the solution for ~1 min before adding Pd$_2$(dba)$_3$ (0.0462 g, 0.0505 mmol), and Xantphos (4,5-bis(diphenylphosphino)-9,9-dimethyl-9H-xanthene, 0.0584 g, 0.101 mmol). The mixture was heated to 160° C. for 5 min with microwave irradiation. The reaction mixture was diluted in water and extracted with 10% iPrOH/DCM (3×75 ml). The organic layer was dried with MgSO$_4$ and concentrated in vacuo. Purification on a 40 g combiflash column [(dry loaded), eluting with 50% EtOAc:Hexane to 100% EtOAc then with 4% MeOH/36% DCM/EtOAc] afforded 3-aminospiro[chromeno[3,4-d]pyrimidine-5,1'-cyclohexane]-7-carbonitrile (47) as a white solid (0.133 g, 68%). LCMS-ESI (POS), M/Z, M+1: Found 293.0.

Example 25

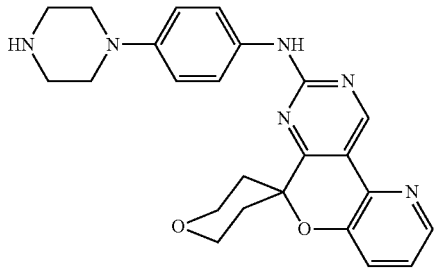

N-(4-(1-piperazinyl)phenyl)-2,3,5,6-tetrahydrospiro[pyran-4,6'-pyrido[2',3':5,6]pyrano[3,4-d]pyrimidin]-8'-amine

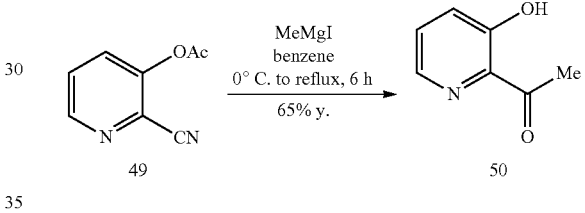

2-Cyanopyridin-3-yl acetate (49) Acetic anhydride (4.1 ml, 43.71 mmol) was added slowly to a stirred solution of 3-hydroxypicolinonitrile (5.0 g, 41.63 mmol) in pyridine (15 mL) at rt. The resulting mixture was stirred at rt overnight and then concentrated in vacuo. The residue was dissolved in EtOAc, washed with sat'd NaHCO$_3$ aqueous solution (1×) and brine (1×), and dried over Na$_2$SO$_4$. Purification by combi-flash chromatography (EtOAc/Hexanes) gave 2-cyanopyridin-3-yl acetate (49) (6.5 g, 96.30% yield). $^1$H NMR (400 MHz, DMSO-d$_6$) δ ppm 8.67 (1H, dd, J=4.7, 1.2 Hz), 8.03 (1H, dd, J=8.6, 1.2 Hz), 7.87 (1H, dd), 2.42 (3H, s).

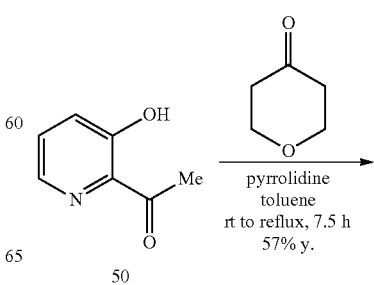

1-(3-Hydroxypyridin-2-yl)ethanone (50) A flame-dried 250 mL round bottom flask was charged with methylmagnesium iodide in ether (67.0 ml, 200 mmol). This solution was stirred in an ice-H$_2$O bath as 2-cyanopyridin-3-yl acetate (49) (6.5 g, 40 mmol) in benzene (45 mL) was cannulated in over a period of 40 min. The resulting mixture was refluxed for 5.5 hrs, then cooled in an ice-H$_2$O bath and cautiously quenched with saturated NH$_4$Cl aqueous solution. The aqueous layer was cautiously neutralized with 2N HCl aqueous solution and then extracted with EtOAc (2×). The combined organic layer was washed with brine (1×) and dried over anhydrous Na$_2$SO$_4$. Purification by combi-flash column chromatography (EtOAc/Hexanes) gave 1-(3-hydroxypyridin-2-yl)ethanone (50) (3.6 g, 65% yield) as a light yellow solid. $^1$H NMR (400 MHz, DMSO-d$_6$) δ ppm 11.58 (1H, s), 8.27 (1H, dd, J=4.3, 1.6 Hz), 7.61 (1H, dd, J=8.4, 4.3 Hz), 7.47 (1H, dd, J=8.4, 1.6 Hz), 2.69 (3H, s).

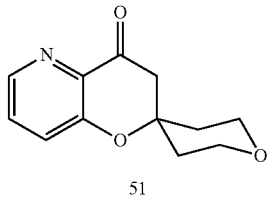

2,3,5,6-Tetrahydrospiro[pyran-4,2'-pyrano[3,2-b]pyridin]-4'(3'H)-one (51) Pyrrolidine (5.5 ml, 66 mmol) was added dropwise to a stirred solution of 1-(3-hydroxypyridin-2-yl)ethanone (50) (6.0 g, 44 mmol) and tetrahydro-4h-pyran-4-one (5.3 ml, 57 mmol) in toluene (100 mL) and stirred at rt for 2 h. The mixture was then refluxed under Dean-Stark conditions for 5.5 h. The volatiles were removed and the residue was purified by combi-flash column chromatography (EtOAc/Hexanes) to give 2,3,5,6-tetrahydrospiro[pyran-4,2'-pyrano[3,2-b]pyridin]-4'(3'H)-one (51) (5.4 g, 57% yield) H NMR LC-MS as a reddish oil which solidified upon standing at rt. $^1$H NMR (400 MHz, DMSO-d$_6$) δ ppm 8.36 (1H, dd, J=3.3, 2.2 Hz), 7.55-7.62 (2H, m), 3.62-3.73 (4H, m), 2.99 (2H, s), 1.72-1.89 (4H, m). LCMS-ESI (POS), M/Z, M+1: Found 220.0.

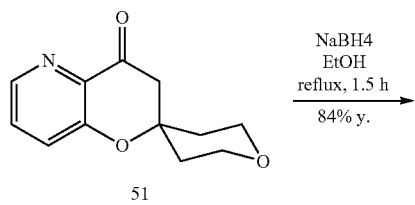

2,3,3',4',5,6-Hexahydrospiro[pyran-4,2'-pyrano[3,2-b]pyridin]-4'-ol (52) A solution of 2,3,5,6-tetrahydrospiro[pyran-4,2'-pyrano[3,2-b]pyridin]-4'(3'H)-one (51) (5.4 g, 24.63 mmol) in EtOH (45 mL) was added dropwise via an addition funnel to a stirred suspension of sodium borohydride (0.69 g, 18.47 mmol) in EtOH (15 mL) at rt. The resulting mixture was refluxed for 1.5 h. The reaction mixture was concentrated in vacuo, poured into ice and saturated NaHCO$_3$ aqueous solution, and extracted with EtOAc (2×). The combined organics were washed with brine (1×), dried over anhydrous sodium sulfate, and concentrated in vacuo to give 2,3,3',4',5,6-hexahydrospiro[pyran-4,2'-pyrano[3,2-b]pyridin]-4'-ol (52) (4.6 g, 84% yield) as a colorless oil. $^1$H NMR (400 MHz, DMSO-d$_6$) δ ppm 8.16 (1H, dd, J=3.9, 2.0 Hz), 7.17-7.27 (2H, m), 5.45 (1H, d, J=4.3 Hz), 4.63-4.71 (1H, m), 3.60-3.73 (4H, m), 2.17 (1H, dd, J=14.1, 6.3 Hz), 1.97 (1H, dd, J=14.1, 6.7 Hz), 1.59-1.86 (4H, m). LCMS-ESI (POS), M/Z, M+1: Found 222.1.

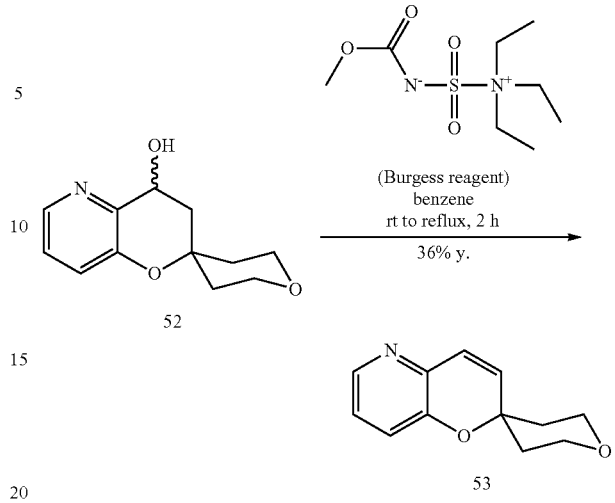

2,3,5,6-Tetrahydrospiro[pyran-4,2'-pyrano[3,2-b]pyridine] (53) Burgess reagent (1.6 g, 6.6 mmol) was added in one portion to a stirred solution of 2,3,3',4',5,6-hexahydrospiro[pyran-4,2'-pyrano[3,2-b]pyridin]-4'-ol (52) (1.2 g, 5.5 mmol) in benzene (30 mL) at rt. The resulting mixture was stirred at rt for 20 min and then refluxed for 1.5 h. The mixture was poured into ice and 2 N NaOH aqueous solution, extracted with EtOAc (3×), dried over Na$_2$SO$_4$, and concentrated in vacuo. The residue was purified by combi-flash column chromatography (EtOAc/Hexanes) to give 2,3,5,6-tetrahydrospiro[pyran-4,2'-pyrano[3,2-b]pyridine] (53) (0.40 g, 36% yield) as a colorless liquid. $^1$H NMR (400 MHz, CHLOROFORM-d) δ ppm 8.11 (1H, dd, J=4.7, 1.6 Hz), 7.10-7.15 (1H, m), 7.05 (1H, dd, J=8.4, 4.7 Hz), 6.59 (1H, d, J=10.6 Hz), 5.88 (1H, d, J=9.8 Hz), 3.86-3.96 (2H, m), 3.75-3.82 (2H, m), 1.94-2.03 (2H, m), 1.77-1.88 (2H, m). LCMS-ESI (POS), M/Z, M+1: Found 204.1.

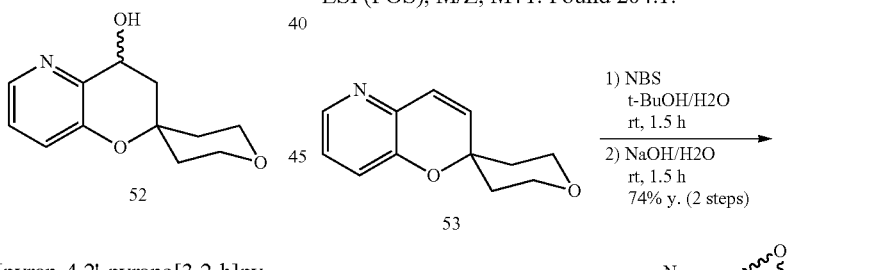

1a,2',3',5',6',7b-Hexahydrospiro[oxireno[4,5]pyrano[3,2-b]pyridine-2,4'-pyran](54) NBS (0.85 g, 4.8 mmol) was added in 4 portions over a period of 10 min to a stirred solution of (53) (0.81 g, 4.0 mmol) in a mixed solvents of t-BuOH (10 mL) and water (14 mL) and stirred at rt for 3 h. A solution of NaOH (0.236 g, 5.90 mmol) in water (12 mL) was then added and stirred at rt for 100 min. The product was extracted into t-butyl methyl ether (2×), dried over Na$_2$SO$_4$ and concentrated in vacuo to give 1a,2',3',5',6',7b-hexahydrospiro[oxireno[4,5]pyrano[3,2-b]pyridine-2,4'-pyran] (54) (0.77 g, 88% yield) as a colorless film which was used in the next step without further purification. ¹H NMR (400 MHz, CHLOROFORM-d) δ ppm 8.14 (1H, dd, J=4.5, 1.8 Hz), 7.11-7.20 (2H, m), 4.07 (1H, d, J=4.3 Hz), 3.85-3.97 (2H, m), 3.63-3.77 (2H, m), 3.54 (1H, d, J=4.3 Hz), 1.96-2.03 (2H, m), 1.71-1.82 (1H, m), 1.42 (1H, dd, J=14.1, 2.3 Hz). LCMS-ESI (POS), M/Z, M+1: Found 220.0.

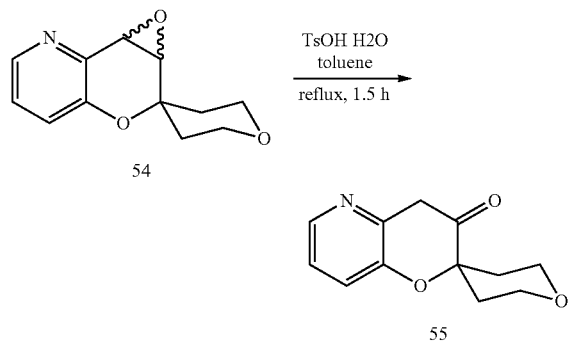

2,3,5,6-Tetrahydrospiro[pyran-4,2'-pyrano[3,2-b]pyridin]-3'(4'H)-one (55) A solution of 1a,2',3',5',6',7b-hexahydrospiro[oxireno[4,5]pyrano[3,2-b]pyridine-2,4'-pyran] (54) (0.77 g, 3.5 mmol) and p-toluenesulfonic acid monohydrate (0.73 g, 3.9 mmol) in toluene (50 mL) was refluxed for 1.5 h. After cooling, the reaction mixture was poured into ice and saturated NaHCO₃ aqueous solution and then extracted with EtOAc (3x). The organic layer was dried over Na₂SO₄ and concentrated in vacuo to give 2,3,5,6-tetrahydrospiro[pyran-4,2'-pyrano[3,2-b]pyridin]-3'(4'H)-one (55) (0.66 g, 86% yield) as a dark film which was used in the next step without further purification. LCMS-ESI (POS), M/Z, M+1: Found 220.0.

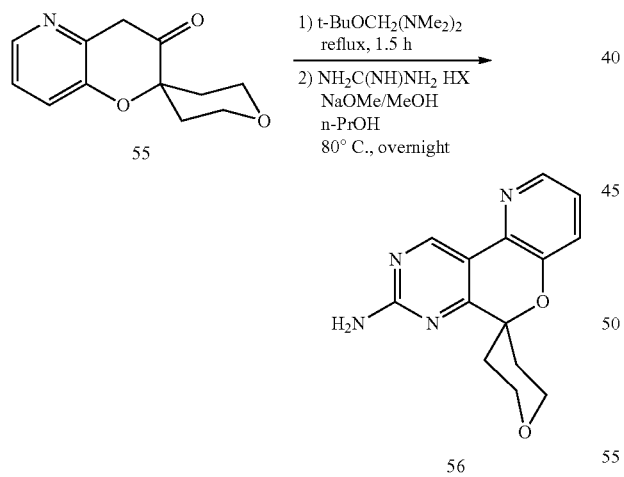

2,3,5,6-tetrahydrospiro[pyran-4,6'-pyrido[2',3':5,6]pyrano[3,4-d]pyrimidin]-8'-amine (56) A solution of 2,3,5,6-tetrahydrospiro[pyran-4,2'-pyrano[3,2-b]pyridin]-3'(4'H)-one (55) (0.61 g, 2.78 mmol) in tert-butoxy-bis(dimethylamino)methane (1.15 ml, 5.6 mmol) was heated at 105° C. for 1.5 h then lowered to 80° C. N-propanol (15 mL), guanidine hydrochloride (1.33 g, 13.9 mmol), and sodium methanolate (1.9 ml, 8.3 mmol) were added sequentially. The mixture was stirred at 80° C. for overnight. Upon workup, the reaction mixture was poured into ice and saturated NaHCO₃ aqueous solution and extracted with EtOAc (3x). The combined organics were dried over Na₂SO₄ and concentrated in vacuo and purified by combi-flash chromatography (EtOAc/Hexanes) to give 2,3,5,6-tetrahydrospiro[pyran-4,6'-pyrido[2',3':5,6]pyrano[3,4-d]pyrimidin]-8'-amine (56) (150 mg) as an off-white solid. ¹H NMR (400 MHz, CHLOROFORM-d) δ ppm 9.10 (1H, s), 8.25 (1H, dd, J=4.7, 1.2 Hz), 7.30 (1H, dd, J=8.0, 1.4 Hz), 7.15 (1H, dd, J=8.2, 4.7 Hz), 5.24 (2H, s), 3.88-4.01 (4H, m), 2.26-2.40 (2H, m), 1.81-1.92 (2H, m, J=14.1, 2.0 Hz). LCMS-ESI (POS), M/Z, M+1: Found 271.0.

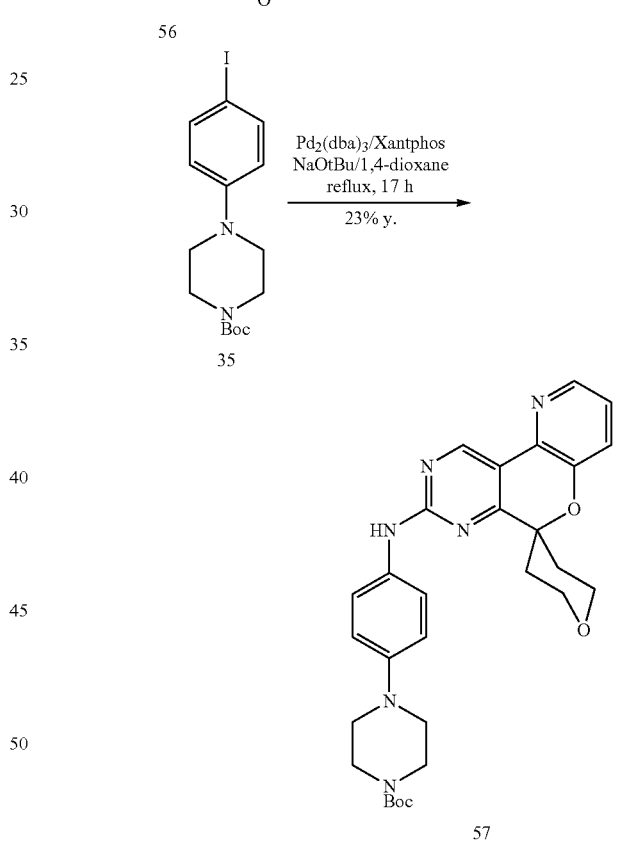

4-(4-(2,3,5,6-Tetrahydrospiro[pyran-4,6'-pyrido[2',3':5,6]pyrano[3,4-d]pyrimidin]-8'-ylamino)phenyl)-1-piperazinecarboxylate (57) A 10 mL single-necked round bottom flask was charged with 2,3,5,6-tetrahydrospiro[pyran-4,6'-pyrido[2',3':5,6]pyrano[3,4-d]pyrimidin]-8'-amine (56) (0.12 g, 0.44 mmol), tert-butyl 4-(4-iodophenyl)piperazine-1-carboxylate (0.26 g, 0.67 mmol), tris(dibenzylideneacetone)dipalladium (o) (4.1 mg, 0.0044 mmol), 9,9-dimethyl-4,5-bis(diphenylphosphino)xanthene (7.7 mg, 0.013 mmol) and sodium t-butoxide (60 mg, 0.62 mmol). The flask was then subjected to 3 cycles of evacuation-backfilling with N₂. Then, 1,4-dioxane (3 mL) was introduced through a syringe under N₂. The resulting crude mixture was then stirred at reflux for 17 h. The mixture was cooled to rt and subjected to combi-flash column chromatography (EtOAc/Hexanes) to give pure 4-(4-(2,3,5,6-tetrahydrospiro[pyran-4,6'-pyrido[2',3':5,6]pyrano[3,4-d]pyrimidin]-8'-ylamino)phenyl)-1-piperazinecarboxylate (57) (0.055 g, 23% yield) as a light yellow film, which was used in the next step. LCMS-ESI (POS), M/Z, M+1: Found 531.2.

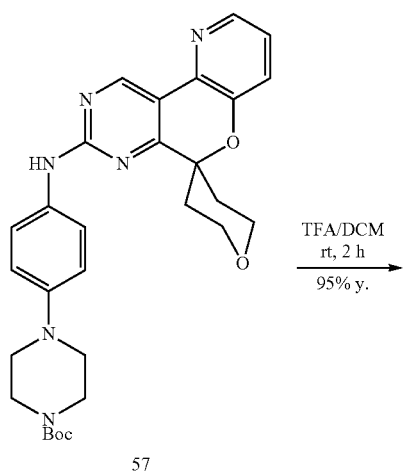

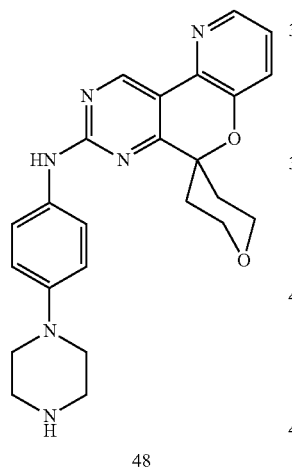

N-(4-(1-piperazinyl)phenyl)-2,3,5,6-tetrahydrospiro[pyran-4,6'-pyrido[2',3':5,6]pyrano[3,4-d]pyrimidin]-8'-amine (48) A mixture of 4-(4-(2,3,5,6-tetrahydrospiro[pyran-4,6'-pyrido[2',3':5,6]pyrano[3,4-d]pyrimidin]-8'-ylamino)phenyl)-1-piperazinecarboxylate (57) (0.055 g, 0.10 mmol) and TFA (2.00 ml, 26 mmol) in DCM (15 mL) was stirred at rt for 2 h. After the volatiles were removed under vacuum, the residue was dissolved in EtOAc, poured into ice and 2N NaOH aqueous solution, and extracted with EtOAc (2×). The combined organics were dried over Na₂SO₄ and concentrated in vacuo. The residue was triturated with EtOAc/Hexanes to give N-(4-(1-piperazinyl)phenyl)-2,3,5,6-tetrahydrospiro[pyran-4,6'-pyrido[2',3':5,6]pyrano[3,4-d]pyrimidin]-8'-amine (48) (0.050 g) as a light yellow solid. ¹H NMR (400 MHz, DMSO-d₆) δ ppm 9.89 (1H, s), 9.11 (1H, s), 8.31 (1H, dd, J=4.7, 1.6 Hz), 7.66 (2H, d, J=9.0 Hz), 7.55 (1H, dd, J=8.0, 1.4 Hz), 7.33 (1H, dd, J=8.2, 4.7 Hz), 6.98 (2H, d, J=9.0 Hz), 3.81-3.97 (4H, m), 3.02-3.11 (4H, m), 2.85-2.95 (4H, m), 2.20-2.33 (2H, m), 1.91 (2H, d, J=13.7 Hz). LCMS-ESI (POS), M/Z, M+1: Found 432.1.

Example 26

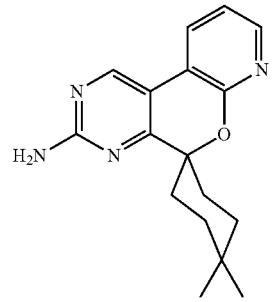

4,4-dimethylspiro[cyclohexane-1,5'-pyrido[3',3':5,6]pyrano[3,4-d]pyrimidin]-3'-amine

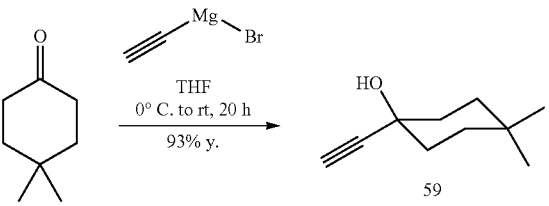

1-Ethynyl-4,4-dimethylcyclohexanol (59) A dried 250 mL single-necked round bottom flask was charged with ethynylmagnesium bromide, 0.5 m solution in THF (105 ml, 52 mmol). This solution was cooled in an ice-H₂O bath while a solution of 4,4-dimethylcyclohexanone (6.0 g, 48 mmol) in THF (100 mL) was added dropwise through an addition funnel over a period of 20 min. The resulting mixture was stirred at 0° C. and then gradually warmed up to ambient temperature overnight. The mixture was poured into ice and saturated NH₄Cl aqueous solution and extracted with EtOAc (2×). The combined organics were washed with brine (1×), dried over Na₂SO₄, and concentrated in vacuo to give 1-ethynyl-4,4-dimethylcyclohexanol (59) (6.7 g, 93% yield) as an off-white solid. (the product tends to sublimate). ¹H NMR (400 MHz, DMSO-d₆) δ ppm 5.24 (1H, s), 3.31 (1H, s), 1.50-1.69 (4H, m), 1.22-1.40 (4H, m), 0.87 (6H, d, J=3.1 Hz).

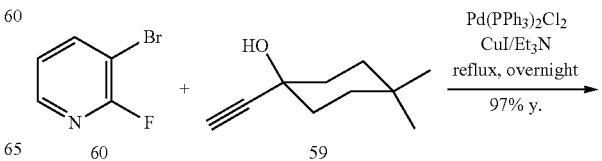

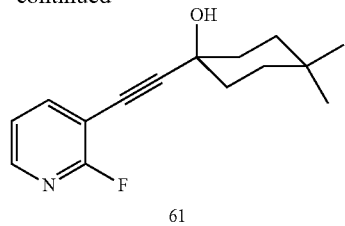

1-(2-(2-Fluoropyridin-3-yl)ethynyl)-4,4-dimethylcyclohexanol (61) A 250 mL single-necked round-bottomed flask was charged with 1-ethynyl-4,4-dimethylcyclohexanol (59) (6.7 g, 44 mmol), trans-dichlorobis(triphenyl-phosphine)palladium (ii) (1.4 g, 2.0 mmol), and copper(i) iodide (0.76 g, 4.0 mmol) followed by triethylamine (100 ml, 716 mmol). The flask was then purged with $N_2$ for 10 min before 3-bromo-2-fluoropyridine (60) (7.00 g, 40 mmol) was introduced. Purging with $N_2$ continued for 15 min and the resulting mixture was stirred at 105° C. overnight. After cooling, the reaction mixture was filtered through a layer of Celite and the cake was washed with DCM (500 mL). The filtrate was concentrated in vacuo and the crude residue was subjected to combi-flash column chromatography (EtOAc/Hexanes) to give 1-(2-(2-fluoropyridin-3-yl)ethynyl)-4,4-dimethylcyclohexanol (61) (9.5 g, 97% yield) as an oil. $^1$H NMR (500 MHz, CHLOROFORM-d) δ ppm 8.12-8.19 (1H, m), 7.79-7.86 (1H, m), 7.14-7.19 (1H, m), 2.05 (1H, s), 1.90-1.98 (2H, m), 1.80-1.88 (2H, m), 1.40-1.60 (4H, m), 0.97 (6H, d, J=3.7 Hz). LCMS-ESI (POS), M/Z, M+1: Found 248.1

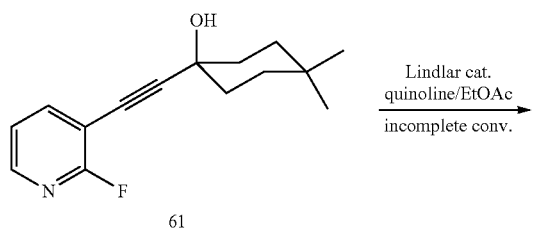

(Z)-1-(2-(2-fluoropyridin-3-yl)vinyl)-4,4-dimethylcyclohexanol (62) A 1 L single-necked round bottom flask was charged with 1-(2-(2-fluoropyridin-3-yl)ethynyl)-4,4-dimethylcyclohexanol (61) (3.5 g, 14 mmol) dissolved in EtOAc (70 mL) and quinoline (1.7 ml, 14 mmol). The flask was briefly purged with $N_2$ before Lindlar Catalyst (5% Pd on $CaCO_3$ poisoned w/Pb) (1.5 g, 14 mmol) was added. The resulting mixture was subjected to 3 cycles of evacuation and back-filling with $H_2$ and then balloon hydrogenated for 5 h. Another 1 equivalent of Lindlar Catalyst (5% Pd on $CaCO_3$ poisoned w/Pb) (1.5 g, 14 mmol) was added and the balloon hydrogenation continued over the weekend (2 days). The reaction was quenched with DCM (100 mL) followed by vacuum filtration through a layer of Celite. The cake was washed thoroughly with more DCM. After concentration in vacuo, the residue was subjected to combi-flash column chromatography (EtOAc/Hexanes) to give (Z)-1-(2-(2-fluoropyridin-3-yl)vinyl)-4,4-dimethylcyclohexanol (62) (~1.6 g) as a nearly colorless liquid. (containing some unreacted starting material (61).) This product was used in the next step. LCMS-ESI (POS), M/Z, M+1: Found 250.1

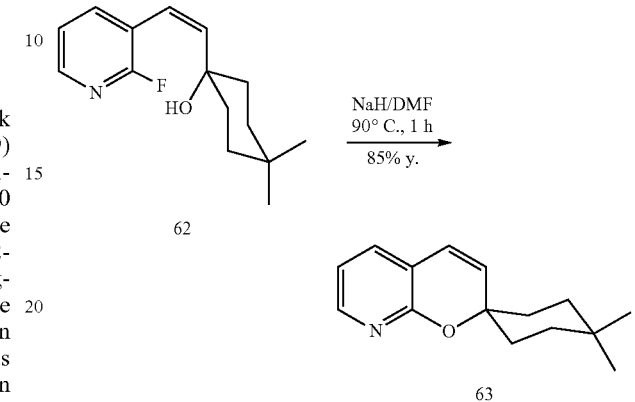

4,4-Dimethylspiro[cyclohexane-1,2'-pyrano[2,3-b]pyridine] (63) Sodium hydride, (60% dispersion in mineral oil, 0.40 g, 11 mmol) was added in one portion to a stirred solution at rt of impure (Z)-1-(2-(2-fluoropyridin-3-yl)vinyl)-4,4-dimethylcyclohexanol (62) (2.2 g, 8.8 mmol) in DMF (90 mL). The resulting mixture was stirred at rt for 5 min and then heated at 90° C. for 1 h. After cooling, the mixture was poured into ice cold saturated $NaHCO_3$ aqueous solution and extracted with EtOAc (2×). The combined organics were washed with brine (1×), dried over $Na_2SO_4$, and concentrated in vacuo. Purification by combi-flash column chromatography (EtOAc/Hexanes) gave 4,4-dimethylspiro[cyclohexane-1,2'-pyrano[2,3-b]pyridine] (63) (0.7 g, ~85% yield) as a light yellow solid. $^1$H NMR (400 MHz, CHLOROFORM-d) δ ppm 8.02 (1H, dd, J=5.1, 2.0 Hz), 7.25 (1H, dd, J=7.0, 2.0 Hz), 6.80 (1H, dd, J=7.0, 5.1 Hz), 6.31 (1H, d, J=9.8 Hz), 5.70 (1H, d, J=9.8 Hz), 1.92-2.04 (2H, m), 1.73-1.84 (2H, m), 1.60-1.72 (2H, m), 1.19-1.30 (2H, m), 1.01 (3H, s), 0.95 (3H, s). LCMS-ESI (POS), M/Z, M+1: Found 230.2

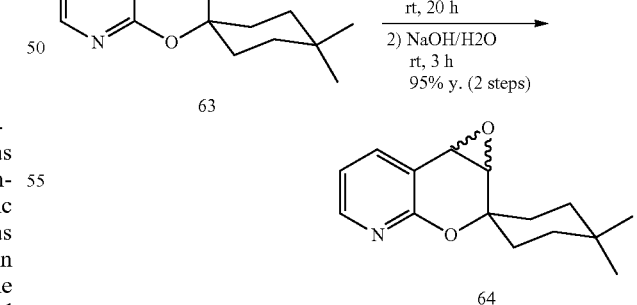

4,4-Dimethyl-1a',7b'-dihydrospiro[cyclohexane-1,2'-oxireno[4,5]pyrano[2,3-b]pyridine] (64) NBS (0.62 g, 3.5 mmol) was added in 2 portions over a period of 10 min to a stirred solution of 4,4-dimethylspiro[cyclohexane-1,2'-pyrano[2,3-b]pyridine] (63) (0.70 g, 3.1 mmol) in a mixed solvent of t-BuOH (20 mL) and $H_2O$ (10 mL) at rt. Stirring continued at rt until LC-MS showed completion of bromohydrin formation. An aqueous solution of sodium hydroxide (0.37 g, 9.2 mmol) (10 mL) was added to the reaction mixture. Stirring at rt continued for 3 h at which time LC-MS showed completion of epoxide formation. Upon workup, the mixture was poured into saturated NaHCO$_3$ aqueous solution and extracted with EtOAc (3×). The combined organics were dried over Na$_2$SO$_4$ and concentrated in vacuo to give the crude 4,4-dimethyl-1a',7b'-dihydrospiro[cyclohexane-1,2'-oxireno[4,5]pyrano[2,3-b]pyridine] (64) (0.88 g, >95% yield) as a colorless oil which was used in the next step without further purification. $^1$H NMR (500 MHz, CHLOROFORM-d) δ ppm 8.22 (1H, dd, J=5.1, 2.0 Hz), 7.69 (1H, dd, J=7.3, 2.0 Hz), 6.92 (1H, dd, J=7.2, 5.0 Hz), 3.90 (1H, d, J=4.2 Hz), 3.55 (1H, d, J=4.2 Hz), 2.07-2.12 (1H, m), 1.81-1.92 (2H, m), 1.61-1.73 (2H, m), 1.49-1.56 (1H, m), 1.36-1.41 (1H, m), 1.20-1.26 (1H, m), 1.02 (3H, s), 0.98 (3H, s). LCMS-ESI (POS), M/Z, M+1: Found 246.1

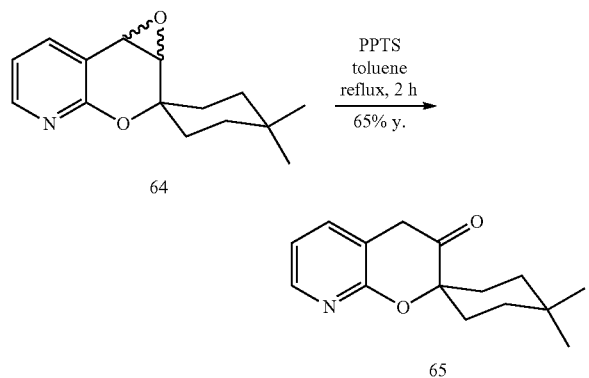

4,4-Dimethylspiro[cyclohexane-1,2'-pyrano[2,3-b]pyridin]-3'(4'H)-one (65) A solution of 4,4-dimethyl-1a',7b'-dihydrospiro[cyclohexane-1,2'-oxireno[4,5]pyrano[2,3-b]pyridine] (64) (0.75 g, 3.1 mmol) and pyridinium tosylate (0.88 g, 3.5 mmol) in toluene (20 mL) was heated at reflux for 2 h. After cooling, the mixture was poured into ice and saturated NaHCO$_3$ aqueous solution and extracted with EtOAc (2×). The combined organics were washed with saturated NaHCO$_3$ aqueous solution (3×) followed by brine (1×), dried over Na$_2$SO$_4$, and concentrated in vacuo to give crude 4,4-dimethylspiro[cyclohexane-1,2'-pyrano[2,3-b]pyridin]-3'(4'H)-one (65) (0.53 g, 71% yield), which was used in the next step without purification. $^1$H NMR (400 MHz, CHLOROFORM-d) δ ppm 8.23 (1H, dd, J=4.9, 1.8 Hz), 7.46 (1H, dd, J=7.4, 2.0 Hz), 7.02 (1H, dd, J=7.4, 5.1 Hz), 3.61 (2H, s), 1.75-1.97 (4H, m), 1.61-1.69 (2H, m), 1.24-1.32 (2H, m), 1.02 (3H, s), 0.97 (3H, s). LCMS-ESI (POS), M/Z, M+1: Found 246.1, Calculated 246.14.

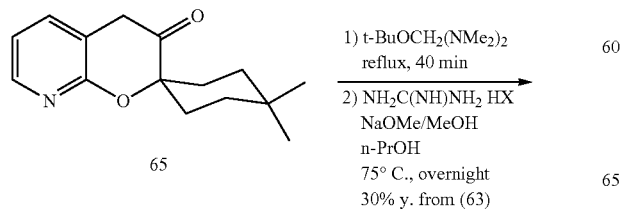

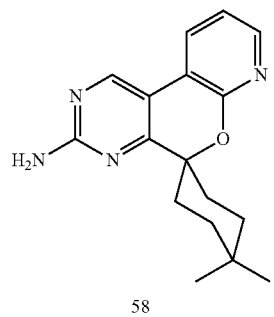

4,4-Dimethylspiro[cyclohexane-1,5'-pyrido[3',2':5,6]pyrano[3,4-d]pyrimidin]-3'-amine (58) A solution of 4,4-dimethylspiro[cyclohexane-1,2'-pyrano[2,3-b]pyridin]-3'(4'H)-one (65) (0.88 g, 3.6 mmol) and tert-butoxy-bis(dimethylamino)methane (1.6 ml, 7.9 mmol) in 2.5 mL of THF was heated at reflux for 30 min. After brief cooling, n-propanol (15 mL), guanidine hydrochloride (2.1 g, 22 mmol), and sodium methoxide in MeOH (4.37 M) (2.5 ml, 11 mmol) were added sequentially. The resulting mixture was stirred at 85° C. for 40 min. Upon workup, the mixture was poured into ice and saturated NaHCO$_3$ aqueous solution and extracted with EtOAc (2×). The combined organics were washed with saturated NaHCO$_3$ aqueous solution (1×) followed by brine (1×), dried over Na$_2$SO$_4$, and concentrated in vacuo. Purification by combi-flash column chromatography (EtOAc/Hexanes) gave 4,4-dimethylspiro[cyclohexane-1,5'-pyrido[3',3':5,6]pyrano[3,4-d]pyrimidin]-3'-amine (58) (0.23 g, 30% yield from compound (63)) as an off-white solid. $^1$H NMR (500 MHz, CHLOROFORM-d) δ ppm 8.61 (1H, s), 8.19 (1H, dd, J=4.9, 2.0 Hz), 7.89 (1H, dd, J=7.6, 2.0 Hz), 7.01 (1H, dd, J=7.6, 4.9 Hz), 5.26 (2H, br. s.), 2.11-2.20 (2H, m), 1.82-1.97 (4H, m), 1.27-1.34 (2H, m), 1.05 (3H, s), 1.02 (3H, s). LCMS-ESI (POS), M/Z, M+1: Found 297.0.

Example 27

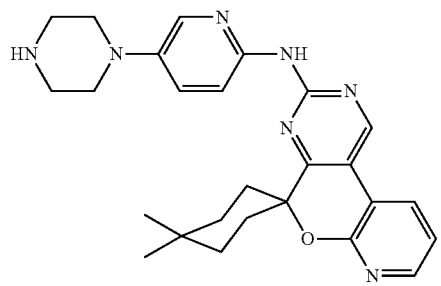

4,4-dimethyl-N-(5-(1-piperazinyl)-2-pyridinyl)spiro[cyclohexane-1,5'-pyrido[3',3':5,6]pyrano[3,4-d]pyrimidin]-3'-amine

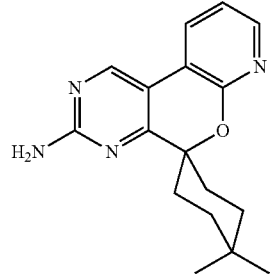

58

+

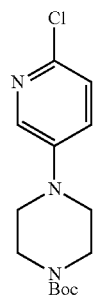

67

Pd₂(dba)₃/Xantphos
NaOtBu/1,4-dioxane
reflux, 2.5 h
────────────→
95% y.

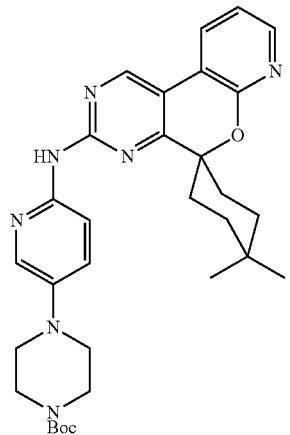

68 tert-Butyl 4-(6-((4,4-dimethylspiro[cyclohexane-1,5'-pyrido[3',3':5,6]pyrano[3,4-d]pyrimidin]-3'-yl)amino)-3-pyridinyl)-1-piperazinecarboxylate (68) A 25 mL single-necked round bottom flask was charged with 4,4-dimethylspiro[cyclohexane-1,5'-pyrido[3',3':5,6]pyrano[3,4-d]pyrimidin]-3'-amine (58) (56 mg, 189 µmol), tert-butyl 4-(6-chloropyridin-3-yl)piperazine-1-carboxylate (67) (68 mg, 227 µmol), tris(dibenzylideneacetone)-dipalladium (o) (8.7 mg, 9.4 µmol), 9,9-dimethyl-4,5-bis(diphenylphosphino)-xanthene (14 mg, 24 µmol), 1,4-dioxane (2 mL) and sodium tert-butoxide (54 mg, 567 µmol). The vessel was subjected to 3 cycles of evacuation and back-filling with N₂ before 1,4-dioxane was added under N₂. The mixture was stirred at reflux under N₂ for 2.5 h at which time LC-MS showed completion. After the volatiles were removed, the residue was purified by combi-flash column chromatography (MeOH/DCM) to give tert-butyl-4-(6-((4,4-dimethylspiro[cyclohexane-1,5'-pyrido[3', 3':5,6]pyrano[3,4-d]pyrimidin]-3'-yl)amino)-3-pyridinyl)-1-piperazinecarboxylate (68) (100 mg, 95% yield) as an off-white solid. LCMS-ESI (POS), M/Z, M+1: Found 558.3

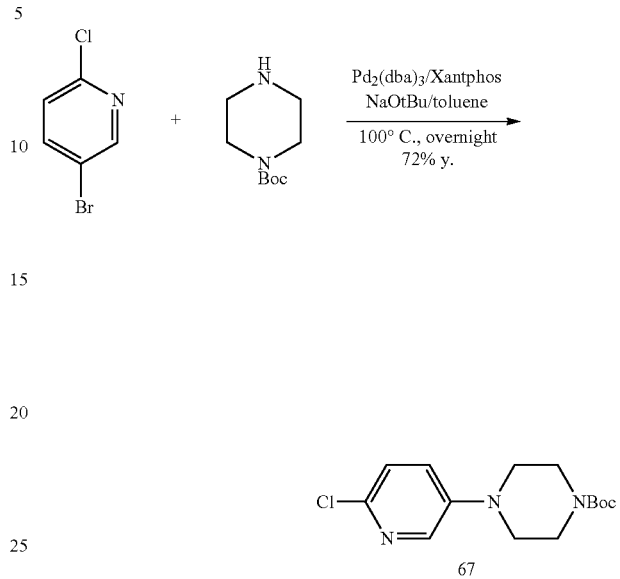

tert-Butyl 4-(6-chloropyridin-3-yl)piperazine-1-carboxylate (67) A 250 mL single-necked round bottom flask was charged with 5-bromo-2-chloropyridine (11.4 g, 59.2 mmol), tert-butyl 1-piperazinecarboxylate (11.0 g, 59.2 mmol), tris(dibenzylideneacetone)dipalladium (o) (0.542 g, 0.592 mmol), 9,9-dimethyl-4,5-bis(diphenylphosphino)xanthene (1.03 g, 1.78 mmol), and sodium t-butoxide (8.54 g, 88.9 mmol). The flask was subjected to 3 cycles of evacuation and back-filling with N₂ before toluene (100 mL) was introduced under N₂. The resulting mixture was stirred at 100° C. overnight. After cooling, the product was purified by combi-flash column chromatography (EtOAc/Hexanes) to give tert-butyl 4-(6-chloropyridin-3-yl)piperazine-1-carboxylate (66) (12.7 g, 72.0% yield) as an off-white solid. ¹H NMR (500 MHz, DMSO-d₆) δ ppm 8.08 (1H, d, J=3.2 Hz), 7.43 (1H, dd, J=8.8, 3.2 Hz), 7.31 (1H, d, J=8.8 Hz), 3.42-3.49 (4H, m), 3.14-3.21 (4H, m), 1.42 (9H, s). LCMS-ESI (POS), M/Z, M+1: Found 298.1

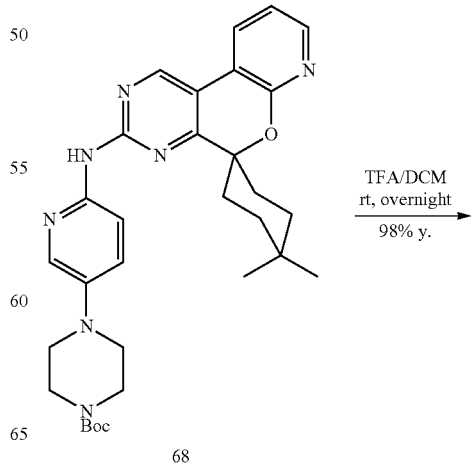

68

TFA/DCM
rt, overnight
────────────→
98% y.

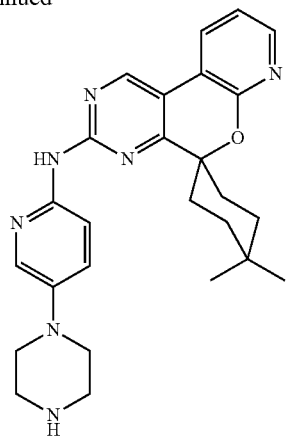

66

4,4-Dimethyl-N-(5-(1-piperazinyl)-2-pyridinyl)spiro[cyclohexane-1,5'-pyrido[3',3':5,6]pyrano[3,4-d]pyrimidin]-3'-amine (66) Trifluoroacetic acid (2 mL, 26.9 mmol) was added to a stirred solution of tert-butyl 4-(6-((4,4-dimethylspiro[cyclohexane-1,5'-pyrido[3',3':5,6]pyrano[3,4-d]pyrimidin]-3'-yl)amino)-3-pyridinyl)-1-piperazinecarboxylate (68) (100 mg, 0.18 mmol) in DCM (8 mL) at rt and stirred overnight. Upon workup, the mixture was poured into ice and 4 N aqueous HCl solution, extracted with 10% i-PrOH/chloroform (3×) and dried over Na$_2$SO$_4$. After concentration in vacuo, the residue was triturated with EtOAc/Hexanes to give pure 4,4-dimethyl-N-(5-(1-piperazinyl)-2-pyridinyl)spiro[cyclohexane-1,5'-pyrido[3',3':5,6]pyrano[3,4-d]pyrimidin]-3'-amine (66) (80 mg, 98% yield) (93% y. in 2 steps) as an off-white solid. $^1$H NMR (500 MHz, DMSO-d$_6$) δ ppm 9.85 (1H, s), 9.06 (1H, s), 8.29 (1H, dd, J=7.6, 1.7 Hz), 8.11 (1H, dd, J=4.9, 2.0 Hz), 8.03 (1H, d, J=9.3 Hz), 8.00 (1H, d, J=2.9 Hz), 7.40 (1H, dd, J=9.2, 3.1 Hz), 7.12 (1H, dd, J=7.6, 4.9 Hz), 3.00-3.09 (4H, m), 2.82-2.90 (4H, m), 2.09-2.19 (2H, m), 1.81 (2H, d, J=13.4 Hz), 1.66-1.77 (2H, m), 1.30 (2H, d, J=13.0 Hz), 1.01 (6H, d, J=2.0 Hz). LCMS-ESI (POS), M/Z, M+1: Found 458.0.

Example 28

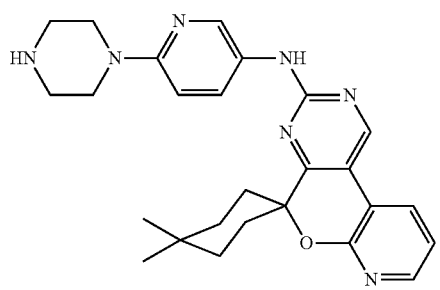

69

4,4-dimethyl-N-(6-(1-piperazinyl)-3-pyridinyl)spiro[cyclohexane-1,5'-pyrido[3',3':5,6]pyrano[3,4-d]pyrimidin]-3'-amine (tri-TFA salt)

Title compound (69) was prepared from compound (58) using chemistry similar to that described in Example 27. $^1$H NMR (400 MHz, MeOH-d4) (taken as a TFA salt) δ ppm 8.97 (1H, s), 8.75 (1H, d, J=2.7 Hz), 8.35 (1H, dd, J=7.8, 1.6 Hz), 8.17 (1H, dd, J=9.4, 2.7 Hz), 8.13 (1H, dd, J=5.3, 1.8 Hz), 7.19-7.27 (2H, m), 3.80-3.90 (4H, m), 3.38-3.45 (4H, m), 2.18-2.34 (2H, m), 1.81-1.99 (4H, m), 1.35 (2H, d, J=13.7 Hz), 1.06 (6H, d, J=2.7 Hz). LCMS-ESI (POS), M/Z, M+1: Found 458.2.

Example 29

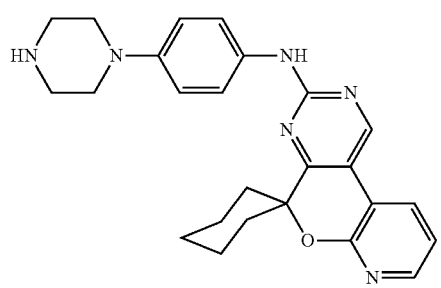

70

N-(4-(1-piperazinyl)phenyl)spiro[cyclohexane-1,5'-pyrido[3',2':5,6]pyrano[3,4-d]pyrimidin]-3'-amine Title compound (70) was prepared using chemistry similar to that described in Examples 26 and 27. $^1$H NMR (400 MHz, DMSO-d$_6$) δ ppm 9.67 (1H, s), 9.00 (1H, s), 8.26 (1H, dd, J=7.8, 2.0 Hz), 8.10 (1H, dd, J=4.9, 1.8 Hz), 7.59 (2H, d, J=9.0 Hz), 7.11 (1H, dd, J=7.4, 5.1 Hz), 6.89 (2H, d, J=9.4 Hz), 2.95-3.03 (4H, m), 2.79-2.87 (4H, m), 1.20-1.97 (10H, m). LCMS-ESI (POS), M/Z, M+1: Found 429.2.

Example 30

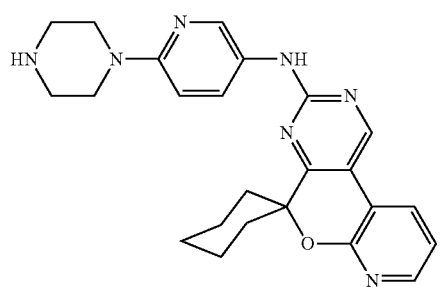

71

N-(6-(1-piperazinyl)-3-pyridinyl)spiro[cyclohexane-1,5'-pyrido[3',3':5,6]pyrano[3,4-d]pyrimidin]-3'-amine Title compound (71) was prepared using chemistry similar to that described in Example 26 and 27. $^1$H NMR (400 MHz, DMSO-d$_6$) δ ppm 9.67 (1H, s), 8.99 (1H, s), 8.45 (1H, d, J=2.7 Hz), 8.26 (1H, dd, J=7.6, 1.8 Hz), 8.10 (1H, dd, J=4.9, 1.8 Hz), 7.87 (1H, dd, J=9.4, 2.7 Hz), 7.11 (1H, dd, J=7.6, 4.9

Hz), 6.81 (1H, d, J=9.0 Hz), 3.31-3.35 (4H, m), 2.74-2.83 (4H, m), 1.26-1.96 (10H, m). LCMS-ESI (POS), M/Z, M+1: Found 430.1.

Example 31

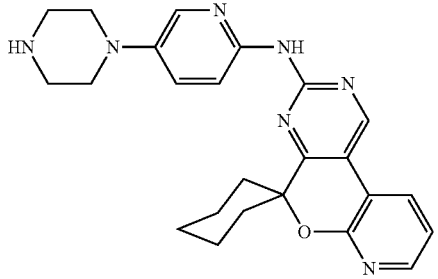

N-(5-(1-piperazinyl)-2-pyridinyl)spiro[cyclohexane-1,5'-pyrido[3',3':5,6]pyrano[3,4-d]pyrimidin]-3'-amine Title compound (72) was prepared using chemistry similar to that described in Examples 26 and 27. $^1$H NMR (500 MHz, DMSO-d$_6$) δ ppm 10.61 (1H, br. s.), 9.13 (1H, s), 8.86 (2H, br. s.), 8.37 (1H, dd, J=7.6, 1.7 Hz), 8.17 (1H, dd, J=4.9, 1.7 Hz), 8.07 (1H, d, J=2.9 Hz), 7.96 (1H, d, J=9.0 Hz), 7.77 (1H, dd, J=9.4, 2.6 Hz), 7.16 (1H, dd, J=7.6, 4.9 Hz), 3.35-3.42 (4H, m), 3.23-3.32 (4H, m), 1.89-2.00 (4H, m), 1.72-1.86 (3H, m), 1.64 (2H, br d, J=9.3 Hz), 1.25-1.42 (1H, m). LCMS-ESI (POS), M/Z, M+1: Found 430.1.

Example 32

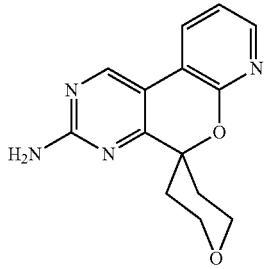

2,3,5,6-tetrahydrospiro[pyran-4,5'-pyrido[3',3':5,6]pyrano[3,4-d]pyrimidin]-3'-amine The title compound (73) was prepared using chemistry similar to that described in Example 26. $^1$H NMR (400 MHz, DMSO-d$_6$) δ ppm 8.87 (1H, s), 8.22 (1H, dd, J=7.4, 2.0 Hz), 8.08 (1H, dd, J=4.9, 1.8 Hz), 7.05-7.13 (3H, m), 3.72-3.85 (4H, m), 2.09-2.23 (2H, m), 1.75 (2H, d, J=12.1 Hz). LCMS-ESI (POS), M/Z, M+1: Found 271.1.

Example 33

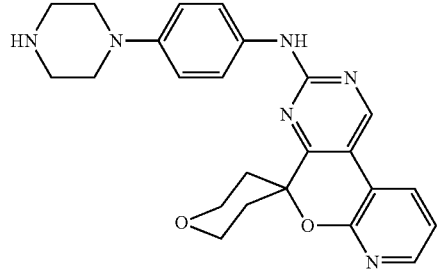

N-(4-(1-piperazinyl)phenyl)-2,3,5,6-tetrahydrospiro[pyran-4,5'-pyrido[3',2':5,6]pyrano[3,4-d]pyrimidin]-3'-amine Title compound (74) was prepared from compound (73) using chemistry similar to that described in Example 27. $^1$H NMR (400 MHz, DMSO-d$_6$) δ ppm 9.74 (1H, br. s.), 9.03 (1H, s), 8.29 (1H, dd, J=7.6, 1.8 Hz), 8.12 (1H, dd, J=4.9, 1.8 Hz), 7.59 (2H, d, J=9.0 Hz), 7.14 (1H, dd, J=7.6, 4.9 Hz), 6.91 (2H, d, J=9.4 Hz), 3.78-3.89 (4H, m), 2.95-3.04 (4H, m), 2.76-2.86 (4H, m), 2.16-2.28 (2H, m), 1.76-1.88 (2H, m). LCMS-ESI (POS), M/Z, M+1: Found 431.2

Example 34

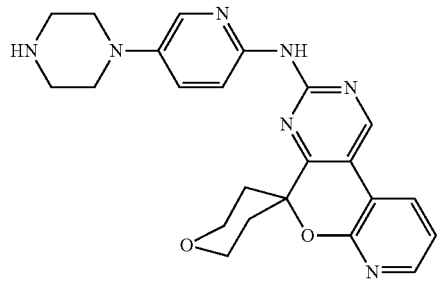

N-(5-(1-piperazinyl)-2-pyridinyl)-2,3,5,6-tetrahydrospiro[pyran-4,5'-pyrido[3',3':5,6]pyrano[3,4-d]pyrimidin]-3'-amine Title compound (75) was prepared from compound (73) using chemistry similar to that described in Example 27. $^1$H NMR (400 MHz, DMSO-d$_6$) δ ppm 9.90 (1H, s), 9.09 (1H, s), 8.33 (1H, dd, J=7.8, 2.0 Hz), 8.14 (1H, dd, J=4.9, 1.8 Hz), 7.97-8.06 (2H, m), 7.46 (1H, dd, J=9.0, 3.1 Hz), 7.16 (1H, dd, J=7.4, 5.1 Hz), 3.79-3.90 (4H, m), 3.00-3.09 (4H, m), 2.79-

Example 35

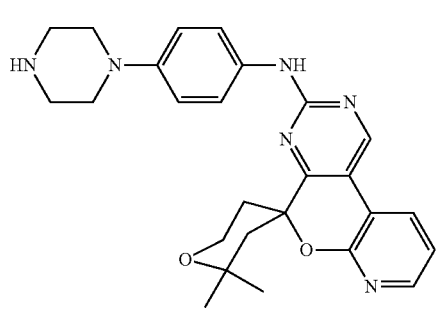

(racemic)-2,2-dimethyl-N-(4-(1-piperazinyl)phenyl)-2,3,5,6-tetrahydrospiro[pyran-4,5'-pyrido[3',2':5,6]pyrano[3,4-d]pyrimidin]-3'-amine Title compound (76) was prepared using chemistry similar to that described in Examples 26 and 27. $^1$H NMR (400 MHz, DMSO-d$_6$) δ ppm 9.73 (1H, s), 9.03 (1H, s), 8.29 (1H, dd, J=7.6, 1.8 Hz), 8.13 (1H, dd, J=4.9, 1.8 Hz), 7.58 (2H, d, J=9.0 Hz), 7.14 (1H, dd, J=7.4, 4.7 Hz), 6.90 (2H, d, J=9.4 Hz), 4.00-4.13 (1H, m), 3.73 (1H, dd, J=11.7, 3.9 Hz), 2.91-3.03 (4H, m), 2.78-2.88 (4H, m), 2.26-2.37 (1H, m), 1.79-1.90 (3H, m), 1.45 (3H, s), 1.12 (3H, s). LCMS-ESI (POS), M/Z, M+1: Found 459.2.

Example 36

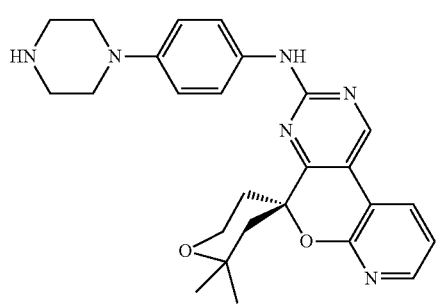

(4S)-2,2-dimethyl-N-(4-(1-piperazinyl)phenyl)-2,3,5,6-tetrahydrospiro[pyran-4,5'-pyrido[3',3':5,6]pyrano[3,4-d]pyrimidin]-3'-amine or

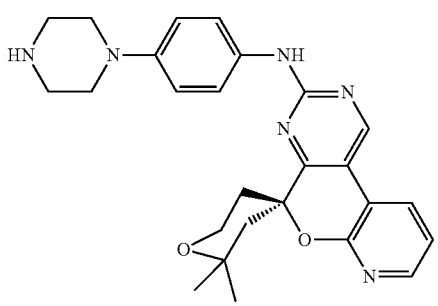

(4R)-2,2-dimethyl-N-(4-(1-piperazinyl)phenyl)-2,3,5,6-tetrahydrospiro[pyran-4,5'-pyrido[3',3':5,6]pyrano[3,4-d]pyrimidin]-3'-amine Title compound (77) was prepared using chemistry similar to that described in Example 26 and 27. $^1$H NMR (500 MHz, DMSO-d6) δ 9.83 (1H, s), 9.06 (1H, s), 8.76 (2H, br s), 8.32 (1H, dd, J1=7.8 Hz, J2=2.0 Hz), 8.15 (1H, dd, J1=4.8 Hz, J2=1.9 Hz), 7.66 (2H, br d, J=9.1 Hz), 7.16 (1H, dd, J1=7.6, J2=4.9 Hz), 7.00 (2H, br d, J=9.1 Hz), 4.09 (1H, dt, J1=12.4 Hz, J2=1.7 Hz), 3.74 (1H, ddd, J1=11.7 Hz, J2=5.4 Hz, J3=1.5 Hz), 3.30 (4H, m), 3.26 (4H, m), 2.33 (1H, ddd, J1=13.5 Hz, J2=14.2 Hz, J3=5.4 Hz), 1.87 (3H, m), 1.46 (3H, s), 1.13 (3H, s). LCMS-ESI (POS), M/Z, M+1: Found 459.2.

Example 37

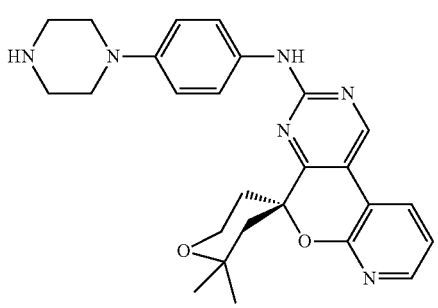

(4R)-2,2-dimethyl-N-(4-(1-piperazinyl)phenyl)-2,3,5,6-tetrahydrospiro[pyran-4,5'-pyrido[3',3':5,6]pyrano[3,4-d]pyrimidin]-3'-amine or

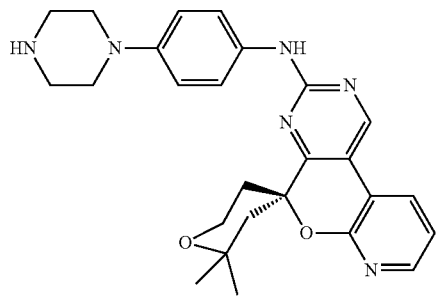

77

(4S)-2,2-dimethyl-N-(4-(1-piperazinyl)phenyl)-2,3,5,6-tetrahydrospiro[pyran-4,5'-pyrido[3',3':5,6]pyrano[3,4-d]pyrimidin]-3'-amine Title compound (78) was prepared using chemistry similar to that described in Example 26 and 27. $^1$H NMR (500 MHz, DMSO-d6) δ 9.82 (1H, s), 9.05 (1H, s), 8.73 (2H, br s), 8.30 (1H, dd, J1=7.6 Hz, J2=1.7 Hz), 8.14 (1H, dd, J1=4.9 Hz, J2=1.9 Hz), 7.65 (2H, br d, J=9.1 Hz), 7.14 (1H, dd, J1=7.3 Hz, J2=4.7 Hz), 6.99 (2H, br d, J=9.0 Hz), 4.07 (1H, dt, J1=11.9, J2=1.7 Hz), 3.73 (1H, ddd, J1=11.3 Hz, J2=5.4 Hz, J3=1.2 Hz), 3.29 (4H, m), 3.25 (4H, m), 2.23 (1H, ddd, J1=13.4 Hz, J2=14.5 Hz, J3=5.7 Hz), 1.83 (3H, m), 1.45 (3H, s), 1.12 (3H, s); LCMS-ESI (POS), M/Z, M+1: Found 459.2.

Example 38

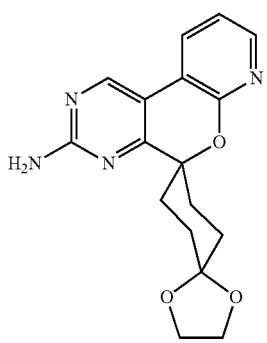

79 dispiro[1,3-dioxolane-2,1'-cyclohexane-4',5''-pyrido[3',3':5,6]pyrano[3,4-d]pyrimidin]-3''-amine The title compound (79) was prepared using chemistry similar to that described in Examples 26 and 27. $^1$H NMR (400 MHz, DMSO-d$_6$) δ ppm 8.84 (1H, s), 8.20 (1H, dd, J=7.8, 2.0 Hz), 8.06 (1H, dd, J=4.9, 1.8 Hz), 6.99-7.12 (3H, m), 3.91 (4H, s), 2.11-2.23 (2H, m), 1.80-1.99 (4H, m), 1.57-1.70 (2H, m). LCMS-ESI (POS), M/Z, M+1: Found 327.1

Example 39

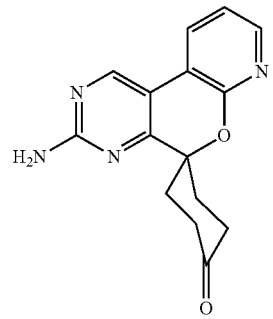

80

3'-amino-4H-spiro[cyclohexane-1,5'-pyrido[3',3':5,6]pyrano[3,4-d]pyrimidin]-4-one

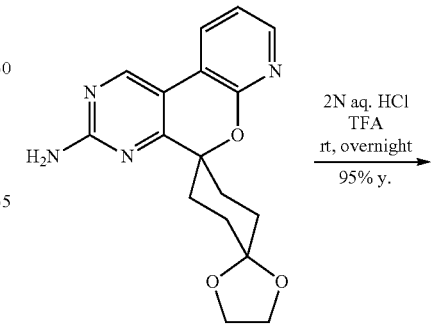

79

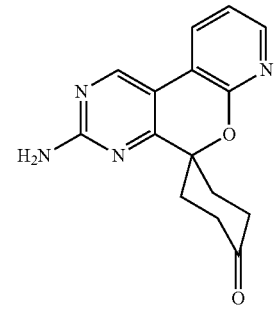

80

3'-Amino-4H-spiro[cyclohexane-1,5'-pyrido[3',2':5,6]pyrano[3,4-d]pyrimidin]-4-one (80) A solution of di-spiro[1,3-dioxolane-2,1'-cyclohexane-4',5''-pyrido[3',3':5,6]pyrano[3,4-d]pyrimidin]-3''-amine (79) (0.50 g, 1.5 mmol) in THF (40 mL) and HCl, (2N aqueous, 20 mL, 20 mmol) was stirred at rt overnight. Upon workup, the mixture was poured into ice and 2 N NaOH aqueous solution and saturated NaHCO$_3$ aqueous solution and extracted with EtOAc (3×). The combined organics were washed with brine (2×), dried over Na$_2$SO$_4$, and concentrated in vacuo. The residue was triturated with EtOAc/Hexanes to give 3'-amino-4H-spiro[cyclohexane-1,5'-pyrido[3',3':5,6]pyrano[3,4-d]pyrimidin]-4-one

(80) (0.41 g, 95% yield) as a yellow solid. ¹H NMR (400 MHz, DMSO-d₆) δ ppm 8.90 (1H, s), 8.26 (1H, dd, J=7.4, 2.0 Hz), 8.10 (1H, dd, J=4.9, 1.8 Hz), 7.14 (1H, dd, J=7.6, 4.9 Hz), 7.09 (2H, br. s.), 2.63-2.78 (2H, m), 2.12-2.42 (4H, m). LCMS-ESI (POS), M/Z, M+1: Found 283.0.

Example 40

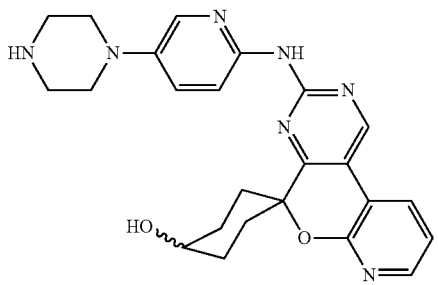

3'-β5-(1-piperazinyl)-2-pyridinyl)amino)spiro[cyclohexane-1,5'-pyrido[3',2':5,6]pyrano[3,4-d]pyrimidin]-4-ol Title compound (81) was prepared from (82) using chemistry similar to that described in Example 27. ¹H NMR (500 MHz, DMSO-d₆) δ ppm 9.82 (1H, s), 9.06 (1H, s), 8.30 (1 H, dd, J=7.6, 2.0 Hz), 8.13 (1H, dd, J=4.9, 1.7 Hz), 7.97-8.05 (2H, m), 7.44 (1H, dd, J=9.0, 3.2 Hz), 7.13 (1H, dd, J=7.6, 4.9 Hz), 4.72 (1H, d, J=4.4 Hz), 3.48-3.59 (1H, m), 3.03-3.07 (4H, m), 2.81-2.88 (4H, m), 1.92-2.06 (4H, m), 1.64-1.80 (4H, m). LCMS-ESI (POS), M/Z, M+1: Found 446.2. (Note: The product is a 4.4:1 mixture of 2 stereoisomers based on reverse phase HPLC. The ¹H NMR data reported is for the major isomer).

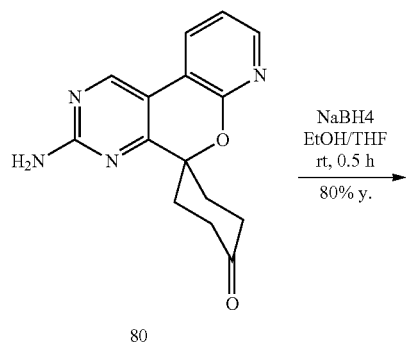

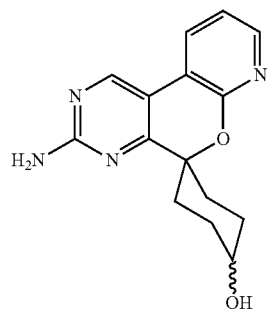

3'-Aminospiro[cyclohexane-1,5'-pyrido[3',3':5,6]pyrano[3,4-d]pyrimidin]-4-ol (82) Sodium borohydride (0.022 ml, 0.64 mmol) was added in one portion to a stirred suspension of 3'-amino-4H-spiro[cyclohexane-1,5'-pyrido[3',3':5,6]pyrano[3,4-d]pyrimidin]-4-one (80) (0.18 g, 0.64 mmol) in a mixed solvent EtOH/THF (13 mL/5 mL) at rt. The resulting mixture was stirred at rt for 0.5 h. Upon workup, the mixture was poured into ice and saturated NaHCO₃ aqueous solution and extracted with EtOAc (3×). The combined organics were washed with brine (1×), dried over Na₂SO₄, and concentrated in vacuo to give 3'-aminospiro[cyclohexane-1,5'-pyrido[3',3':5,6]pyrano[3,4-d]pyrimidin]-4-ol (82) (0.15 g, 80% yield) as an orange solid. ¹H NMR (500 MHz, DMSO-d₆) δ ppm 8.83 (1H, s), 8.19 (1H, dd, J=7.5, 1.8 Hz), 8.06 (1H, dd, J=4.9, 1.7 Hz), 7.08 (1H, dd, J=7.5, 5.0 Hz), 7.02 (2H, br. s.), 4.69 (1H, d, J=4.6 Hz), 3.43-3.56 (1H, m), 1.82-1.98 (4H, m), 1.64-1.77 (4H, m). LCMS-ESI (POS), M/Z, M+1: Found 285.0.

Example 41

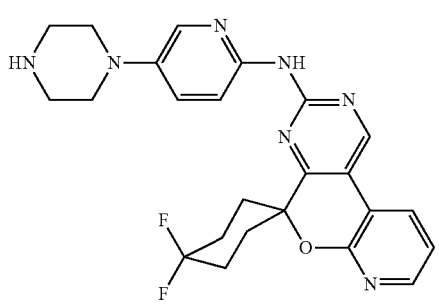

4,4-difluoro-N-(5-(1-piperazinyl)-2-pyridinyl)spiro[cyclohexane-1,5'-pyrido[3',3':5,6]pyrano[3,4-d]pyrimidin]-3'-amine Title compound (83) was prepared from (87) using chemistry similar to that described in Examples 26 and 27. ¹H NMR (400 MHz, DMSO-d₆) δ ppm 11.68 (1H, br. s.), 9.60 (2H, br. s.), 9.25 (1H, s), 8.51 (1H, dd, J=7.8, 2.0 Hz), 8.25 (1H, dd, J=4.9, 1.8 Hz), 8.14 (1H, dd, J=9.4, 2.7 Hz), 8.05 (1H, d, J=2.7 Hz), 7.82 (1H, d, J=9.4 Hz), 7.26 (1H, dd, J=7.6, 4.9 Hz), 3.39-3.57 (4H, m), 3.25 (4H, br. s.), 2.03-2.37 (8H, m). LCMS-ESI (POS), M/Z, M+1: Found 466.1

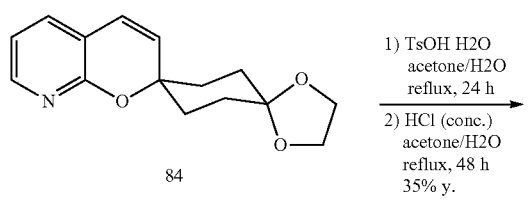

1) TsOH H2O
acetone/H2O
reflux, 24 h

2) HCl (conc.)
acetone/H2O
reflux, 48 h
35% y.

84

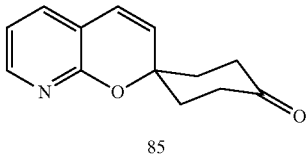

85

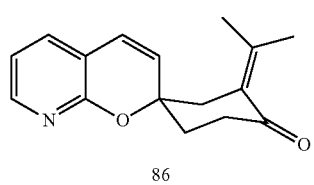

86

4H-Spiro[cyclohexane-1,2'-pyrano[2,3-b]pyridin]-4-one (85) A solution of dispiro[1,3-dioxolane-2,1'-cyclohexane-4', 2"-pyrano[2,3-b]pyridine] (84) (1.0 g, 3.9 mmol) and p-toluenesulfonic acid monohydrate (3.7 g, 19 mmol) in acetone (50 mL) and H₂O (2 mL) was refluxed for 18 h. Concentrated HCl (4 mL) was added and refluxing was continued for another 24 h till the reaction showed completion by HPLC. Upon workup, the reaction mixture was poured into ice and a mixture of saturated NaHCO₃ aqueous solution and 2 N NaOH aqueous solution and extracted with EtOAc (2×). The combined organics were washed with saturated NaHCO₃ aqueous solution (1×) followed by brine (1×), dried over Na₂SO₄, and concentrated in vacuo. The residue was subjected to combi-flash column chromatography (1$^{st}$ column, MeOH/DCM) to give a side product, 3-(1-methylethylidene)-4H-spiro[cyclohexane-1,2'-pyrano[2,3-b]pyridin]-4-one (86) (0.20 g, 20% yield) as a bright yellow solid. The fast eluting fractions from the 1st column were combined, concentrated in vacuo, and the residue was purified on another run of combi-flash column chromatography (2$^{nd}$ column, EtOAc/Hexanes) to give the desired 4H-spiro[cyclohexane-1,2'-pyrano[2,3-b]pyridin]-4-one (85) (0.29 g, 35% yield) as an off-white crystalline solid. ¹H NMR (500 MHz, CHLOROFORM-d) δ ppm 8.08 (1H, dd, J=5.0, 1.8 Hz), 7.35 (1H, dd, J=7.2, 1.8 Hz), 6.90 (1H, dd, J=7.3, 5.1 Hz), 6.44 (1H, d, J=9.8 Hz), 5.67 (1H, d, J=9.5 Hz), 2.94-3.09 (2H, m), 2.43-2.53 (2H, m), 2.27-2.36 (2H, m), 1.90-2.01 (2H, m). LCMS-ESI (POS), M/Z, M+1: Found 216.1

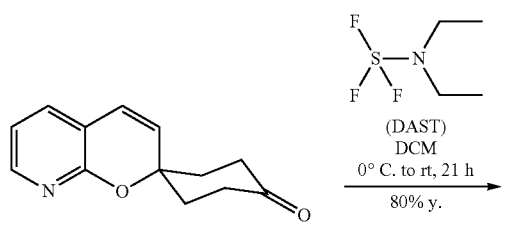

(DAST)
DCM
0° C. to rt, 21 h
80% y.

85

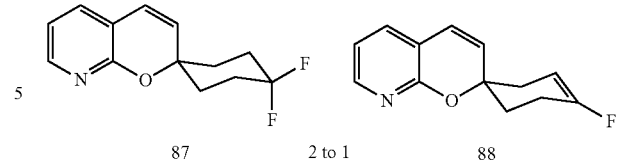

87        2 to 1        88

4,4-Difluorospiro[cyclohexane-1,2'-pyrano[2,3-b]pyridine] (87) DAST (0.36 ml, 2.7 mmol) was added to a stirred ice-cooled solution of 4H-spiro[cyclohexane-1,2'-pyrano[2,3-b]pyridin]-4-one (85) (0.29 g, 1.3 mmol) in DCM (30 mL) under N₂. The resulting mixture was allowed to warm up to rt and stirred at ambient temperature for 21 h. The mixture was poured into ice and saturated NaHCO₃ aqueous solution and extracted with DCM (2×). The combined organics were washed with brine, dried over Na₂SO₄, and concentrated in vacuo to give a 2; 1 mixture of 4,4-difluorospiro[cyclohexane-1,2'-pyrano[2,3-b]pyridine] (87) and 4-fluorospiro[cyclohex-3-ene-1,2'-pyrano[2,3-b]pyridine] (88) (0.25 g, 80% yield). This material was taken onto the next step without separation. LCMS-ESI (POS), M/Z, M+1: Found 238.1.

Example 42

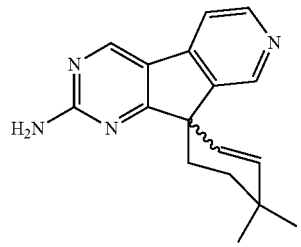

89

(racemic)-4,4-dimethylspiro[cyclohex-2-ene-1,9'-pyrido[4',3':3,4]cyclopenta[1,2-d]pyrimidin]-2'-amine

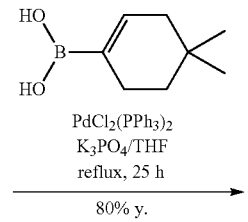

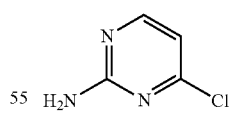

PdCl₂(PPh₃)₂
K₃PO₄/THF
reflux, 25 h
80% y.

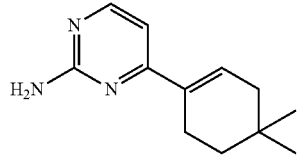

90

4-(4,4-Dimethylcyclohex-1-enyl)pyrimidin-2-amine (90) A 25 mL single-necked RBF was charged with 4-chloropyrimidin-2-amine (0.80 g, 6.2 mmol), 4,4-dimethylcyclohex- 1-enylboronic acid (1.0 g, 6.5 mmol), trans-dichlorobis(triphenyl-phosphine)palladium (ii) (0.14 g, 0.19 mmol), and tripotassium phosphate (1.4 g, 6.5 mmol). The flask was then subjected to 3 cycles of evacuation and back-filling with $N_2$ before THF (10 mL) was added under $N_2$. The resulting mixture was heated at reflux for 25 h. Upon workup, the mixture was poured into ice and saturated $NaHCO_3$ aqueous solution and extracted with EtOAc (3×). The combined organics were washed with brine (1×), dried over $Na_2SO_4$, and concentrated in vacuo. The residue was purified by combi-flash column chromatography (EtOAc/Hexanes) to give 4-(4,4-dimethylcyclohex-1-enyl)pyrimidin-2-amine (90) (1.0 g, 80% yield) as an off-white solid. $^1$H NMR (400 MHz, DMSO-$d_6$) δ ppm 8.14 (1H, d, J=5.1 Hz), 6.73-6.79 (1H, m), 6.66 (1H, d, J=5.1 Hz), 6.38 (2H, br. s.), 2.30-2.40 (2H, m), 1.96-2.05 (2H, m), 1.44 (2H, t, J=6.5 Hz), 0.92 (6H, s). LCMS-ESI (POS), M/Z, M+1: Found 204.1.

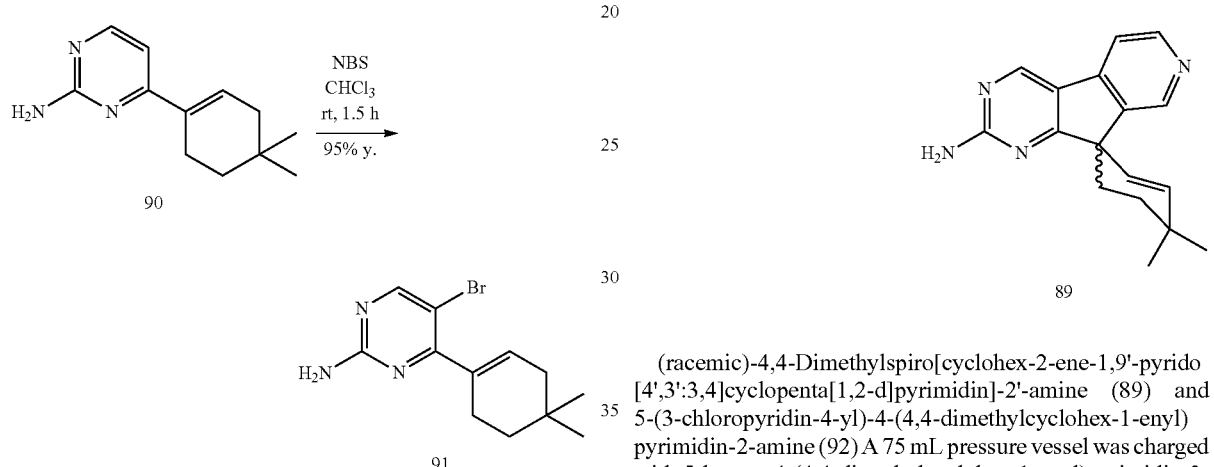

5-Bromo-4-(4,4-dimethylcyclohex-1-enyl)pyrimidin-2-amine (91) N-bromosuccinimide (482 mg, 2706 μmol) was added to a stirred solution of 4-(4,4-dimethylcyclohex-1-enyl)pyrimidin-2-amine (90) (0.55 g, 2706 μmol) in $CHCl_3$ (5 mL) and stirred at rt for 1.5 h. The crude mixture was purified by combi-flash column chromatography (EtOAc/Hexanes) to give 5-bromo-4-(4,4-dimethylcyclohex-1-enyl)pyrimidin-2-amine (91) (790 mg) as an off-white solid. $^1$H NMR (400 MHz, CHLOROFORM-d) δ ppm 8.31 (1H, s), 5.92-6.09 (1H, m), 5.17 (2H, br. s.), 2.28-2.46 (2H, m), 1.92-2.06 (2H, m), 1.51 (2H, t, J=6.5 Hz), 1.01 (6H, s). LCMS-ESI (POS), M/Z, M+1: Found 282.0.

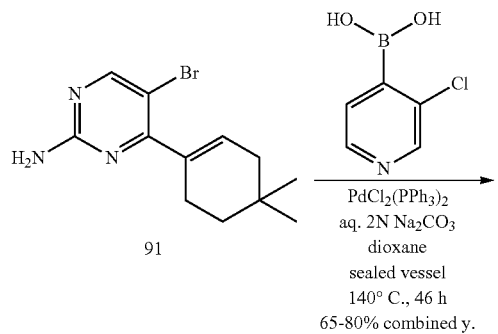

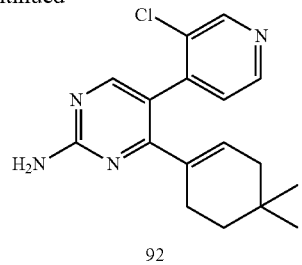

(racemic)-4,4-Dimethylspiro[cyclohex-2-ene-1,9'-pyrido[4',3':3,4]cyclopenta[1,2-d]pyrimidin]-2'-amine (89) and 5-(3-chloropyridin-4-yl)-4-(4,4-dimethylcyclohex-1-enyl)pyrimidin-2-amine (92) A 75 mL pressure vessel was charged with 5-bromo-4-(4,4-dimethylcyclohex-1-enyl)pyrimidin-2-amine (91) (0.64 g, 2.3 mmol), 3-chloropyridin-4-ylboronic acid (1.2 g, 7.9 mmol), and trans-dichlorobis(triphenyl-phosphine)palladium (ii) (0.48 g, 0.68 mmol) and 1,4-dioxane (40 mL). The mixture was stirred and purged with $N_2$ for 5 min Sodium carbonate (2 M aq. solution, 7.9 ml, 16 mmol) was then introduced and purging with $N_2$ continued for another 5 min. The vessel was sealed and heated at 140° C. for 46 h. After cooling, the mixture was filtered through a layer of Celite. The filter cake was thoroughly washed with EtOAc and $H_2O$, Saturated $NaHCO_3$ aqueous solution was added to the filtrate and the layers were separated. The aqueous layer was extracted with EtOAc (1×). The combined organic layer was washed with 2 N HCl aqueous solution (2×). The combined aqueous layer was extracted with EtOAc (1×), then basified with ice cold 4 N NaOH aqueous solution, and extracted with EtOAc (2×). The combined organics were dried over $Na_2SO_4$ and concentrated in vacuo. The residue after concentration in vacuo was purified by combi-flash column chromatography (EtOAc/Hexanes) to give the major product, 5-(3-chloropyridin-4-yl)-4-(4,4-dimethylcyclohex-1-enyl)pyrimidin-2-amine (92) (0.47 g, 66% yield) as an off-white solid. $^1$H NMR (400 MHz, CHLOROFORM-d) δ ppm 8.67 (1H, s), 8.54 (1H, d, J=4.7 Hz), 8.16 (1H, s), 7.20 (1H, d, J=5.5 Hz), 5.71-5.81 (1H, m), 2.26-2.39 (2H, m), 1.70-1.81 (2H, m), 1.42 (2H, t, J=6.5 Hz), 0.86 (6H, s). LCMS-ESI (POS), M/Z, M+1: Found 315.1. As a side product, (racemic)-4,4-dimethylspiro[cyclohex-2-ene-1,9'-pyrido[4',3':3,4]cyclopenta[1,2-d]pyrimidin]-2'-amine (89) (0.035 g, 5.5% yield) was obtained as a light yellow solid.

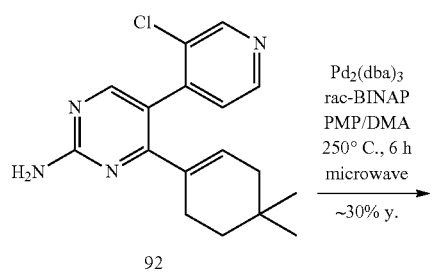

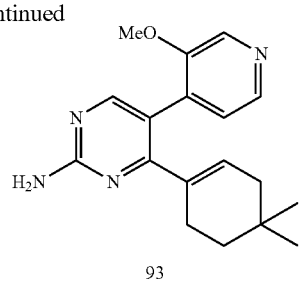

4-(4,4-Dimethylcyclohex-1-enyl)-5-(3-methoxypyridin-4-yl)pyrimidin-2-amine (93) A 75 mL pressure vessel was charged with 3-methoxypyridin-4-ylboronic acid (2.93 g, 19.1 mmol) and trans-dichlorobis(triphenyl-phosphine)palladium (ii) (0.448 g, 0.638 mmol) followed by a solution of 5-bromo-4-(4,4-dimethylcyclohex-1-enyl)pyrimidin-2-amine (91) (1.80 g, 6.38 mmol) in 1,4-dioxane (50 mL). The mixture was purged with $N_2$ for 5 min and sodium carbonate, 2 M aq. solution (22.3 ml, 44.7 mmol) was introduced. Purging with $N_2$ continued for another 5 min. The vessel was sealed and heated at 135° C. for 22 h. Upon workup, the mixture was poured into saturated $NaHCO_3$ aqueous solution and extracted with EtOAc (2×). The combined organics were dried over $Na_2SO_4$ and concentrated in vacuo. The residue was purified by combi-flash column chromatography (MeOH/DCM) to give 4-(4,4-dimethylcyclohex-1-enyl)-5-(3-methoxypyridin-4-yl)pyrimidin-2-amine (93) (1.56 g, 78.8% yield) as an off-white solid. $^1$H NMR (400 MHz, CHLOROFORM-d) δ ppm 8.25-8.31 (2H, m), 8.14 (1H, s), 7.11 (1H, d, J=4.7 Hz), 5.54-5.62 (1H, m), 5.08 (2H, br. s.), 3.85 (3H, s), 2.24-2.34 (2H, m), 1.69-1.74 (2H, m), 1.39 (2H, t, J=6.3 Hz), 0.85 (6H, s). LCMS-ESI (POS), M/Z, M+1: Found 311.2.

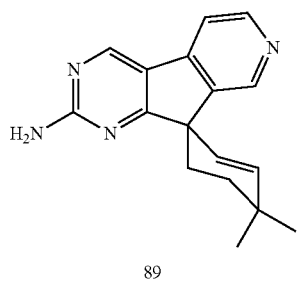

(racemic)-4,4-Dimethylspiro[cyclohex-2-ene-1,9'-pyrido[4',3':3,4]cyclopenta[1,2-d]pyrimidin]-2'-amine (89) A microwave reaction vessel was charged with tris(dibenzylideneacetone)dipalladium (o) (99 mg, 0.11 mmol), 2-(diphenylphosphino)-1-(2-(diphenylphosphino)naphthalen-1-yl) naphthalene (134 mg, 0.22 mmol) and a solution of 5-(3-chloropyridin-4-yl)-4-(4,4-dimethylcyclohex-1-enyl)pyrimidin-2-amine (92) (85 mg, 0.27 mmol) in DMA (3.6 mL). The vessel was purged with $N_2$ for 3 min before 1,2,2,6,6-pentamethylpiperidine (244 μl, 1.35 mmol) was introduced. After purging with $N_2$ for 3 min, the vessel was capped and subjected to microwave condition (6 h at 250° C.). The mixture was filtered through a layer of Celite and concentrated to dryness. The residue was purified by combi-flash column chromatography (MeOH/DCM) to give (racemic)-4,4-dimethylspiro[cyclohex-2-ene-1,9'-pyrido[4',3':3,4]cyclopenta[1,2-d]pyrimidin]-2'-amine (89) (54 mg, 72% yield) as an off-white solid. $^1$H NMR (400 MHz, MeOH-d4) (taken as a TFA salt) δ ppm 9.01 (1H, s), 8.59-8.65 (2H, m), 8.20 (1H, dd, J=6.1, 1.0 Hz), 6.03 (1H, d, J=9.8 Hz), 5.13 (1H, d, J=9.8 Hz), 2.13-2.27 (2H, m), 1.72-1.96 (2H, m), 1.24 (6H, d, J=7.0 Hz). LCMS-ESI (POS), M/Z, M+1: Found 279.1.

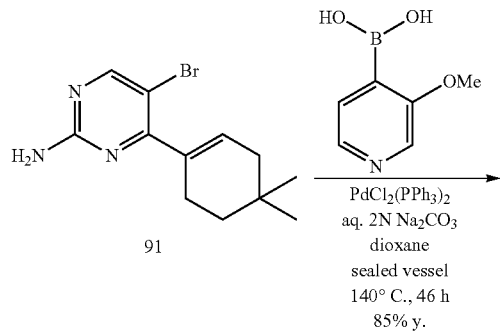

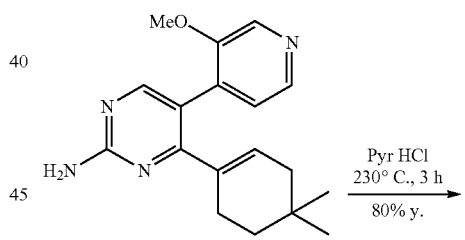

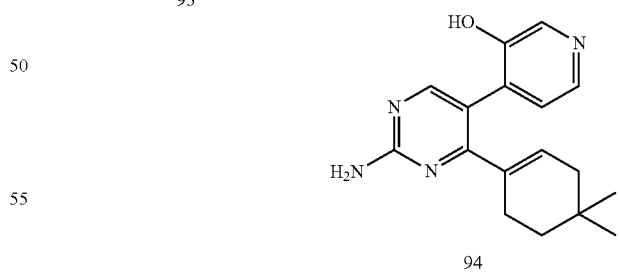

4-(2-Amino-4-(4,4-dimethylcyclohex-1-enyl)pyrimidin-5-yl)pyridin-3-ol (94) A mixture of 4-(4,4-dimethylcyclohex-1-enyl)-5-(3-methoxypyridin-4-yl)pyrimidin-2-amine (93) (0.24 g, 0.77 mmol) and pyridine hydrochloride (0.72 g, 6.2 mmol) was stirred in an oil bath at 235° C. for 3 h. After cooling, the crude solid was taken up by saturated $NH_4Cl$ aqueous solution and EtOAc. After the layers were separated, the aqueous was extracted with EtOAc (1×). The aqueous layer was basified with ice cold saturated NaHCO₃ aqueous solution and extracted with 10% i-PrOH/chloroform (3×). The organic layers were combined, dried over Na₂SO₄, and concentrated in vacuo to give 4-(2-amino-4-(4,4-dimethylcyclohex-1-enyl)pyrimidin-5-yl)pyridin-3-ol (94) (0.18 g, 79% yield) as an off-white solid. ¹H NMR (500 MHz, MeOH-d4) δ ppm 8.13 (1H, s), 8.07 (1H, s), 8.02 (1H, d, J=4.9 Hz), 7.19 (1H, d, J=4.9 Hz), 5.51-5.56 (1H, m), 2.34-2.40 (2H, m), 1.65-1.72 (2H, m), 1.41 (2H, t, J=6.4 Hz), 0.87 (6H, s). LCMS-ESI (POS), M/Z, M+1: Found 297.1.

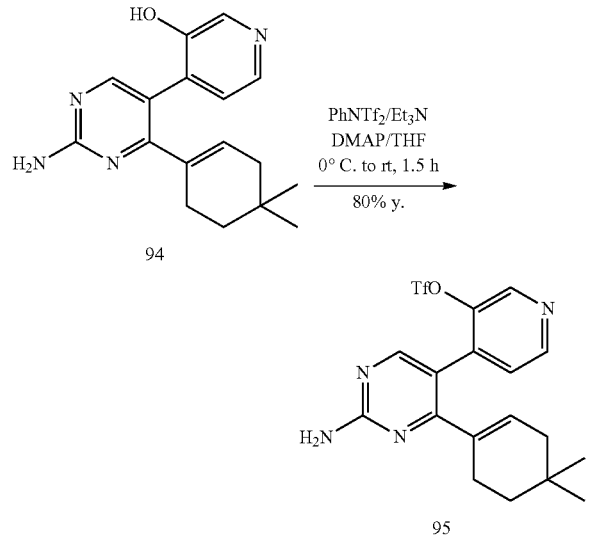

4-(2-Amino-4-(4,4-dimethylcyclohex-1-enyl)pyrimidin-5-yl)pyridin-3-yl trifluoromethanesulfonate (95) N-phenyltriflimide (0.36 g, 1.0 mmol) was added to a stirred ice-cooled solution of 4-(2-amino-4-(4,4-dimethylcyclohex-1-enyl)pyrimidin-5-yl)pyridin-3-ol (94) (0.10 g, 0.34 mmol), triethylamine (0.19 ml, 1.3 mmol) and 4-(dimethylamino)pyridine (catalytic amount) in THF (12 mL) and at 0° C. for 5 min and then at rt for 1.5 h. The mixture was concentrated in vacuo without heating and purified by combi-flash column chromatography (EtOAc/Hexanes) to give 4-(2-amino-4-(4,4-dimethylcyclohex-1-enyl)pyrimidin-5-yl)pyridin-3-yl trifluoromethanesulfonate (95) (0.11 g, 76% yield) as a nearly colorless crystalline solid. ¹H NMR (400 MHz, CHLOROFORM-d) δ ppm 8.64 (1H, d, J=4.7 Hz), 8.57 (1H, s), 8.17 (1H, s), 7.36 (1H, d, J=5.1 Hz), 5.47-5.53 (1H, m), 5.43 (2H, br. s.), 2.39 (2H, br. s.), 1.67-1.73 (2H, m), 1.42 (2H, t, J=6.3 Hz), 0.87 (6H, s). LCMS-ESI (POS), M/Z, M+1: Found 429.1.

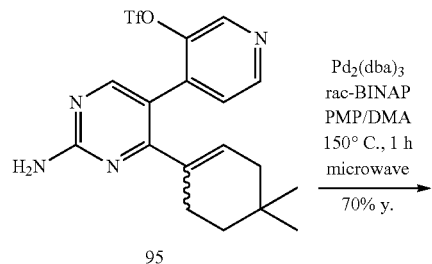

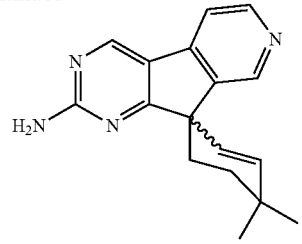

(racemic)-4,4-Dimethylspiro[cyclohex-2-ene-1,9'-pyrido[4',3':3,4]cyclopenta[1,2-d]pyrimidin]-2'-amine (89) A microwave reactor vessel was charged with tris(dibenzylideneacetone)dipalladium (o) (0.062 g, 0.068 mmol), 2-(diphenylphosphino)-1-(2-(diphenylphosphino)naphthalen-1-yl)naphthalene (0.084 g, 0.14 mmol) and a solution of 4-(2-amino-4-(4,4-dimethylcyclohex-1-enyl)pyrimidin-5-yl)pyridin-3-yl trifluoromethanesulfonate (95) (0.29 g, 0.68 mmol) in DMA (3.5 mL). The vessel was purged with N₂ for 3 min before 1,2,2,6,6-pentamethylpiperidine (0.61 ml, 3.4 mmol) was introduced via a syringe. After purging with N₂ for another 3 min, the vessel was capped and subjected to microwave condition (1 h at 150° C.). The crude product mixture was filtered through a layer of Celite. The filtrate was concentrated in vacuo and purified by combi-flash column chromatography (MeOH/DCM) to give (racemic)-4,4-dimethylspiro[cyclohex-2-ene-1,9'-pyrido[4',3':3,4]cyclopenta[1,2-d]pyrimidin]-2'-amine (89) (0.13 g, 69% yield) as an off-white solid.

Example 43

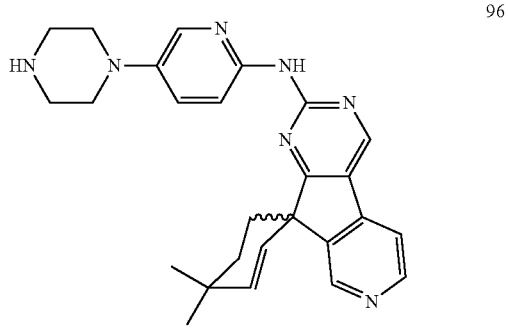 [SMILES: CC1(C)C=CC2(CC1)c1cnccc1-c1cnc(Nc3ccc(N4CCNCC4)cn3)nc12]

(racemic)-4,4-dimethyl-N-(5-(1-piperazinyl)-2-pyridinyl)spiro[cyclohex-2-ene-1,9'-pyrido[4',3':3,4]cyclopenta[1,2-d]pyrimidin]-2'-amine Title compound (96) was prepared from compound (89) using chemistry similar to that described in Example 27. ¹H NMR (500 MHz, MeOH) (taken as a TFA salt) δ ppm 9.37 (1H, s), 8.84 (1H, s), 8.79 (1H, d, J=6.1 Hz), 8.42 (1H, d, J=5.9 Hz), 7.97-8.07 (2H, m), 7.86 (1H, d, J=9.3 Hz), 6.11 (1H, d, J=9.8 Hz), 5.20 (1H, d, J=9.8 Hz), 3.50-3.55 (4H, m), 3.42-3.47 (4H, m), 2.18-2.32 (2H, m), 1.99-2.08 (1H, m), 1.81-1.90 (1H, m), 1.29 (6H, d, J=3.4 Hz). LCMS-ESI (POS), M/Z, M+1: Found 440.2.

Example 44

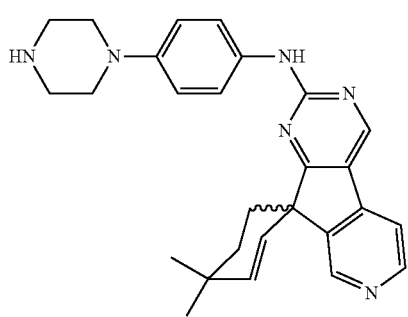

97

(racemic)-4,4-dimethyl-N-(4-(1-piperazinyl)phenyl) spiro[cyclohex-2-ene-1,9'-pyrido[4',3':3,4]cyclopenta[1,2-d]pyrimidin]-2'-amine Title compound (97) was prepared from compound (89) using chemistry similar to that described in Example 27. $^1$H NMR (400 MHz, MeOH) (taken as a TFA salt) δ ppm 9.12 (1H, s), 8.61-8.71 (2H, m), 8.24 (1H, d, J=6.3 Hz), 7.74 (2H, d, J=9.0 Hz), 7.04 (2H, d, J=9.0 Hz), 6.08 (1H, d, J=9.8 Hz), 5.17 (1H, d, J=9.8 Hz), 3.40 (8H, s), 1.64-2.45 (4H, m), 1.28 (6H, d, J=2.0 Hz) LCMS-ESI (POS), M/Z, M+1: Found 439.1.

Example 45

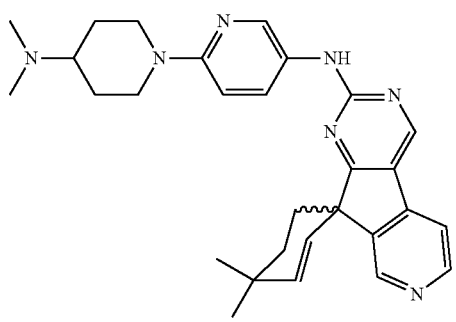

98

(racemic)-N-(6-(4-(dimethylamino)-1-piperidinyl)-3-pyridinyl)-4,4-dimethylspiro[cyclohex-2-ene-1,9'-pyrido[4',3':3,4]cyclopenta[1,2-d]pyrimidin]-2'-amine Title compound (98) was prepared from compound (89) using chemistry similar to that described in Example 27. $^1$H NMR (400 MHz, MeOH-d4) (taken as a TFA salt) δ ppm 9.20 (1H, s), 8.54-8.80 (3H, m), 8.31 (1H, d, J=6.3 Hz), 8.20 (1H, dd, J=9.4, 2.7 Hz), 7.26 (1H, br. s.), 6.07 (1H, d, J=9.8 Hz), 5.17 (1H, d, J=9.8 Hz), 4.41 (2H, d, J=13.7 Hz), 3.50-3.59 (1H, m), 3.09-3.21 (2H, m), 2.91 (6H, s), 1.69-2.33 (8H, m), 1.26 (6H, d, J=6.7 Hz). LCMS-ESI (POS), M/Z, M+1: Found 482.2.

Example 46

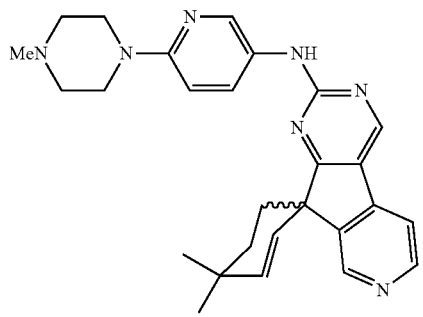

99

(racemic)-4,4-dimethyl-N-(6-(4-methyl-1-piperazinyl)-3-pyridinyl)spiro[cyclohex-2-ene-1,9'-pyrido[4',3':3,4]cyclopenta[1,2-d]pyrimidin]-2'-amine Title compound (99) was prepared from (89) using chemistry similar to that described in Example 27. $^1$H NMR (400 MHz, MeOD-d3) (taken as a TFA salt) δ ppm 9.16 (1H, s), 8.66-8.75 (2H, m), 8.61 (1H, d, J=2.7 Hz), 8.29 (1H, d, J=5.5 Hz), 8.12 (1H, dd, J=9.0, 2.7 Hz), 7.03 (1H, d, J=9.4 Hz), 6.08 (1H, d, J=9.8 Hz), 5.17 (1H, d, J=9.8 Hz), 4.29 (4H, br. s.), 3.61 (4H, s), 2.99 (3H, s), 1.65-2.46 (4H, m), 1.27 (6H, d, J=7.4 Hz). LCMS-ESI (POS), M/Z, M+1: Found 454.3.

Example 47

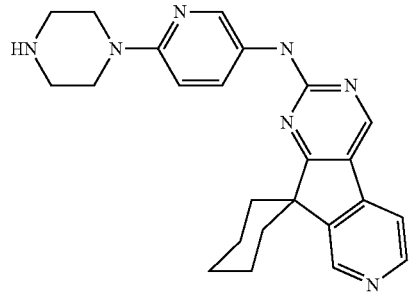

100

N-(6-(1-piperazinyl)-3-pyridinyl)spiro[cyclohexane-1,9'-pyrido[4',3':3,4]cyclopenta[1,2-d]pyrimidin]-2'-amine Title compound (100) was prepared from compound (104) using chemistry similar to that described in Example 27. $^1$H NMR (500 MHz, DMSO-d6) δ 10.34 (1H, br s), 9.28 (1H, s), 9.13 (1H, s), 8.83 (2H, br s), 8.82 (1H, d, J=5.9 Hz), 8.57 (1H, br s), 8.33 (1H, d, J=6.1 Hz), 8.05 (1H, br s), 7.01 (1H, d, J=8.8 Hz), 3.68 (4H, m), 3.21 (4H, m), 2.15 (2H, m), 1.85 (2H, m), 1.75 (6H, m); LCMS-ESI (POS), M/Z, M+1: Found 414.2.

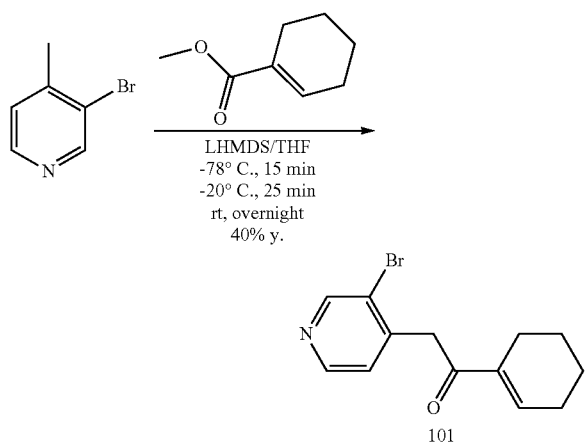

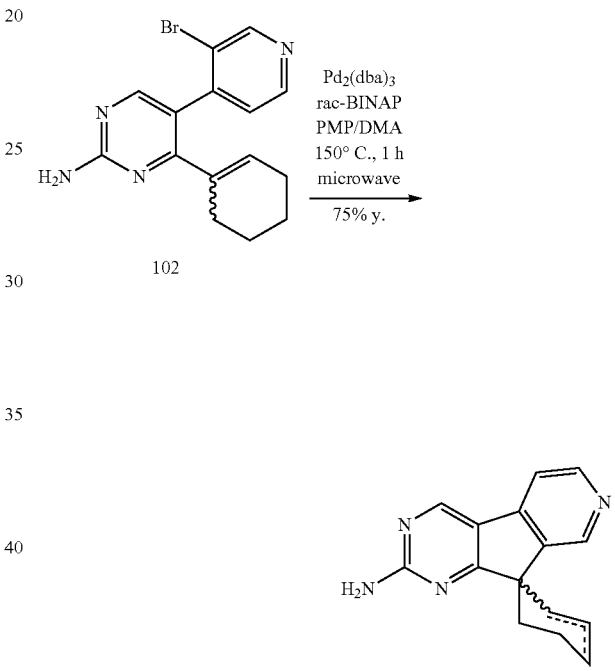

2-(3-Bromopyridin-4-yl)-1-cyclohexenylethanone (101) Lithium bis(trimethylsilyl)amide (1M solution in THF) (21 ml, 21 mmol) was added over a period of 5 min to a stirred solution of 3-bromo-4-methylpyridine (3.0 g, 17 mmol) in THF (15 mL) cooled in an acetone-dry ice bath. The resulting mixture was stirred for 10 min before the acetone-dry ice bath was replaced with ice-salt bath (−20° C.). Stirring continued for another 20 min A solution of 1-(carbomethoxy)cyclohexene (3.3 ml, 24 mmol) in THF (15 mL) was added through a syringe at this temperature. The resulting mixture was allowed to slowly warm up to rt and stirred overnight. Upon workup, the mixture was poured onto ice and saturated $NH_4Cl$ aqueous solution and extracted with EtOAc (2×). The combined organics were dried over $Na_2SO_4$ and concentrated in vacuo. The residue was purified by combi-flash column chromatography (EtOAc/Hexanes) to give 2-(3-bromopyridin-4-yl)-1-cyclohexenylethanone (101) (2.0 g, 41% yield) as an off-white solid. $^1$H NMR (400 MHz, CHLOROFORM-d) δ ppm 8.71 (1H, s), 8.46 (1H, d, J=5.1 Hz), 7.17 (1H, d, J=4.7 Hz), 7.02-7.11 (1H, m), 4.13 (2H, s), 2.22-2.40 (4H, m), 1.55-1.77 (4H, m). LCMS-ESI (POS), M/Z, M+1: Found 280.0.

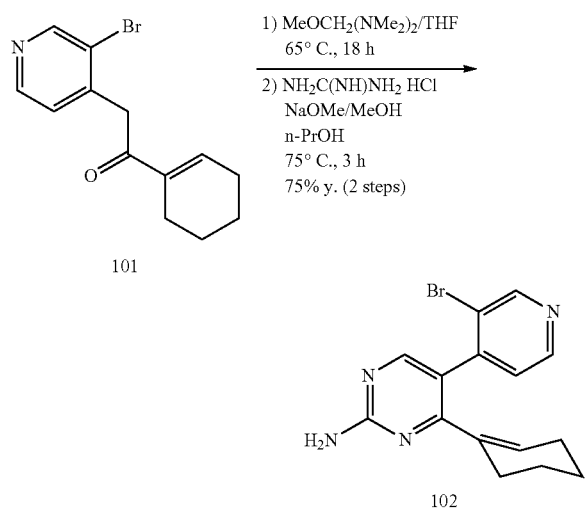

5-(3-Bromopyridin-4-yl)-4-cyclohexenylpyrimidin-2-amine (102) A solution of 2-(3-bromopyridin-4-yl)-1-cyclohexenylethanone (101) (0.64 g, 2.3 mmol) and methoxy-N,N',N'-tetramethylmethanediamine (1.7 ml, 11 mmol) in THF (2 mL) was stirred at 65° C. (oil bath) overnight Guanidine hydrochloride (2.2 g, 23 mmol), n-propanol (9 mL) and sodium methoxide (4.37 M solution in MeOH) (3.7 ml, 16 mmol) were added sequentially. The resulting mixture was stirred at 75° C. for 3 h. After cooling, the mixture was poured into ice and saturated $NaHCO_3$ aqueous solution and extracted with EtOAc (2 X). The combined organics were dried over $Na_2SO_4$ and concentrated in vacuo. The residue was purified by combi-flash column chromatography (MeOH/DCM) to give 5-(3-bromopyridin-4-yl)-4-cyclohexenylpyrimidin-2-amine (102) (0.57 g, 75% yield) as a light yellow solid. $^1$H NMR (400 MHz, MeOH-d4) δ ppm 8.73 (1H, s), 8.51 (1H, d, J=4.9 Hz), 8.07 (1H, s), 7.41 (1H, d, J=4.9 Hz), 5.55-5.61 (1H, m), 2.31-2.44 (2H, m), 1.90 (2H, br. s.), 1.62-1.72 (2H, m), 1.48-1.61 (2H, m). LCMS-ESI (POS), M/Z, M+1: Found 331.0.

Spiro[cyclohex-2-ene-1,9'-pyrido[4',3':3,4]cyclopenta[1,2-d]pyrimidin]-2'-amine and spiro[cyclohex-3-ene-1,9'-pyrido[4',3':3,4]cyclopenta[1,2-d]pyrimidin]-2'-amine (103) A microwave reactor vessel was charged with tris(dibenzylideneacetone)dipalladium (o) (26 mg, 0.03 mmol), 2-(diphenylphosphino)-1-(2-(diphenylphosphino)naphthalen-1-yl) naphthalene (36 mg, 0.06 mmol) and a solution of 5-(3-bromopyridin-4-yl)-4-cyclohexenylpyrimidin-2-amine (A) (95 mg, 0.29 mmol) in DMA (2.5 mL). The vessel was purged with $N_2$ for 3 min before 1,2,2,6,6-pentamethylpiperidine (0.26 ml, 1.4 mmol) was introduced via a syringe. After a nitrogen purge for 3 min, the vessel was capped and subjected to microwave condition (1 h at 150° C.). The crude was filtered through a layer of Celite and concentrated to dryness. The residue was purified by combi-flash column chromatography (MeOH/DCM) to give (103) (54 mg, 75% yield) as a 5:3 mixture of isomers, spiro[cyclohex-2-ene-1,9'-pyrido[4',3':3,4]cyclopenta[1,2-d]pyrimidin]-2'-amine and spiro[cyclohex-3-ene-1,9'-pyrido[4',3':3,4]cyclopenta[1,2-d]pyrimidin]-2'-amine. LCMS-ESI (POS), M/Z, M+1: Found 251.2.

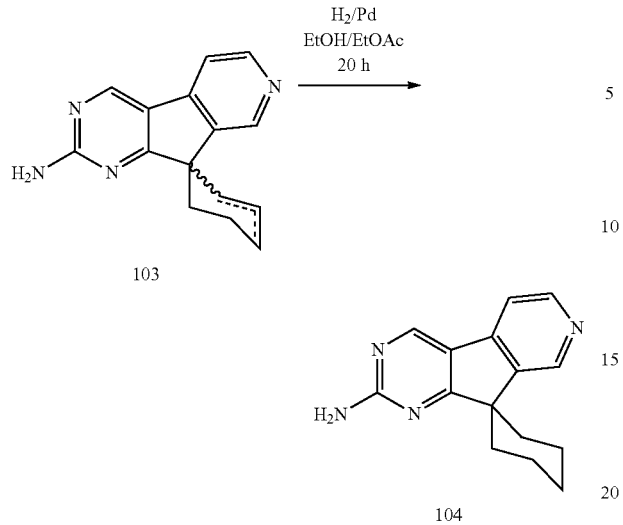

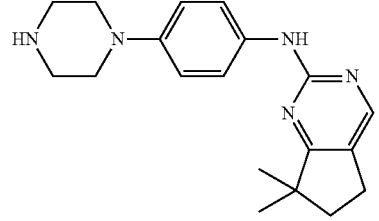

Spiro[cyclohexane-1,9'-pyrido[4',3':3,4]cyclopenta[1,2-d]pyrimidin]-2'-amine (104) The isomeric mixture (103) (90 mg) in a mixed solvent of EtOH (10 mL) and EtOAc (6 mL) was hydrogenated under one atmosphere of $H_2$ in the presence of palladium, (10 wt. % (dry basis) on activated carbon, ~1.9 mg, 18 µmol)) for a period of 20 h. The mixture was filtered through a layer of Celite and concentrated in vacuo to give spiro[cyclohexane-1,9'-pyrido[4',3':3,4]cyclopenta[1,2-d]pyrimidin]-2'-amine (104) (74 mg, 82% yield) as an off-white solid. $^1$H NMR (400 MHz, CHLOROFORM-d) δ ppm 8.91 (1H, s), 8.66 (1H, s), 8.56 (1H, d, J=5.1 Hz), 7.50 (1H, dd, J=5.1, 0.8 Hz), 5.53 (2H, br. s.), 1.55-2.15 (10H, m). LCMS-ESI (POS), M/Z, M+1: Found 253.1.

Example 48

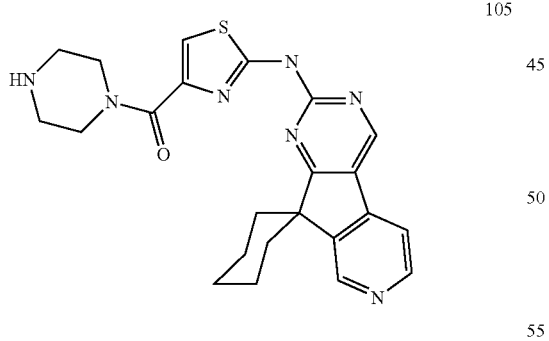

N-(4-(1-piperazinylcarbonyl)-1,3-thiazol-2-yl)spiro[cyclohexane-1,9'-pyrido[4',3':3,4]cyclopenta[1,2-d]pyrimidin]-2'-amine Title compound (105) was prepared from compound (104) using chemistry similar to that described in Example 27. $^1$H NMR (500 MHz, DMSO-d6) δ 9.10 (1H, s), 8.97 (1H, s), 8.90 (1H, s), 8.38 (1H, d, J=5.2 Hz), 8.05 (1H, s), 7.95 (1H, d, J=5.2 Hz), 6.73 (1H, s), 5.20 (1H, br s), 3.39 (4H, m), 2.80 (4H, m), 2.18 (2H, br s), 2.14 (2H, s), 1.98 (2H, br s), 1.81 (2H, br s), 1.59 (2H, br s), see rotamers present; LCMS-ESI (POS), M/Z, M+1: Found 448.1.

Example 49

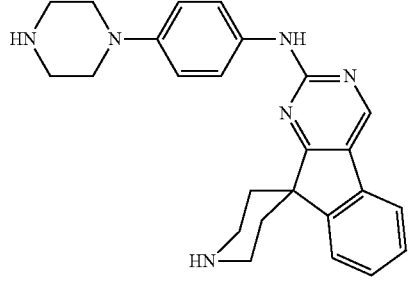

7,7-dimethyl-N-(4-(1-piperazinyl)phenyl)-6,7-dihydro-5H-cyclopenta[d]pyrimidin-2-amine Title compound (106) was prepared from 2,2-dimethylcyclopentanone using chemistry similar to that described in Examples 26 and 27. LCMS-ESI (POS), M/Z, M+1: Found 324.2.

Example 50

N-(4-(1-piperazinyl)phenyl)spiro[indeno[2,1-d]pyrimidine-9,4'-piperidin]-2-amine Title compound (107) was prepared from commercially available N—BOC-1-[4-Spiro-piperidine]-2-indanone using chemistry similar to that described in Examples 26 and 27. $^1$H NMR (400 MHz, DMSO-d$_6$) δ ppm 9.52 (1H, br. s.), 8.86 (1H, s), 7.53-7.82 (4H, m), 7.23-7.38 (2H, m), 6.89 (2H, d, J=8.6 Hz), 3.43-3.53 (2H, m), 2.91-3.07 (6H, m), 2.77-2.87

(4H, m), 1.75-1.86 (2H, m), 1.56-1.67 (2H, m). LCMS-ESI (POS), M/Z, M+1: Found 413.2.

Example 51

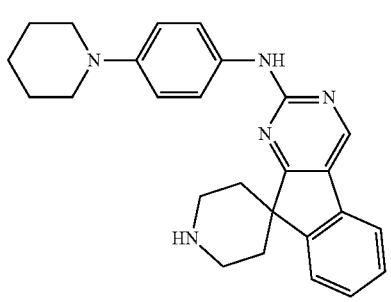

108

N-(4-(1-piperidinyl)phenyl)spiro[indeno[2,1-d]pyrimidine-9,4'-piperidin]-2-amine Title compound (108) was prepared from commercially available N—BOC-1-[4-Spiro-piperidine]-2-indanone using chemistry similar to that described in Example 3. $^1$H NMR (500 MHz, CDCl$_3$) δ 8.69 (1H, s), 7.55-7.65 (4H, m), 7.30-7.37 (2H, m), 7.18 (1H, s), 6.99 (2H, t, J=9.3 Hz), 3.77 (1H, br t, J=10), 3.47 (1H, br s), \3.31 (1H, br t, J=9.6 Hz), 3.18-3.22 (1H, m), 3.14 (2H, t, J=4.3), 3.10 (2H, t, J=5.4 Hz), 3.07 (1H, m), 2.17 (1H, br t, J=10.8 Hz), 2.07 (1H, br t, J=10.0 Hz), 1.85 (1H, br d, J=13.0 Hz), 1.72-1.77 (2H, m), 1.66-1.71 (2H, m), 1.56-1.60 (1H, m), 1.50-1.55 (1H, m); LCMS-ESI (POS), M/Z, M+1: Found 412.1

Example 52

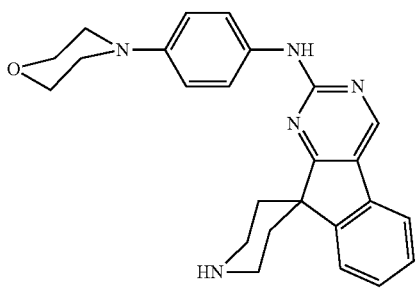

109

N-(4-(4-morpholinyl)phenyl)spiro[indeno[2,1-d]pyrimidine-9,4'-piperidin]-2-amine Title compound (109) was prepared from commercially available N—BOC-1-[4-Spiro-piperidine]-2-indanone using chemistry similar to that described in Example 3. $^1$H NMR (500 MHz, DMSO-d$_6$) δ ppm 9.66 (1H, s), 9.16 (1H, d, J=10.5 Hz), 8.95 (1H, s), 8.69 (1H, q, J=10.0 Hz), 7.82 (1H, d, J=7.3 Hz), 7.62 (2H, d, J=8.8 Hz), 7.47 (1H, d, J=7.6 Hz), 7.39-7.44 (1H, m), 7.34-7.39 (1H, m), 7.01 (2H, d, J=9.0 Hz), 3.79-3.90 (2H, m), 3.75-3.79 (4H, m), 3.47 (2H, d, J=12.7 Hz), 3.03-3.15 (4H, m), 2.25-2.36 (2H, m), 1.78 (2H, d, J=13.9 Hz); LCMS-ESI (POS), M/Z, M+1: Found 414.1

Example 53

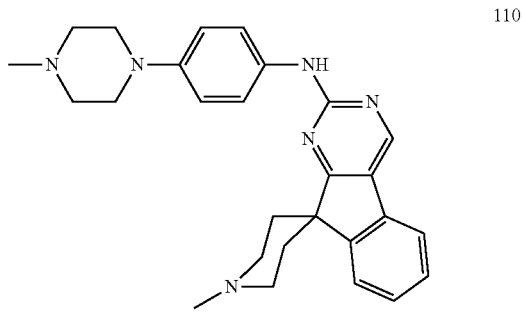 [SMILES: CN1CCN(c2ccc(Nc3ncc4c(n3)C3(CCN(C)CC3)c3ccccc3-4)cc2)CC1]

110

1'-methyl-N-(4-(4-methyl-1-piperazinyl)phenyl)spiro[indeno[2,1-d]pyrimidine-9,4'-piperidin]-2-amine Title compound (110) was prepared from compound 107 in Example 50 via bis-alkylation with methyl iodide. LCMS-ESI (POS), M/Z, M+1: Found 441.2

Example 54

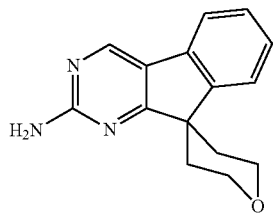

111

2',3',5',6'-tetrahydrospiro[indeno[2,1-d]pyrimidine-9,4'-pyran]-2-amine

Title compound (III) was prepared from compound 112 using chemistry similar to that described in Example 1. $^1$H NMR (400 MHz, DMSO-d$_6$) δ ppm 8.70 (1H, s), 7.70 (1H, d, J=7.4 Hz), 7.62 (1H, d, J=7.4 Hz), 7.28-7.36 (1H, m), 7.20-7.28 (1H, m), 6.83 (2H, br. s.), 4.32-4.45 (2H, m), 3.80-3.94 (2H, m), 1.88-2.03 (2H, m), 1.50-1.66 (2H, m) LCMS-ESI (POS), M/Z, M+1: Found 254.1

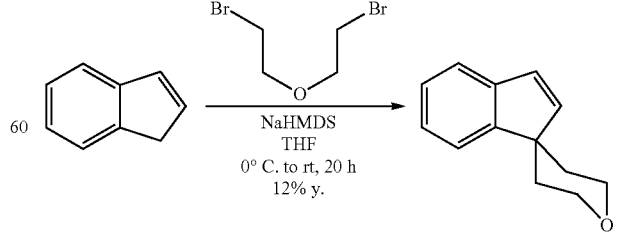

112

2',3',5',6'-Tetrahydrospiro[indene-1,4'-pyran] (112) An oven-dried 200 mL single-necked round bottom flask was charged with NaHMDS (1 M solution in THF) (67 mL, 67.2 mmol). The solution was stirred and cooled in an ice-H$_2$O bath while a solution of indene (3.7 g, 31.9 mmol) in THF (6 mL) was added under N$_2$ atmosphere. The resulting mixture was stirred at 0° C. for 2 h and then cannulated into a stirred, ice-cooled solution of 1-bromo-2-(2-bromoethoxy)ethane (7.4 g, 31.9 mmol) in THF (15 mL). The resulting mixture was stirred at 0° C. for 3 h and allowed to warm up to rt overnight. Upon workup, the reaction mixture was poured into ice and saturated NH$_4$Cl aqueous solution and extracted with EtOAc (2×). The combined organics were washed with brine (1×), dried over Na$_2$SO$_4$, and concentrated in vacuo. The residue was purified by combi-flash column chromatography (EtOAc/Hexanes) to give 2',3',5',6'-tetrahydrospiro[indene-1,4'-pyran] (112) (0.7 g, 12% yield) as an off-white solid. $^1$H NMR (400 MHz, CHLOROFORM-d) δ ppm 7.35-7.44 (2H, m), 7.22-7.32 (2H, m), 6.99 (1H, d, J=5.9 Hz), 6.82 (1H, d, J=5.5 Hz), 4.09-4.15 (2H, m), 3.82 (2H, td, J=11.9, 2.3 Hz), 2.24 (2H, td), 1.30-1.37 (2H, m).

Example 55

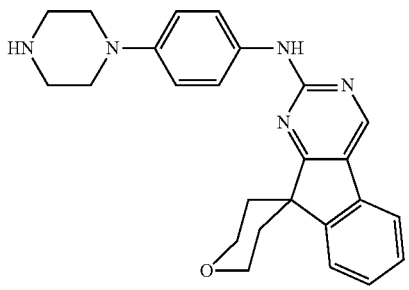

113

N-(4-(1-piperazinyl)phenyl)-2',3',5',6'-tetrahydrospiro[indeno[2,1-d]pyrimidine-9,4'-pyran]-2-amine Title compound (113) was prepared from compound III using chemistry similar to that described in Example 27. $^1$H NMR (400 MHz, DMSO-d$_6$) δ ppm 9.54 (1H, s), 8.88 (1H, s), 7.77 (1H, d, J=7.0 Hz), 7.58-7.70 (3H, m), 7.26-7.41 (2H, m), 6.89 (2H, d, J=9.0 Hz), 4.36-4.47 (2H, m), 3.85-3.96 (2H, m), 2.93-3.03 (4H, m), 2.77-2.88 (4H, m), 1.97-2.08 (2H, m), 1.62 (2H, d, J=12.9 Hz). LCMS-ESI (POS), M/Z, M+1: Found 414.1.

Example 56

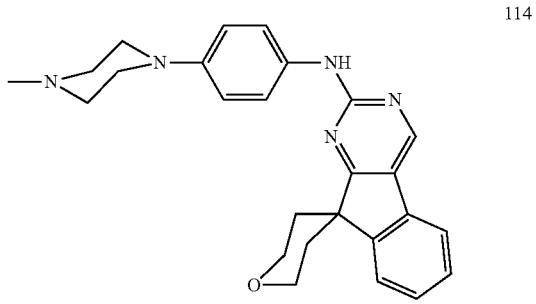 [SMILES: CN1CCN(c2ccc(Nc3ncc4c(n3)C3(CCOCC3)c3ccccc3-4)cc2)CC1]

114

N-(4-(4-methyl-1-piperazinyl)phenyl)-2',3',5',6'-tetrahydrospiro[indeno[2,1-d]pyrimidine-9,4'-pyran]-2-amine Title compound (114) was prepared from compound 112 using chemistry similar to that described in Examples 1 and 3. $^1$H NMR (500 MHz, DMSO-d$_6$) δ ppm 9.70 (1H, br. s.), 9.63 (1H, s), 8.91 (1H, s), 7.79 (1H, d, J=7.1 Hz), 7.74 (2H, d, J=9.0 Hz), 7.67 (1H, d, J=7.3 Hz), 7.38 (1H, dt, J=7.5, 1.0 Hz), 7.32 (1H, dt, J=7.5, 1.2 Hz), 7.01 (2H, d, J=9.3 Hz), 4.37-4.46 (2H, m), 3.93 (2H, dt, J=11.3, 4.2 Hz), 3.78 (2H, d, J=13.2 Hz), 3.54 (2H, d, J=12.0 Hz), 3.12-3.28 (2H, m), 2.93 (2H, t, J=12.1 Hz), 2.88 (3H, d, J=2.9 Hz), 2.04 (2H, ddd, J=13.8, 9.8, 4.3 Hz), 1.64 (2H, br d, J=13.4 Hz)); LCMS-ESI (POS), M/Z, M+1: Found 428.2.

Example 57

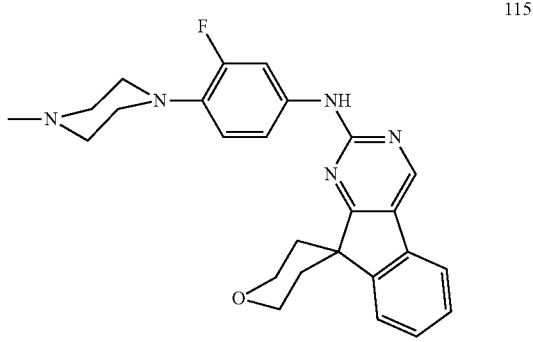 [SMILES: CN1CCN(c2ccc(Nc3ncc4c(n3)C3(CCOCC3)c3ccccc3-4)cc2F)CC1]

115

N-(3-fluoro-4-(4-methyl-1-piperazinyl)phenyl)-2',3',5',6'-tetrahydrospiro[indeno[2,1-d]pyrimidine-9,4'-pyran]-2-amine Title compound (115) was prepared from compound 112 using chemistry similar to that described in Example 1 and 3. $^1$H NMR (500 MHz, DMSO-d$_6$) δ ppm 9.90 (1H, s), 9.73 (1H, br. s.), 8.97 (1H, s), 7.87 (1H, dd, J=15.3, 2.3 Hz), 7.81 (1H, d, J=6.8 Hz), 7.68 (1H, d, J=7.3 Hz), 7.52 (1H, dd, J=8.8, 2.0 Hz), 7.39 (1H, ddd, J=7.5, 1.1 Hz), 7.34 (1H, ddd, J=7.5, 1.2

Hz), 7.06-7.14 (1H, m), 4.37-4.46 (2H, m), 3.94 (2H, dt, J=11.4, 4.2, 4.2 Hz), 3.52 (2H, d, J=12.2 Hz), 3.45 (2H, d, J=13.2 Hz), 3.23 (2H, q, J=10.7 Hz), 3.00 (2H, t, J=11.9 Hz), 2.88 (3H, d, J=3.4 Hz), 2.05 (2H, ddd, J=13.9, 10.0, 4.3 Hz), 1.64 (2H, br d, J=13.9 Hz); LCMS-ESI (POS), M/Z, M+1: Found 446.2

Example 58

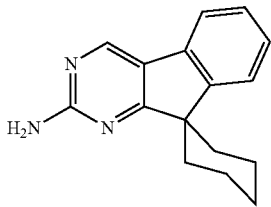

spiro[cyclohexane-1,9'-indeno[2,1-d]pyrimidin]-2'-amine

Title compound (116) was prepared from compound 117 using chemistry similar to that described in Example 1. $^1$H NMR (400 MHz, CHLOROFORM-d) δ ppm 8.59 (1H, s), 7.62 (2H, d, J=7.8 Hz), 7.34 (1H, td, J=7.4, 1.2 Hz), 7.28 (1H, td, J=7.5, 1.0 Hz), 5.25 (2H, br. s.), 2.06-2.19 (2H, m), 1.62-1.90 (8H, m). LCMS-ESI (POS), M/Z, M+1: Found 252.1

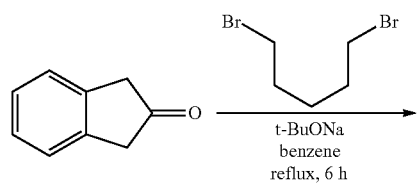

Spiro[cyclohexane-1,1'-inden]-2'(3'H)-one (117) 1,5-dibromopentane was added to a stirred solution of 2-indanone (7.0 g, 53.0 mmol) and) t-BuONa (12 g, 125 mmol) in benzene (60 mL) at rt. The resulting mixture was heated at reflux for 6 h. After cooling, the mixture was poured into ice and 2 N HCl aqueous solution and extracted with EtOAc (2×). The combined organic layer was washed with brine (2×), dried over Na$_2$SO$_4$, and concentrated in vacuo. The residue was subjected to combi-flash column chromatography (Et$_2$O/Hexanes) to give impure spiro[cyclohexane-1,1'-inden]-2'(3'H)-one (117) (0.32 g), which was used in the next step without further purification.

Example 59

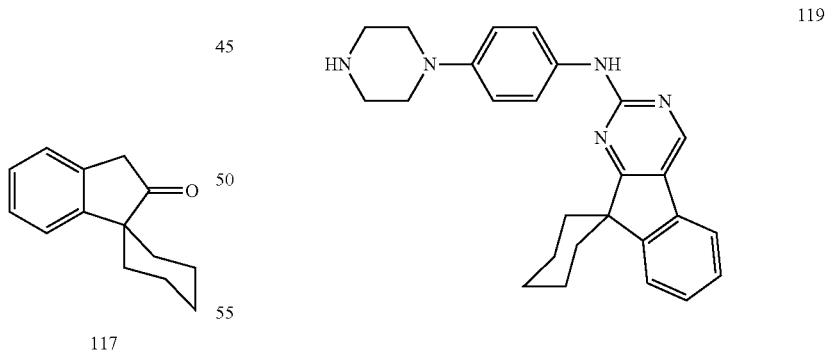

tert-butyl 4-(4-(spiro[cyclohexane-1,9'-indeno[2,1-d]pyrimidin]-2'-ylamino)phenyl)-1-piperazinecarboxylate Title compound (118) was prepared from compound 116 using chemistry similar to that described in Example 27. $^1$H NMR (400 MHz, CHLOROFORM-d) δ ppm 8.68 (1H, s), 7.54-7.66 (4H, m), 7.28-7.38 (2H, m), 7.13 (1H, br s), 6.98 (2H, d, J=8.8 Hz), 3.61-3.64 (4H, m), 3.11-3.13 (4H, m), 2.20-2.35 (2H, m), 1.70-1.90 (8H, m), 1.51 (9H, s). LCMS-ESI (POS), M/Z, M+1: Found 512.2

Example 60

N-(4-(1-piperazinyl)phenyl)spiro[cyclohexane-1,9'-indeno[2,1-d]pyrimidin]-2'-amine Title compound (119) was prepared from compound 118 using chemistry similar to that described in Example 27. $^1$H NMR (400 MHz, DMSO-d$_6$) δ ppm 9.51 (1H, s), 8.6 (1H, s), 7.76 (1H, d, J=7.3 Hz), 7.68 (2H, d, J=9.6 Hz), 7.62 (1H, d, J=7.3 Hz), 7.34 (1H, td, J=7.5, 1.0 Hz), 7.27 (1H, td, J=7.4, 1.2 Hz), 6.89 (2H, d, J=9.6 Hz), 2.97-3.00 (4H, m), 2.83-2.85

(4H, m), 2.23-2.33 (2H, m), 1.87 (1H, s), 1.60-1.80 (8H, m). LCMS-ESI (POS), M/Z, M+1: Found 412.1

Example 61

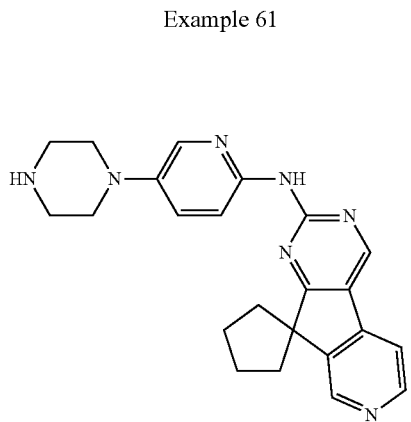

N-(5-(1-piperazinyl)-2-pyridinyl)spiro[cyclopentane-1,9'-pyrido[4',3':3,4]cyclopenta[1,2-d]pyrimidin]-2'-amine

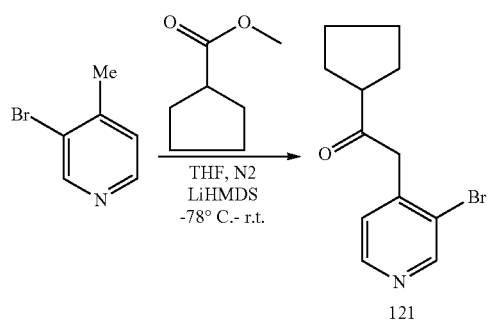

2-(3-Bromo-4-pyridinyl)-1-cyclopentylethanone (121) Under a nitrogen atmosphere LiHMDS (1.0M solution in tetrahydrofuran, 49.6 ml, 49.6 mmol) was added to a solution of methyl cyclopentanecarboxylate (3.630 g, 28.3 mmol) and 3-bromo-4-methylpyridine (2.62 ml, 23.6 mmol) in 10 ml of anhydrous THF over a period of 5 min at −78° C. After 10 min the solution was allowed to warm to 20° C. and stirred for 2 hours. The solution was then cooled in ice water, before the pH was adjusted to 4.5 with 25% citric acid. After extraction with DCM the organic layer was dried over Na$_2$SO$_4$ and then concentrated to afford 2-(3-bromo-4-pyridinyl)-1-cyclopentylethanone (121) (6.86 g, crude). $^1$H NMR (500 MHz, DMSO-d6) δ 8.68 (1H, s), 8.48 (1H, d, J=4.9 Hz), 7.37 (H, d, J=4.9 Hz), 4.07 (2H, s), 3.08 (1H, ddd, J1=16.1 Hz, J2=7.3 Hz, J3=1.2 Hz), 1.80-1.85 (2H, m), 1.72-1.77 (2H, m), 1.55-1.59 (4H, m); LCMS-ESI (POS), M/Z, M+1: Found 268.0

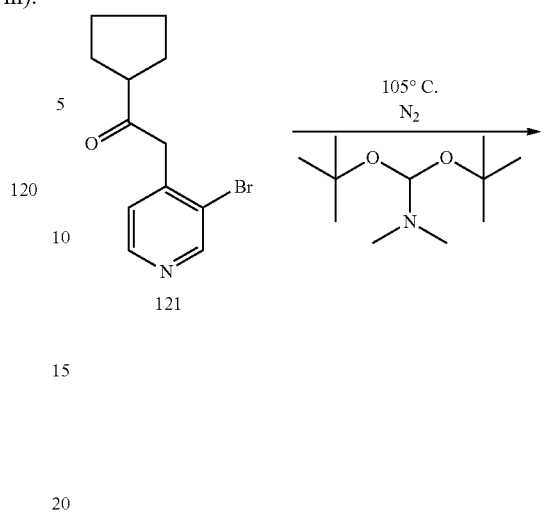

(2E)-2-(3-Bromo-4-pyridinyl)-1-cyclopentyl-3-(dimethylamino)-2-propen-1-one (122) Under an atmosphere of nitrogen a solution of 2-(3-bromo-4-pyridinyl)-1-cyclopentylethanone (121) (6.86 g, 25.9 mmol) and tert-butoxy-N,N,N',N'-tetramethylmethanediamine (7.31 ml) was heated at 105° C. for 3 hours. The reaction was then cooled to 20° C. and concentrated under vacuum. The residue was purified on a 120 g combiflash column (dry loaded), eluting with 100% EtOAc. The fractions containing the product were combined and concentrated under vacuum to give (2E)-2-(3-bromo-4-pyridinyl)-1-cyclopentyl-3-(dimethylamino)-2-propen-1-one (122) (5.79 g, 76%). $^1$H NMR (500 MHz, DMSO-d6) δ 8.68 (1H, s), 8.44 (1H, d, J=4.9 Hz), 7.64 (1H, s), 7.25 (1H, d, J=4.9 Hz), 2.71 (6H, br s), 1.40-1.72 (8H, m);); LCMS-ESI (POS), M/Z, M+1: Found 323.0.

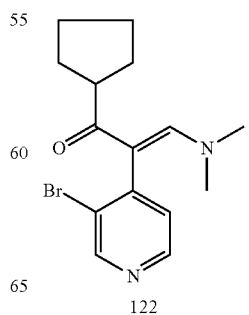

-continued

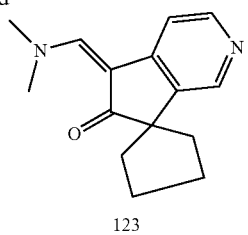
123

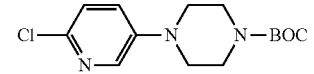
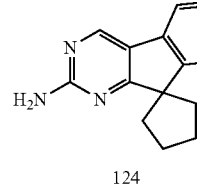
124

(3'Z)-3'4(Dimethylamino)methylidene)spiro[cyclopentane-1,1'-inden]-2'(3'H)-one (123) To a degassed solution of 2-(3-bromopyridin-4-yl)-1-cyclopentyl-3-(dimethylamino) prop-2-en-1-one (122) (4.738 g, 14.63 mmol) and sodium 2-methylpropan-2-olate (4.23 g, 44 mmol) in 20 ml of anhydrous toluene was added Pd2(dba)₃ (0.806 g, 0.879 mmol) and 2,8,9-triisobutyl-2,5,8,9-tetraaza-1-phospha-bicyclo [3.3.3]undecane (0.603 g, 1.757 mmol) under an atmosphere of nitrogen. The reaction was heated to 110° C. for 1.5 hours before it was cooled to 20° C. and concentrated under vacuum to give mainly (3'Z)-3'-((dimethylamino)methylidene)spiro [cyclopentane-1,1'-inden]-2'(3'H)-one (123). LCMS-ESI (POS), M/Z, M+1: Found 243.1.

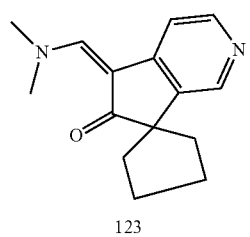
123

Guanidne HCl
215° C., N2

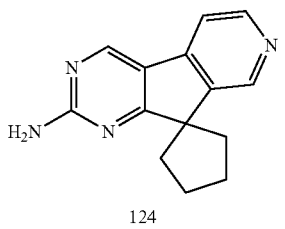
124

Spiro[cyclopentane-1,9'-pyrido[4',3':3,4]cyclopenta[1,2-d]pyrimidin]-2'-amine (124) A solution of (3'Z)-3'-((dimethylamino)methylidene)-spiro[cyclopentane-1,1'-inden]-2' (3'H)-one (123) (3.15 g, 14.63 mmol) and guanidine hydrochloride (14.0 g, 146 mmol) in 50 ml of iPrOH was heated at 215° C. and the solvent was allowed to distill off. After 5 minutes of heating the mixture was cooled to 20° C. 50 ml of H₂O was added and the solution was sonicated to break up the solids. After extraction with 10% iPrOH/DCM the organics were concentrated under vacuum. The residue was purified on an 80 g combiflash column (dry loaded), eluting with a gradient of DCM-6% MeOH/DCM. The fractions containing the product were combined and concentrated under vacuum. The residue obtained was triturated with Et2O and then with acetone to give, spiro[cyclopentane-1,9'-pyrido [4',3':3,4]cyclopenta[1,2-d]pyrimidin]-2'-amine (124) (0.824 g, 23%). ¹H NMR (500 MHz, DMSO-d6) δ 8.78 (1H, s), 8.63 (1H, d, J=1 Hz), 8.46 (1H, d, J=4.9 Hz), 7.65 (1H, dd, J1=4.9 Hz, J2=1.2 Hz), 7.11 (2H, br s), 2.05-2.10 (6H, m), 1.89-1.93 (2H, m); LCMS-ESI (POS), M/Z, M+1: Found 239.1.

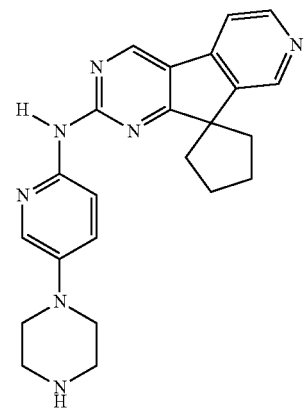
125

N-(5-(1-piperazinyl)-2-pyridinyl)spiro[cyclopentane-1, 9'-pyrido[4',3':3,4]cyclopenta[1,2-d]pyrimidin]-2'-amine (125) To a degassed solution of tert-butyl 4-(6-chloropyridin-3-yl)piperazine-1-carboxylate (0.12 g, 0.41 mmol), spiro[cyclopentane-1,9'-pyrido[4',3':3,4]cyclopenta[1,2-d]pyrimidin]-2'-amine (124) (0.081 g, 0.34 mmol), and sodium 2-methylpropan-2-olate (0.098 g, 1.0 mmol) in 4 ml of 1,4-Dioxane was added Pd2(dba)₃ (0.031 g, 0.034 mmol) and 4,5-bis(diphenylphosphino)-9,9-dimethyl-9H-xanthene (0.039 g, 0.068 mmol) under an atmosphere of nitrogen. The solution was heated to 120° C. with microwave irradiation for 1 hr. The solution was then purified on a 40 g combiflash column (dry loaded), eluting with a gradient of 40% EtOAc/ Hexane to EtOAc then with 2% MeOH/DCM to 5% MeOH/ DCM. The fractions containing the product were combined and concentrated under vacuum. The residue obtained was dissolved in 5 ml of DCM and 1 ml of TFA and stirred at room temperature for 2 hours. The organics were removed under vacuum to afford N-(5-(1-piperazinyl)-2-pyridinyl)spiro[cyclopentane-1,9'-pyrido[4',3':3,4]cyclopenta[1,2-d]pyrimidin]-2'-amine (125) (253 mg, 100%) as the TFA salt. ¹H NMR (400 MHz, DMSO-d6) δ 10.69 (1H, s), 9.31 (1H, s), 9.01 (1H, s), 8.60 (2H, br s), 8.83 (1H, d, J=6.2 Hz), 8.36 (1H, d, J=5.5 Hz), 8.12 (1H, d, J=3.2 Hz), 8.10 (1H, d, J=8.9 Hz), 7.63 (1H, dd, J1=9.4 Hz, J2=3.1 Hz), 3.39 (4H, m), 3.27 (4H, m), 2.12-2.20 (8H, m); LCMS-ESI (POS), M/Z, M+1: Found 400.1.

Example 62

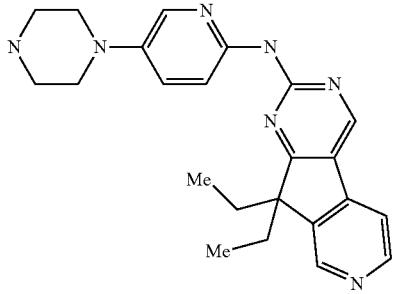

126

9,9-diethyl-N-(5-(1-piperazinyl)-2-pyridinyl)-9H-pyrido[4',3':3,4]cyclopenta[1,2-d]pyrimidin-2-amine Title compound (126) was prepared using chemistry similar to that described in Example 61. $^1$H NMR (400 MHz, DMSO-d6) δ 10.82 (1H, s), 9.34 (1H, s), 9.03 (1H, s), 8.88 (1H, d, J=5.9 Hz), 8.84 (2H, br s), 8.39 (1H, d, J=5.9 Hz), 8.13 (1H, d, J=3.2 Hz), 8.10 (1H, d, J=8.9 Hz), 7.65 (1H, d, J1=9.3 Hz, J2=3.1 Hz), 3.94 (4H, m), 3.28 (4H, m), 2.21 (2H, dq, J1=13.7 Hz, J2=7.4 Hz), 2.12 (2H, dq, J1=13.7 Hz, J2=7.0 Hz), 0.38 (6H, t, J=7.4 Hz)); LCMS-ESI (POS), M/Z, M+1: Found 402.2.

Example 63

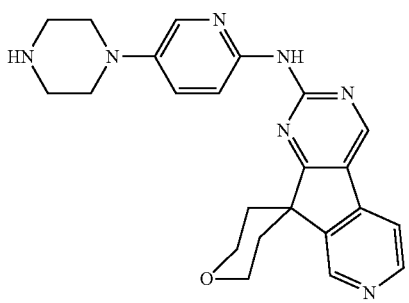

127

N-(5-(1-piperazinyl)-2-pyridinyl)-2,3,5,6-tetrahydrospiro[pyran-4,9'-pyrido[4',3':3,4]cyclopenta[1,2-d]pyrimidin]-2'-amine Title compound (127) was prepared using chemistry similar to that described in Example 61. $^1$H NMR (400 MHz, DMSO-d6) δ 10.74 (1H, s), 9.36 (1H, s), 9.24 (1H, s), 8.91 (2H, br s), 8.86 (1H, d, J=6.3 Hz), 8.39 (1H, d, J=5.9 Hz), 8.14 (1H, d, J=3.2 Hz), 8.07 (1H, d, J=9.0 Hz), 7.65 (1H, dd, J1=9.0 Hz, J2=3.1 Hz), 4.35 (2H, m), 3.93 (2H, m), 3.41 (4H, m), 3.28 (4H, m), 2.14 (2H, m), 1.80 (2H, m); LCMS-ESI (POS), M/Z, M+1: Found 416.2.

Example 64

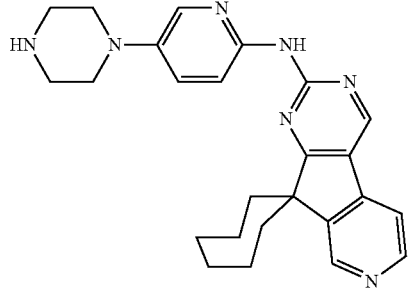

128

N-(5-(1-piperazinyl)-2-pyridinyl)spiro[cycloheptane-1,9'-pyrido[4',3':3,4]cyclopenta[1,2-d]pyrimidin]-2'-amine Title compound (128) was prepared using chemistry similar to that described in Example 61. $^1$H NMR (500 MHz, DMSO-d6) δ 9.89 (1H, s), 9.03 (1H, s), 8.54 (1H, d, J=5.1 Hz), 8.16 (1H, d, J=9.0 Hz), 8.03 (1H, d, J=3.2 Hz), 7.77 (1H, d, J=4.9 Hz), 7.47 (1H, dd, J1=9.0 Hz, J2=3.0 Hz), 3.15 (4H, m), 2.99 (4H, m), 2.10 (2H, m), 1.90-1.96 (2H, m), 1.81-1.86 (4H, m), 1.77 (4H, m); LCMS-ESI (POS), M/Z, M+1: Found 428.2.

Example 65

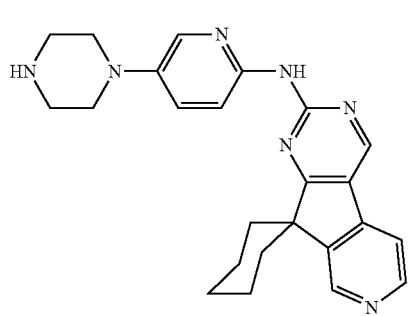

129

N-(5-(1-piperazinyl)-2-pyridinyl)spiro[cyclohexane-1,9'-pyrido[4',3':3,4]cyclopenta[1,2-d]pyrimidin]-2'-amine Title compound (129) was prepared using chemistry similar to that described in Example 61. $^1$H NMR (400 MHz, DMSO-d6) δ 10.74 (1H, s), 9.36 (1H, s), 9.18 (1H, s), 8.89 (2H, br s), 8.85 (1H, d, J=6.2 Hz), 8.40 (1H, d. J=5.9 Hz), 8.13 (1H, d, J=2.7 Hz), 8.10 (1H, br s), 7.66 (1H, dd, J1=9.0 Hz, J2=3.2 Hz), 3.40 (4H, m), 3.28 (4H, m), 2.18 (2H, m), 1.89 (2H, m), 1.72-1.82 (6H, m); LCMS-ESI (POS), M/Z, M+1: Found 414.2.

Example 66

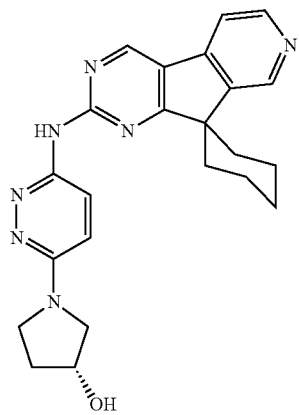

130

(3R)-1-(6-(spiro[cyclohexane-1,9'-pyrido[4',3':3,4]cyclopenta[1,2-d]pyrimidin]-2'-ylamino)-3-pyridazinyl)-3-pyrrolidinol Title compound (130) was prepared using chemistry similar to that described in Example 61. ¹H NMR (500 MHz, DMSO-d6) δ 10.18 (1H, s), 9.03 (1H, s), 8.89 (1H, s), 8.55 (1H, d, J=4.9 Hz), 8.07 (1H, d, J=9.6 Hz), 7.80 (1H, dd, J1=4.9 Hz, J2=1 Hz), 6.99 (1H, d, J=9.8 Hz), 4.99 (1H, d, J=3.7 Hz), 4.43 (1H, m), 3.52-3.57 (3H, m), 3.38 (2H, br d, J=10.5), 2.01-2.14 (3H, m), 1.93 (1H, m), 1.72-1.77 (8H, m); LCMS-ESI (POS), M/Z, M+1: Found 416.2.

Example 67

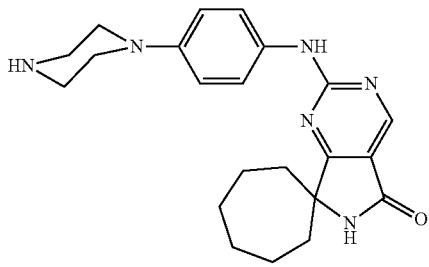

131

2'-((4-(1-piperazinyl)phenyl)amino)spiro[cycloheptane-1,7'-pyrrolo[3,4-d]pyrimidin]-5'(6'H)-one

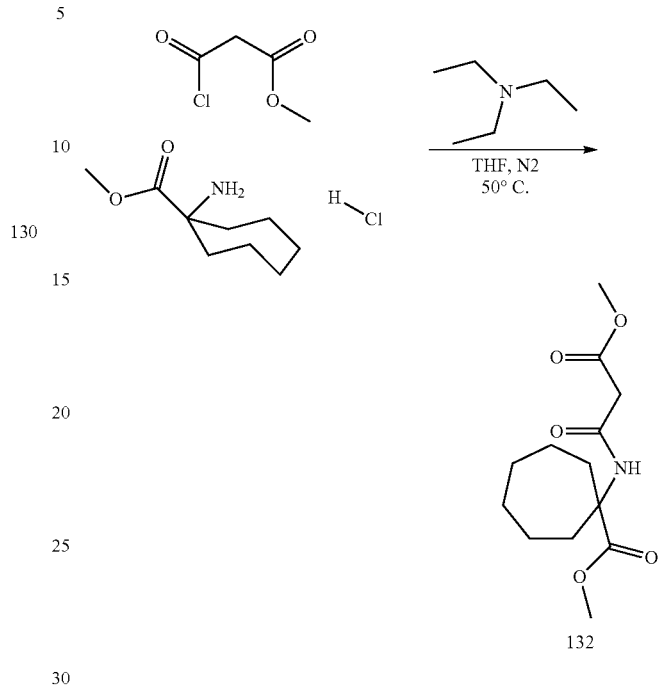

Methyl 1-((3-methoxy-3-oxopropanoyl)amino)cycloheptanecarboxylate (132) Methyl 3-chloro-3-oxopropanoate (4.50 ml, 42.0 mmol) was added cautiously to a solution of methyl 1-aminocycloheptanecarboxylate hydrochloride (7.04 g, 33.9 mmol) and triethylamine (11.8 ml, 84.7 mmol) in 50 ml of THF and then heated at 50 C for 2 hr. After cooling to rt, the solvent was removed under vacuum and the residue extracted between ether and water. The organic layer was dried over Na₂SO₄ and concentrated to afford methyl 1-((3-methoxy-3-oxopropanoyl)amino)cycloheptanecarboxylate (132) as a yellow oil (7.04, crude). LCMS-ESI (POS), M/Z, M+1: Found 272.0.

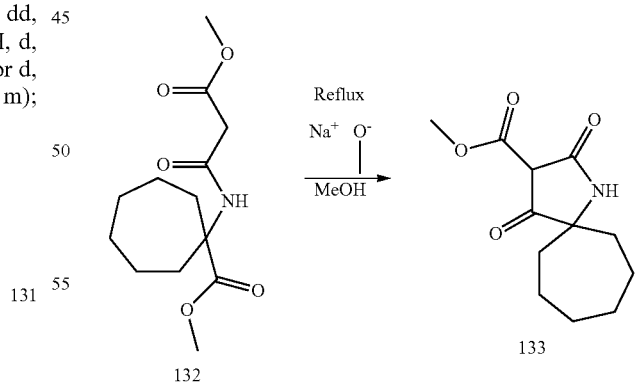

Methyl 2,4-dioxo-1-azaspiro[46]undecane-3-carboxylate (133) A solution of methyl 1-((3-methoxy-3-oxopropanoyl)amino)-cycloheptanecarboxylate (132) (7.29 g, 26.9 mmol) and sodium methoxide, (25 wt. % in methanol, 17.4 ml, 80.6 mmol) in 50 ml of MeOH was heated at a gentle reflux for two hours. After cooling to 20° C., the reaction was concentrated under vacuum to minimize organic solvent. The residue was taken up in ice water and adjusted to pH ~2-3 with 1N HCl. After extraction with DCM, the organic layer was dried over Na$_2$SO$_4$ and concentrated to afford methyl 2,4-dioxo-1-azaspiro[4.6]undecane-3-carboxylate (133) (5.84 g, crude). LCMS-ESI (NEG), M/Z, M+1: Found 238.0.

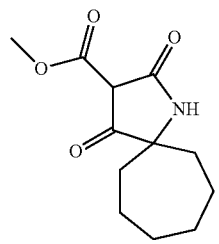 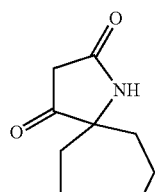

1-Azaspiro[4.6]undecane-2,4-dione (134). A solution of methyl 2,4-dioxo-1-azaspiro[4.6]undecane-3-carboxylate (133) (5.84 g, 24.4 mmol) in acetonitrile (100 ml) and water (1.32 ml, 73.2 mmol) was heated to a gentle reflux for 1 hr. After cooling to 20° C., the solvent was removed under vacuum to afford 1-azaspiro[4.6]undecane-2,4-dione (134) as a tan colored solid (4.08 g, crude). LCMS-ESI (NEG), M/Z, M+1: Found 180.1.

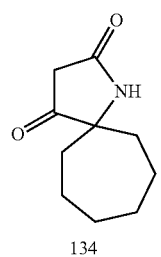 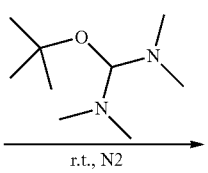

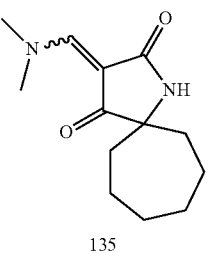

3-((Dimethylamino)methylidene)-1-azaspiro[4.6]undecane-2,4-dione (135). tert-Butoxy-bis(dimethylamino)methane (2.04 ml, 9.88 mmol) was added to a solution of 1-azaspiro[4.6]undecane-2,4-dione (134) (0.895 g, 4.94 mmol) in DCM (10 ml) and stirred at r.t. for 2 hrs. The product was collected as a white solid by filtration. Additional product was obtained by concentration of the filtrate and trituration with DCM. The combined yield gave 3-((dimethylamino)methylidene)-1-azaspiro[4.6]undecane-2,4-dione (135) (803 mg, 68.8%) as a white solid. $^1$H NMR (500 MHz, DMSO-d$_6$) δ ppm 7.80 (1H, s), 7.19 (1H, s), 3.59 (3H, s), 3.26 (3H, s), 1.66-1.78 (2H, m), 1.38-1.63 (10H, m), (E and Z isomers present in a 2:1 ratio); LCMS-ESI (POS), M/Z, M+1: Found 237.1.

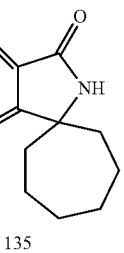 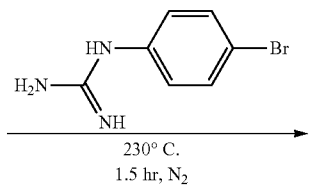

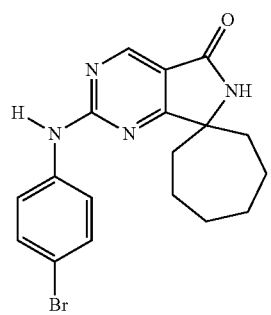

2'-((4-Bromophenyl)amino)spiro[cycloheptane-1,7'-pyrrolo[3,4-d]pyrimidin]-5'(6'H)-one (136). Under a nitrogen atmosphere, a solid mixture of 3-((dimethylamino)methylidene)-1-azaspiro[4.6]undecane-2,4-dione (135) (1.06 g, 4.49 mmol) and 1-(4-bromophenyl)guanidine hydrochloride (1.69 g, 6.73 mmol) was melted in a heating bath set at 230° C. After 1.5 hrs the reaction was cooled to 20° C. The residue was triturated with methanol 3× to afford 2'-((4-bromophenyl)amino)spiro[cycloheptane-1,7'-pyrrolo[3,4-d]pyrimidin]-5'(6'H)-one (136) as a light brown solid (680 mg, crude). LCMS-ESI (POS), M/Z, M+1: Found 387.0.

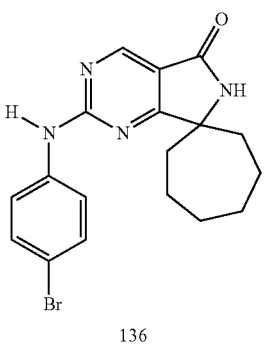

-continued

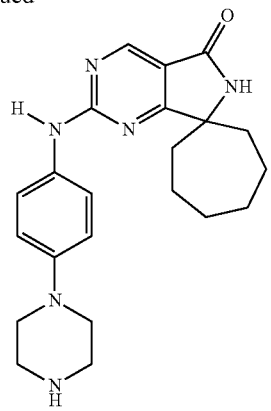

131

2'-((4-(1-piperazinyl)phenyl)amino)spiro[cycloheptane-1,7'-pyrrolo[3,4-d]pyrimidin]-5'(6'H)-one (131). Lithium bis(trimethylsilyl)amide, (1.0M solution in tetrahydrofuran, 1.68 ml, 1.68 mmol) under an atmosphere of $N_2$ was added to a solution of 2'-((4-bromophenyl)amino)spiro[cycloheptane-1,7'-pyrrolo[3,4-d]pyrimidin]-5'(6'H)-one (136) (0.217 g, 0.560 mmol), and piperazine (0.145 g, 1.68 mmol) in anhydrous toluene (3 ml). After degassing the solution with nitrogen, S-Phos (0.092 g, 0.224 mmol) and tris(dibenzylideneacetone)-dipalladium (0) (0.051 g, 0.056 mmol) were added and the reaction was heated at 100° C. for 2 hrs. Additional lithium bis(trimethylsilyl)amide, 1.0M solution in tetrahydrofuran (1.68 ml, 1.68 mmol), tris(dibenzylideneacetone) dipalladium (0) (0.051 g, 0.056 mmol), and S-Phos were added (0.092 g, 0.224 mmol) and the reaction was heated at 100° C. for another 1 hr before it was cooled to 20° C. The reaction was quenched with methanol and concentrated under vacuum. The residue was triturated with DCM and solids removed by filtration. The filtrate was concentrated under vacuum and purified by preparative HPLC eluting with a gradient of 20% MeCN-60% MeCN/$H_2$O/0.1% TFA. The fractions containing the product were combined and concentrated under vacuum. Trituration with methanol gave 2'4((4-(1-piperazinyl)phenyl)amino)spiro[cycloheptane-1,7'-pyrrolo[3,4-d]pyrimidin]-5'(6'H)-one (131) as a white solid (26 mg, crude). $^1$H NMR (500 MHz, DMSO-$d_6$) δ ppm 10.02 (1H, s), 8.75 (1H, s), 8.73 (2H, br. s.), 8.62 (1H, s), 7.68 (2H, d, J=8.5 Hz), 6.99 (2H, d, J=9.2 Hz), 3.28-3.32 (4H, m), 3.21-3.28 (4H, m), 1.92-2.02 (2H, m), 1.77-1.86 (2H, m), 1.55-1.77 (8H, m); LCMS-ESI (POS), M/Z, M+1: Found 393.2.

Example 68

2'-((4-(1-piperazinyl)phenyl)amino)spiro[cyclohexane-1,7'-pyrrolo[3,4-d]pyrimidin]-5'(6'H)-one Title compound (137) was prepared using chemistry similar to that described in Example 67. $^1$H NMR (500 MHz, DMSO-$d_6$) δ ppm 10.03 (1H, s), 8.88 (1H, s), 8.78 (2H, br. s.), 8.64 (1H, s), 7.66 (2H, d, J=7.9 Hz), 6.98 (2H, d, J=9.2 Hz), 3.27-3.31 (4H, m), 3.22-3.27 (4H, m), 1.74-1.89 (4H, m), 1.61-1.72 (3H, m), 1.45-1.53 (2H, m), 1.31-1.40 (1H, m); LCMS-ESI (POS), M/Z, M+1: Found 379.1.

Example 69

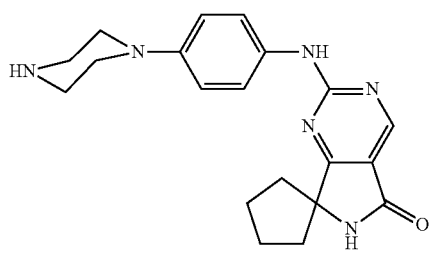

138

2'-((4-(1-piperazinyl)phenyl)amino)spiro[cyclopentane-1,7'-pyrrolo[3,4-d]pyrimidin]-5'(6'H)-one Title compound (138) was prepared using chemistry similar to that described in Example 67. $^1$H NMR (500 MHz, DMSO-$d_6$) δ ppm 10.02 (1H, s), 8.74 (2H, br. s.), 8.64 (1H, s), 8.61 (1H, s), 7.66 (2H, d, J=8.5 Hz), 6.97 (2H, d, J=9.2 Hz), 3.27-3.32 (4H, m), 3.21-3.27 (4H, m), 2.02-2.10 (2H, m), 1.87-1.94 (4H, m), 1.77-1.84 (2H, m); LCMS-ESI (POS), M/Z, M+1: Found 365.2.

Example 70

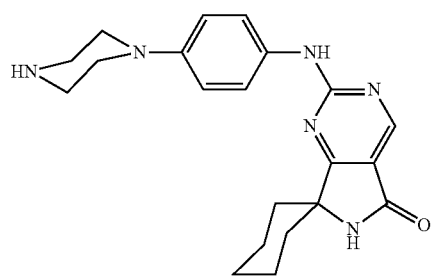

137

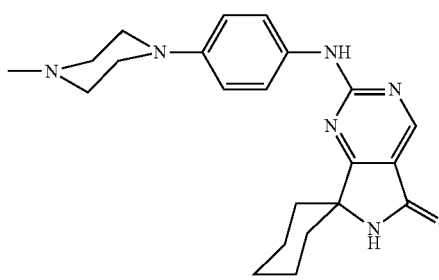

139

2'-((4-(4-methyl-1-piperazinyl)phenyl)amino)spiro[cyclohexane-1,7'-pyrrolo[3,4-d]pyrimidin]-5'(6'H)-one Title compound (139) was prepared using chemistry similar to that described in Example 67. ¹H NMR (500 MHz, DMSO-d₆) δ ppm 10.06 (1H, s), 9.71 (1H, br. s.), 8.91 (1H, s), 8.65 (1H, s), 7.67 (2H, d, J=8.1 Hz), 7.00 (2H, d, J=9.3 Hz), 3.79 (2H, d, J=13.0 Hz), 3.53 (2H, d, J=11.5 Hz), 3.12-3.27 (2H, m), 2.93 (2H, t, J=12.0 Hz), 2.88 (3H, d, J=3.4 Hz), 1.75-1.89 (4H, m), 1.62-1.73 (3H, m), 1.50 (2H, d, J=12.2 Hz), 1.37 (1H, m); LCMS-ESI (POS), M/Z, M+1: Found 393.2.

Example 71

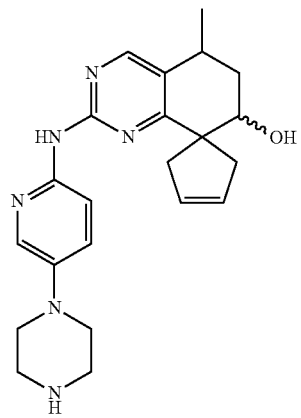

140

(7S)-5'-methyl-2'-((5-(1-piperazinyl)-2-pyridinyl)amino)-6',7'-dihydro-5'H-spiro[cyclopent-3-ene-1,8'-quinazolin]-7'-ol

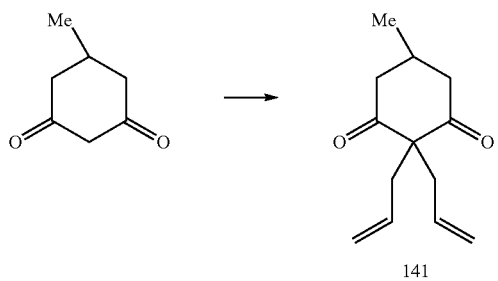

141

2,2-Diallyl-5-methylcyclohexane-1,3-dione (141) A 2 L 3-necked flask with mechanical stirring, addition port and reflux condenser was charged with a solution of 5-methylcyclohexane-1,3-dione (50.53 g, 400.5 mmol) in acetone (500 ml) followed by powdered potassium carbonate (100 g) and heated to 50° C. for 4 hr. After filtration, the solvent was removed under vacuum to afford 77.6 g of an oil containing a mixture of O and C alkylation products. This mixture was taken up in 2N HCl (600 ml) and heated at reflux for 1 hr. After cooling, the acid solution was extracted with dichloromethane. The organic layer was washed with 10% NaOH solution, brine and dried over magnesium sulfate. Removal of solvent under vacuum provided 2,2-diallyl-5-methylcyclohexane-1,3-dione (141) (37.48 g, 45% yield) as an oil. ¹H NMR (500 MHz, DMSO-d6) δ 5.50 (2H, m), 5.05-4.97 (4H, m), 2.673 (dd, J=19.5, 5 Hz, 2H), 2.443 (dd, J=19.5, 13 Hz, 2H) 2.428 (d, J=8.5 Hz, 4H), 2.039 (m, 1H), 0.947 (d, J=8.5 Hz, 3H) ppm; FTIR 1695 cm⁻¹.

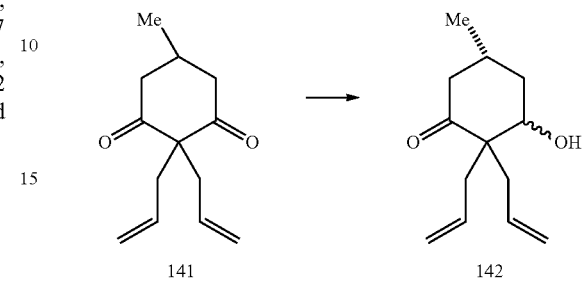

141                                    142

2,2-Diallyl-3-hydroxy-5-methylcyclohexanone (142) A solution of LiHAl(OtBu)3 (44 ml, 44 mmol) 1M in THF was added dropwise to a cold (0° C.) solution of 2,2-diallyl-5-methylcyclohexane-1,3-dione (141) (6.00 g, 29 mmol) in 60 mL THF. After stirring for 30 minutes, the reaction was poured cautiously into cold 5% citric acid solution. The organic layer was separated and concentrated to remove THF. The water layer was extracted with dichloromethane. The combined organic layer was washed with brine, dried over magnesium sulfate and then concentrated to afford 5.86 g of a 6:1 mixture of 2,2-diallyl-3-hydroxy-5-methylcyclohexanone (142) (cis/trans) with over-reduction to diol, as indicated by capillary GC analysis. The mixture was used directly in the next step. ¹H NMR (500 MHz, DMSO-d6) (key signals from major isomer) δ 3.681 (dd, J=11, 5 Hz, 1H), 0.973 (d, J=6 Hz, 3H) ppm; FTIR 3440, 1703 cm⁻¹.

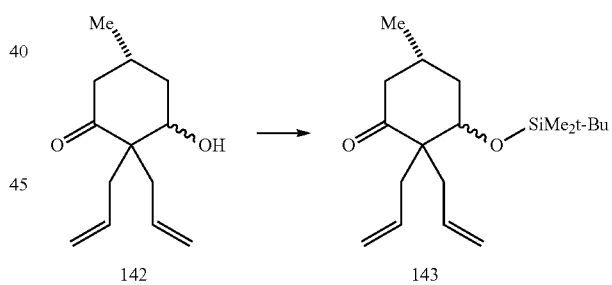

142                                    143

2,2-Diallyl-3-(tert-butyldimethylsilyloxy)-5-methylcyclohexanone (143) Tert-butyldimethylsilyl chloride (TBDMS) (5.14 g, 34.1 mmol) was added to a solution of 2,2-diallyl-3-hydroxy-5-methylcyclohexanone (142) (5.68 g, 27.3 mmol) and imidazole (4.64 g, 68.2 mmol) in 50 mL of DMF at 40 C. After several days, the reaction reached 70% conversion and an additional 1.6 g of TBDMS and 1.5 g of imidazole were added. On completion, the solvent was removed under vacuum and the residue poured onto ice water and extracted into ether. The ether layer was washed with water, sodium bicarbonate solution and brine. Concentration gave 7.65 g of a mixture of isomers. A portion (5.3 g) was purified by silica chromatography, eluting with hexane, followed by dichloromethane to afford 2,2-diallyl-3-(tert-butyldimethylsilyloxy)-5-methylcyclohexanone (143) (3.82 g) as an 8:1 mixture of cis:trans isomers. ¹H NMR (500 MHz, DMSO) (key signals from cis isomer) δ 5.63 (, 1H), 5.53 (m, 1H), 5.02 (m, 2H), 4.97 (m, 2H), 3.671 (dd, J=11, 5 Hz, 1H), 2.56 (m, 1H), 2.53 (, 1H), 2.24 (, 1H), 2.19 (, 1H), 2.06 (, 1H), 1.98 (, 1H), 1.82 (, 1H), 1.67 (, 1H), 1.60 (, 1H), 0.988 (d, J=6.5 Hz, 3H), 0.887 (s, 9H), 0.083 (s, 3H), 0.042 (s, 3H) ppm; (key signals from trans isomer) δ 4.028 (dd, J=4, 2 Hz, 0.1H), 0.983 (d, J=6.5 Hz, 0.3H); FTIR 1708 cm$^{-1}$.

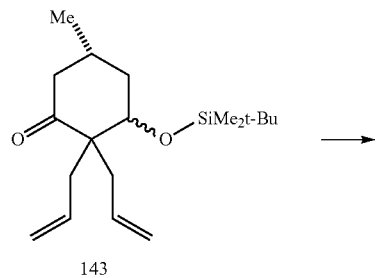

143

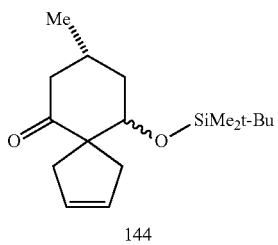

144

10-((tert-Butyl(dimethyl)silyl)oxy)-8-methylspiro[45]dec-2-en-6-one (144) Bis(tricyclohexylphosphine)benzylidine ruthenium(IV) chloride (Grubbs catalyst 1$^{st}$ generation) (0.193 g) was added to a degassed solution of 2,2-diallyl-3-(tert-butyldimethylsilyloxy)-5-methylcyclohexanone (143) (4.97 g, 15.4 mmol) in 500 ml of dichloromethane, under argon atmosphere and stirred for 60 hr. The mixture was then washed with 2N NaOH, 5% citric acid and brine. The organic layer was dried over magnesium sulfate and then concentrated under vacuum to provide 4.37 g of a dark solid. Purification by silica chromatography eluting with 1:1 hexane/dichloromethane gave 3.88 g of a 9:1 cis/trans mixture of 10-((tert-butyl(dimethyl)silyl)oxy)-8-methylspiro[45]dec-2-en-6-one (144) as a colorless solid. MP 56-59° C., $^1$H NMR (500 MHz, DMSO-d6) (signals from cis isomer) δ 5.550 (dt, J=5.5, 2.5 Hz, 1H), 5.408 (dm, J=6 Hz, 1H), 3.686 (dd, J=11, 4 Hz, 1H), 3.038 (dq, J=16, 2.5 Hz, 1H), 2.833 (dp, J=17, 2 Hz, 1H), 2.314 (dd, J=14.5, 13, 1H), 2.11-2.16 (m, 2H), 2.066 (m, 1H), 1.833 (, 1H), 1.694 (m, 1H), 1.420 (ddd, J=15, 12.5, 12 Hz, 1H), 0.975 (d, J=6.5 Hz, 3H), 0.822 (s, 9H), 0.072 (s, 3H), 0.031 (s, 3H), 0.029 (s, 3H) ppm; FTIR 1710 cm$^{-1}$; (key signals from trans isomer) δ 4.028 (dd, J=3.4, 2.1 Hz, 0.11H), 0.963 (d, J=6.5 Hz, 0.3H) ppm; LCMS-ESI (POS), M/Z, M+1: Found 295.1.

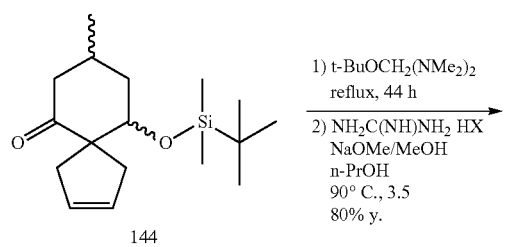

144

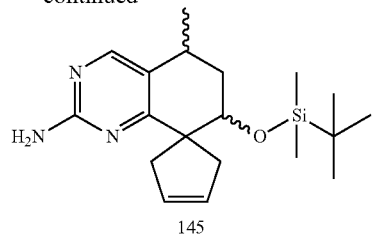

145

7'-((tert-Butyl(dimethyl)silyl)oxy)-5'-methyl-6',7'-dihydro-5'H-spiro[cyclopent-3-ene-1,8'-quinazolin]-2'-amine (145) Title compound (145) was prepared in 80% yield from compound (144) using chemistry similar to that described in Example 1. LCMS-ESI (POS), M/Z, M+1: Found 346.1, Calculated 346.22.

(7S)-5'-methyl-2'-((5-(1-piperazinyl)-2-pyridinyl)amino)-6',7'-dihydro-5'H-spiro[cyclopent-3-ene-1,8'-quinazolin]-7'-ol (140) was prepared from (145) using chemistry similar to that described in example 1 and silyl removal as described in example 72. $^1$H NMR (400 MHz, DMSO-d$_6$) δ ppm 11.45 (1H, br. s.), 9.10 (2H, br. s.), 8.63 (1H, s), 8.05 (1H, dd, J=9.4, 2.7 Hz), 7.80 (1H, d, J=2.7 Hz), 7.67 (1H, d, J=9.4 Hz), 5.95-6.09 (1H, m), 5.71-5.83 (1H, m), 3.78 (1H, dd, J=11.2, 2.9 Hz), 3.36-3.48 (4H, m), 3.29 (4H, br. s.), 2.91-3.02 (2H, m), 2.70-2.86 (2H, m), 2.23 (1H, d, J=16.8 Hz), 1.97-2.09 (1H, m), 1.41 (1H, q), 1.33 (3H, d, J=6.7 Hz). LCMS-ESI (POS), M/Z, M+1: Found 393.2.

Example 72

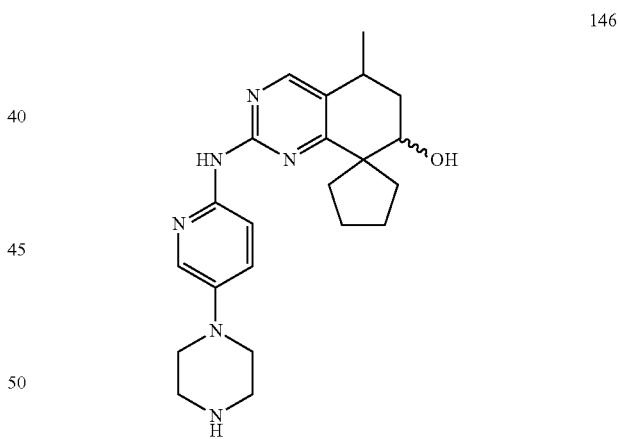

146

(7'S)-5'-methyl-2'-((5-(1-piperazinyl)-2-pyridinyl)amino)-6',7'-dihydro-5'H-Spiro[cyclopentane-1,8'-quinazolin]-7'-ol Title compound 146 was prepared from 148 using chemistry similar to that described in Example 1. $^1$H NMR (400 MHz, MeOH) δ ppm 8.55 (1H, s), 8.10 (1H, dd, J=9.6, 2.9 Hz), 7.89 (1H, d, J=2.3 Hz), 7.49 (1H, d, J=9.4 Hz), 3.88 (1H, dd, J=10.6, 3.1 Hz), 3.46-3.53 (4H, m), 3.40-3.46 (4H, m), 2.99-3.10 (1H, m), 2.12-2.28 (3H, m), 1.56-2.08 (7H, m), 1.43 (3H, d, J=6.7 Hz). LCMS-ESI (POS), M/Z, M+1: Found 395.2.

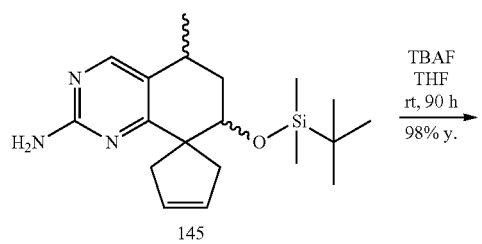

145

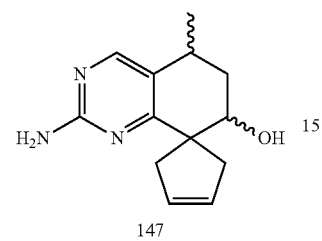

147

2'-Amino-5'-methyl-6',7'-dihydro-5'H-spiro[cyclopent-3-ene-1,8'-quinazolin]-7'-ol (147) Tetrabutylammonium fluoride, (1.0M in THF, 13.0 mL, 13 mmol) was added to a solution of 145 (1.1 g, 3.2 mmol) in THF (20 ml) and stirred at rt for 90 h at which time LC-MS showed completion. After concentration in vacuo, the residue was purified by combiflash column chromatography (MeOH/DCM) to give alcohol 147 (0.75 g) as an 8:1 mixture of cis- and trans-isomers based on ¹H NMR and analytical reverse phase HPLC. LCMS-ESI (POS), M/Z, M+1: Found 232.1.

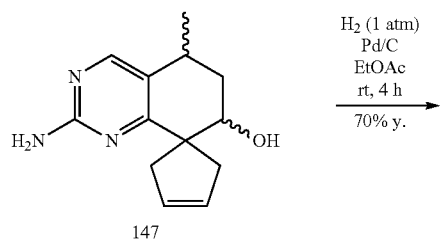

147

148

2'-Amino-5'-methyl-6',7'-dihydro-5'H-spiro[cyclopentane-1,8'-quinazolin]-7'-ol (148) A solution of 2'-Amino-5'-methyl-6',7'-dihydro-5'H-spiro[cyclopent-3-ene-1,8'-quinazolin]-7'-ol (147) (0.65 g, 2.8 mmol) in EtOAc (30 mL) was hydrogenated in the presence of palladium, 10 wt. % (dry basis) on activated carbon, wet, Degussa type E101 NE/W (~0.3 g, 2.8 mmol) under 1 atmosphere of H₂ for 4 h. The mixture was then filtered through a layer of Celite and concentrated in vacuo to give 2'-amino-5'-methyl-6',7'-dihydro-5'H-spiro[cyclopentane-1,8'-quinazolin]-7'-ol (148) (0.46 g, 70% yield). LCMS-ESI (POS), M/Z, M+1: Found 234.1.

Example 73

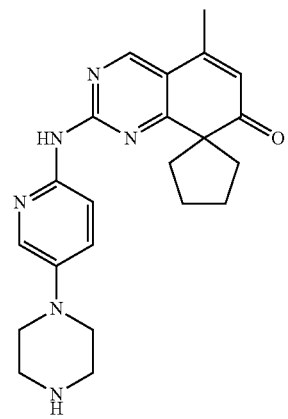

149

5'-methyl-2'-((5-(1-piperazinyl)-2-pyridinyl)amino)-7'H-spiro[cyclopentane-1,8'-quinazolin]-7'-one Title compound 149 was prepared from compound 152 using chemistry similar to that described in Example 2. ¹H NMR (400 MHz, MeOH) δ ppm 8.85 (1H, s), 8.17 (1H, dd, J=9.6, 2.9 Hz), 7.96 (1H, d, J=2.7 Hz), 7.63 (1H, d, J=9.4 Hz), 6.18 (1H, d, J=1.2 Hz), 3.49-3.59 (4H, m), 3.40-3.49 (4H, m), 2.45 (3H, d, J=1.2 Hz), 2.13-2.30 (4H, m), 1.92-2.12 (4H, m). LCMS-ESI (POS), M/Z, M+1: Found 391.1, Calculated 391.22.

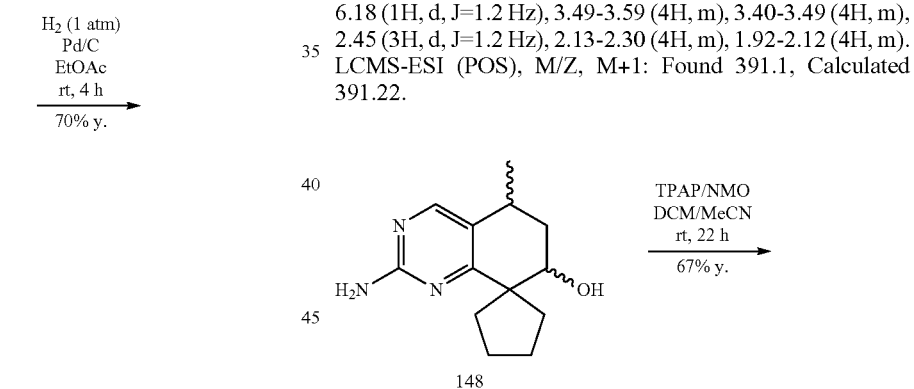

148

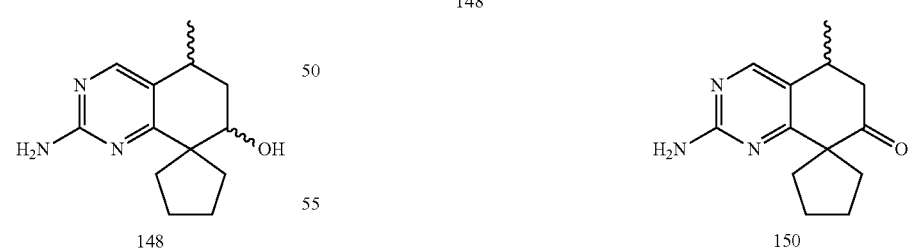

150

2'-Amino-5'-methyl-5',6'-dihydro-7'H-spiro[cyclopentane-1,8'-quinazolin]-7'-one (150) A solution of 2'-amino-5'-methyl-6',7'-dihydro-5'H-spiro[cyclopentane-1,8'-quinazolin]-7'-ol (148) (0.42 g, 1.8 mmol) in DCM (10 mL), 4-methylmorpholine 4-oxide (0.53 g, 4.5 mmol), and tetrapropylammonium perruthenate (0.095 g, 0.27 mmol) with, 4A molecular sieves, (<5 micron, activated (~1.8 g)) was stirred at rt for 22 h. Upon workup, the mixture was filtered through a layer of Celite and the residue after concentration in vacuo was purified by combi-flash column chromatography (MeOH/DCM) to give impure 2'-amino-5'-methyl-5',6'-dihydro-7'H-spiro[cyclopentane-1,8'-quinazolin]-7'-one (150) (0.28 g, 67% yield) as a colorless film. LCMS-ESI (POS), M/Z, M+1: Found 232.1.

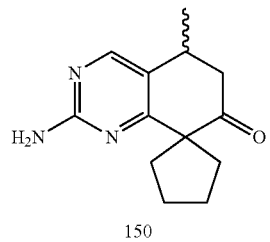

150

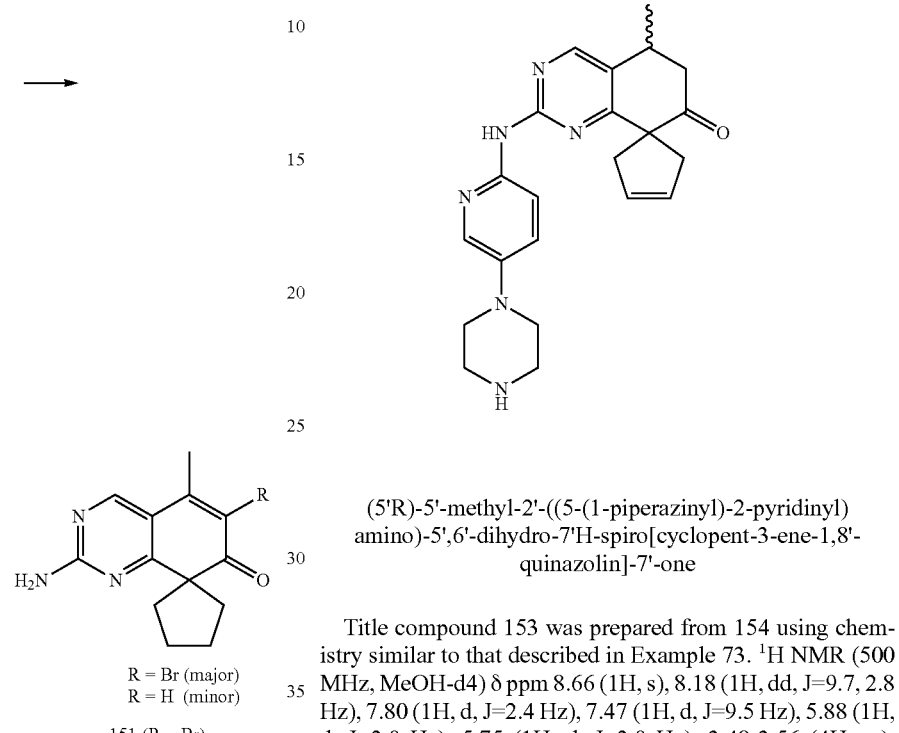

2'-Amino-6'-bromo-5'-methyl-7'H-spiro[cyclopentane-1, 8'-quinazolin]-7'-one (151) and 2'-amino-5'-methyl-7'H-spiro[cyclopentane-1,8'-quinazolin]-7'-one (152) A solution of 2'-amino-5'-methyl-5',6'-dihydro-7'H-spiro[cyclopentane-1,8'-quinazolin]-7'-one (150) (0.27 g, 1.2 mmol) in a mixed solvents of DCM (10 mL) and EtOAc (10 mL) with copper(II) bromide (0.52 g, 2.3 mmol added in two equal portions over a period of 15 min.) was heated at reflux for 9 h and then stirred at rt overnight. More copper(II) bromide (0.52 g, 2.3 mmol) was added to the reaction mixture and the mixture was heated to reflux again for 6 h. More copper(II) bromide (0.52 g, 2.3 mmol) was added to the reaction mixture and the mixture was heated at reflux once more overnight. Upon workup, the mixture was cooled to rt and poured into ice and saturated NH₄Cl aqueous solution and extracted with EtOAc (2×). The combined organic layer was washed with brine (1×), dried over Na₂SO₄, and concentrated in vacuo. The crude residue was dissolved in THF (12 mL) and diisopropylethylamine (209 µl, 1.2 mmol) and heated at reflux for 20 h. After the volatiles were removed, the residue was purified by combi-flash column chromatography (EtOAc/Hexanes) to give 2'-amino-6'-bromo-5'-methyl-7'H-spiro[cyclopentane-1,8'-quinazolin]-7'-one (151) (57 mg) as a light yellow solid and 2'-amino-5'-methyl-7'H-spiro[cyclopentane-1,8'-quinazolin]-7'-one (152) (20 mg). For (151): LCMS-ESI (POS), M/Z, M+1: Found 308.0 For (152): ¹H NMR (400 MHz, CHLOROFORM-d) δ ppm 8.38 (1H, s), 5.97 (1H, s), 5.41 (2H, br. s.), 2.30 (3H, d, J=1.2 Hz), 1.88-2.22 (8H, m). LCMS-ESI (POS), M/Z, M+1: Found 230.2.

Example 74

(5'R)-5'-methyl-2'-((5-(1-piperazinyl)-2-pyridinyl)amino)-5',6'-dihydro-7'H-spiro[cyclopent-3-ene-1,8'-quinazolin]-7'-one Title compound 153 was prepared from 154 using chemistry similar to that described in Example 73. ¹H NMR (500 MHz, MeOH-d4) δ ppm 8.66 (1H, s), 8.18 (1H, dd, J=9.7, 2.8 Hz), 7.80 (1H, d, J=2.4 Hz), 7.47 (1H, d, J=9.5 Hz), 5.88 (1H, d, J=2.0 Hz), 5.75 (1H, d, J=2.0 Hz), 3.48-3.56 (4H, m), 3.37-3.47 (5H, m), 3.20 (1H, d, J=16.6 Hz), 2.83-3.03 (4H, m), 2.56 (1H, dd, J=14.4, 6.6 Hz), 1.33 (3H, d, J=6.8 Hz). LCMS-ESI (POS), M/Z, M+1: Found 391.1.

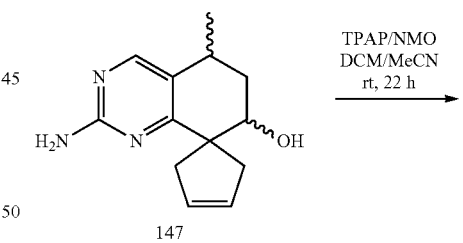

147

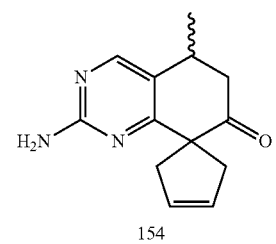

154

2'-Amino-5'-methyl-5',6'-dihydro-7'H-spiro[cyclopent-3-ene-1,8'-quinazolin]-7'-one. The title compound (154) was prepared from 147 using chemistry similar to that described for compound 150 in Example 73. LCMS-ESI (POS), M/Z, M+1: Found 230.2.

Example 75

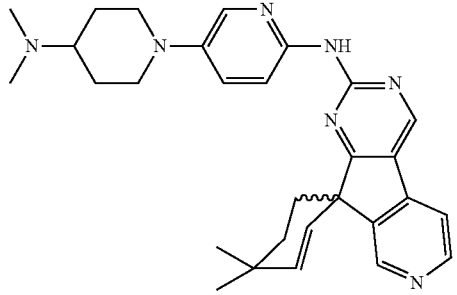

155

(racemic)-4,4-dimethyl-N-(6-(4-(dimethylamino)piperidin-1-yl)-3-pyridinyl)spiro[cyclohex-2-ene-1,9'-pyrido[4',3':3,4]cyclopenta[1,2-d]pyrimidin]-2'-amine (155) was prepared from 89 using chemistry similar to that described in Example 27. $^1$H NMR (400 MHz, MeOH-d4) (taken as a TFA salt) δ ppm 9.46 (1H, d, J=2Hz), 8.90 (1H, s), 8.85 (1H, d, J=6.4 Hz), 8.53 (1H, dd, J=6, 2.8 Hz), 8.22 (1H, dt, J=9.2, 3.2 Hz), 7.98 (1H, d, J=3.2 Hz), 7.65 (1H, d, J=9.6 Hz), 6.13 (1H, d, J=9.6 Hz), 5.22 (1H, d, J=9.6 Hz), 4.91 (3H, br. s.), 4.90 (3H, s), 3.99 (2H, dm, J=12.8 Hz), 3.46 (1H, tt, J=12, 4 Hz), 2.99 (2H, td, J=12.4, 1.6 Hz), 2.94 (6H, m), 2.31-2.24 (4H, m), 2.06 (1H, m), 1.99 (3H, m), 1.310 (3H, s), 1.30 (3H, s). LCMS-ESI (POS), M/Z, M+1: Found 482.4.

Example 76

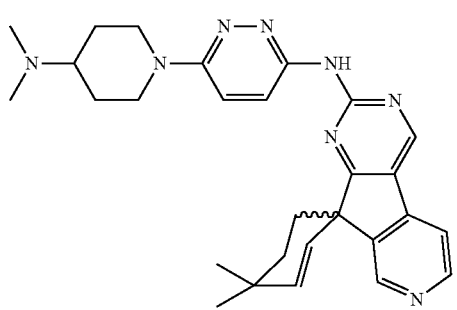

156

(racemic)-4,4-dimethyl-N-(6-(4-(dimethylamino)piperidin-1-yl)-pyridazin-3-yl)spiro[cyclohex-2-ene-1,9'-pyrido[4',3':3,4]cyclopenta[1,2-d]pyrimidin]-2'-amine (156) was prepared from 89 using chemistry similar to that described in Example 27. $^1$H NMR (400 MHz, MeOH-d4) (taken as a TFA salt) δ ppm 9.49 (1H, s), 8.92 (1H, s), 8.86 (1H, d, J=6 Hz), 8.51 (1H, dd, J=6, 2 Hz), 8.11 (1H, d, J=10 Hz), 8.00 (1H, d, J=10 Hz), 6.14 (1H, d, J=10 Hz), 5.21 (1H, d, J=9.6 Hz), 4.91 (3H, br. s.), 4.89 (3H, s), 4.53 (2H, dm, J=14 Hz), 3.58 (1H, tt, J=12, 3.6 Hz), 3.18 (2H, br t, J=12 Hz), 2.91 (6H, s), 2.94 (6H, m), 2.27-2.21 (4H, m), 2.09 (1H, m), 1.85 (3H, m), 1.30 (6H, br s). LCMS-ESI (POS), M/Z, M+1: Found 483.3.

Example 77

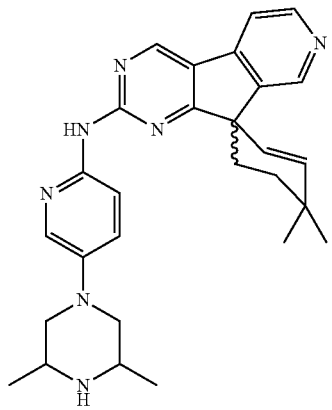

157

(racemic)-4,4-dimethyl-N-(6-((cis-3,5-dimethylpiperazin-1-yl)pyridin-3-yl)spiro[cyclohex-2-ene-1,9'-pyrido[4',3':3,4]cyclopenta[1,2-d]pyrimidin]-2'-amine (157) was prepared from 89 using chemistry similar to that described in Example 27. $^1$H NMR (400 MHz, MeOH-d4) (taken as a TFA salt) δ ppm 9.46 (1H, s), 8.90 (1H, s), 8.85 (1H, d, J=6 Hz), 8.53 (1H, br d, J=5.6 Hz), 8.22 (1H, d, J=9.6 Hz), 8.06 (1H, d, J=2.8 Hz), 7.73 (1H, d, J=9.6 Hz), 6.13 (1H, d, J=9.6 Hz), 5.22 (1H, d, J=9.6 Hz), 4.91 (12H, br. s.), 3.98 (2H, dd, J=13.6, 2.4 Hz), 3.59 (2H, m), 2.89 (2H, dd, J=12.8, 11.6 Hz), 2.27 (2H, m), 2.06 (1H, m), 1.88 (1H, m), 1.45 (6H, d. J=6.8 Hz), 1.31 (3H, s), 1.30 (3H, s). LCMS-ESI (POS), M/Z, M+1: Found 468.2.

Biological Testing

The pharmacological properties of the compounds of this invention may be confirmed by in vitro assays such as those described below.

The Cdk4 and Cdk6 inhibitory activity of the compounds is measured with a kinase inhibition assay using recombinant Cdk4/CyclinD1 or Cdk6/CyclinD3 protein complexes. The protein substrate used in the assay is the retinoblastoma protein (Rb). The kinase reactions are carried out in a 96-well filter plate (MSDV N6B50, Millipore). Compounds are serially diluted in kinase buffer (20 mM Tris-HCl, pH 7.4, 50 mM NaCl, 1 mM DTT, 1 mg/ml BSA) and added to the reaction mixture containing 2.5 ng/ml Cdk4/CyclinD1 or Cdk6/CyclinD3, 25 µM ATP, 10 µCi/ml [$^{33}$P]-ATP, 0.1 µg/ml Rb in the kinase buffer. The mixture is incubated at room temperature for 1 hour and the proteins precipitated with an equal volume of 20% TCA. The plates are washed with 10% TCA according to the manufacturer's instruction and dried at room temperature. The amount of the phosphorylated Rb is determined with a TopCount (PerkinElmer). The IC$_{50}$ of a compound is determined by nonlinear regression curve fitting using software program Prism 5 (GraphPad Software).

The cellular activity of the compounds is measured with a cell-based DNA synthesis inhibition assay. Rb positive (e.g. Colo-205, MDA-MB-435) or Rb negative (e.g. MDA-MB-436, H2009) cancer cells are seeded in the 96-well Cytostar plates (GE Healthcare, Cat# RPNQ0163) at a density of 3000-5000 cells/well. Dilutions of compounds are added to the cells. After 24 hour incubation at 37 C, $^{14}$C-thymidine is added (0.1 μCi/well). After additional 48 hour incubation at 37 C, incorporation of $^{14}$C-thymidine into the DNA of the cells was measured with a TopCount (PerkinElmer). The $IC_{50}$ of a compound is determined by nonlinear regression curve fitting using software program Prism 5 (GraphPad Software).

The Cdk4 or Cdk6 inhibitory activity of the compounds may also be measured with kinase assays of a different format, e.g., a homogeneous time-resolved fluorescence energy transfer (HTRF) assay (Jia Y. et al, *Anal Biochem.* 2006; 356:273-281) or a fluorescence polarization (FP) assay (Sportsman J R, et al. *Comb Chem High Throughput Screen.* 2003; 6:195-200).

The compounds exemplified herein have been assayed and exhibit Cdk 4 $IC_{50}$'s in a range from 3.5 μm to 0.8 nm, and exhibit Cdk 6$IC_{50}$'s, where determined from 2.62 μm to 1.1 nm. Illustrative activity values are provided in the following Table 5.

TABLE 5

| Example Compound | Cdk 4 $IC_{50}$ (μM) | Cdk 6 $IC_{50}$ (μm) |
| --- | --- | --- |
| 3 | 0.0142 | 0.0142 |
| 15 | 0.084 | 0.0135 |
| 23 | 2.85 | 2.62 |
| 25 | 0.33 | 0.54 |
| 27 | 0.074 | 0.068 |
| 29 | 0.0059 | 0.0011 |
| 35 | 0.077 | 0.06 |
| 40 | 0.084 | 0.033 |
| 44 | 0.0008 | 0.027 |
| 48 | 0.044 | 0.266 |
| 49 | 0.668 | ND |
| 50 | 0.0562 | 0.081 |
| 63 | 0.41 | ND |
| 68 | 1.14 | ND |
| 71 | 0.71 | 0.51 |
| 73 | 2.5 | ND |
| 74 | 3.5 | 1.8 |
| 76 | 0.0146 | 0.205 |

Formulations

Also embraced within this invention is a class of pharmaceutical compositions comprising the active compounds of Formula I-II in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.01 and about 50 mg/kg, and more preferably about 0.01 and about 30 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes, which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

We claim:

1. A compound of Formula IA, IB, IC, or ID

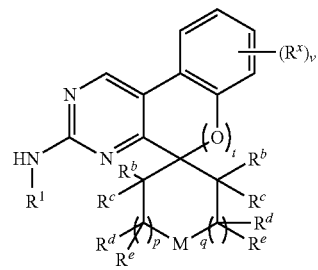

IA

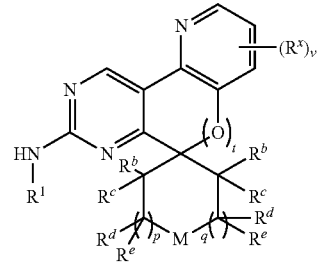

IB

-continued

IC

ID or an enantiomer, diastereomer, or salt thereof wherein
t is 0;
v is 0, 1, 2, or 3;
$R^1$ is —Y—$R^a$ wherein
  Y is selected from phenyl, pyridyl, pyrimidinyl, pyrazinyl, thiazolyl, or pyradizinyl any of which may be optionally independently substituted with one or more $R^x$ groups as allowed by valence; and
  $R^a$ is selected from piperazinyl, piperidinyl, morpholinyl, or pyrrolidinyl any of which may be optionally substituted with one or more $R^x$ group as allowed by valence;
M is —$CR^dR^e$—, —O—, —$S(O)_n$—, or —$NHR^3$—;
$R^b$, $R^c$, $R^d$ and $R^e$ are each independently H or $R^x$, or alternatively $R^b$ and $R^d$ on adjacent carbon ring atoms may optionally combine to form a double bond as allowed by valence, and $R^d$ and $R^e$ on adjacent carbon ring atoms may optionally combine to form a double bond as allowed by valence;
$R^3$ and $R^4$ at each occurrence are independently
  (i) hydrogen or
  (ii) alkyl, cycloalkyl, heterocyclo, aryl, heteroaryl, cycloalkylalkyl, heterocycloalkyl, arylalkyl, or heteroarylalkyl;
or $R^3$ and $R^4$ together with the nitrogen atom to which they are attached may combine to form a heterocyclo ring;
$R^5$ is
  (i) hydrogen or
  (ii) alkyl, alkenyl, alkynyl cycloalkyl, heterocyclo, aryl, heteroaryl, cycloalkylalkyl, heterocycloalkyl, arylalkyl, or heteroarylalkyl;
$R^x$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-$OR^5$, -(alkylene)$_m$-$S(O)_nR^5$, -(alkylene)$_m$-$NR^3R^4$, -(alkylene)$_m$-C(=O)$R^5$, -(alkylene)$_m$-C(=S)$R^5$, -(alkylene)$_m$-C(=O)$OR^5$, -(alkylene)$_m$-OC(=O)$R^5$, -(alkylene)$_m$-C(=S)$OR^5$, -(alkylene)$_m$-C(=O)$NR^3R^4$, -(alkylene)$_m$-C(=S)$NR^3R^4$, -(alkylene)$_m$-N($R^3$)C(=O)$NR^3R^4$, -(alkylene)$_m$-N($R^3$)C(=S)$NR^3R^4$, -(alkylene)$_m$-N($R^3$)C(=O)$R^5$, -(alkylene)$_m$-N($R^3$)C(=S)$R^5$, -(alkylene)$_m$-OC(=O)$NR^3R^4$, -(alkylene)$_m$-OC(=S)$NR^3R^4$, -(alkylene)$_m$-SO$_2NR^3R^4$, -(alkylene)$_m$-N($R^3$)SO$_2R^5$, -(alkylene)$_m$-N($R^3$)SO$_2NR^3R^4$, -(alkylene)$_m$-N($R^3$)C(=O)$OR^5$, -(alkylene)$_m$-N($R^3$)C(=S)$OR^5$, or -(alkylene)$_m$-N($R^3$)SO$_2R^5$;
n is 0, 1 or 2;
m is 0 or 1; and
p and q are independently 0, 1 or 2.

2. A compound of claim 1 wherein $R^1$ is selected from

3. The compound of claim 1, wherein the compound has the Formula IA.

4. The compound of claim 3 wherein $R^1$ is selected from

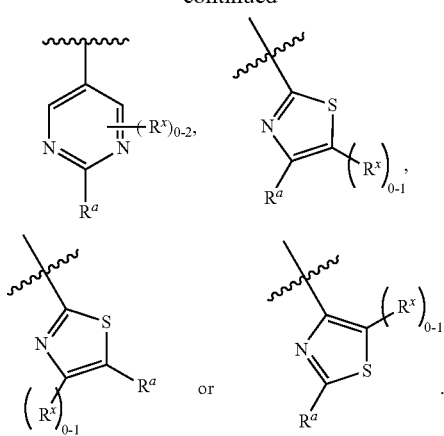
5. The compound of claim 4 wherein R¹ is selected from
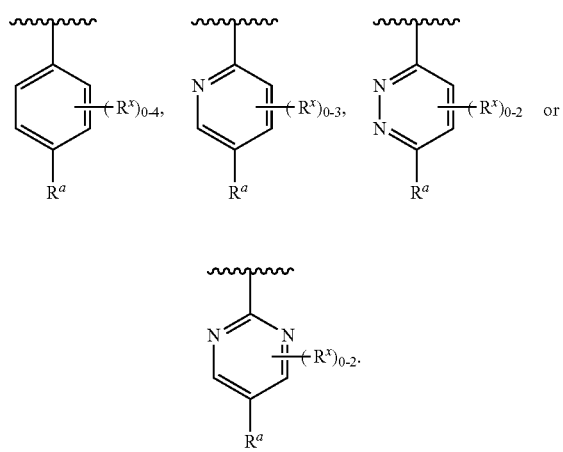
6. The compound of claim 3 wherein
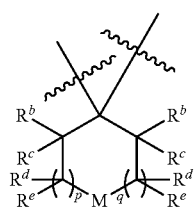
is selected from
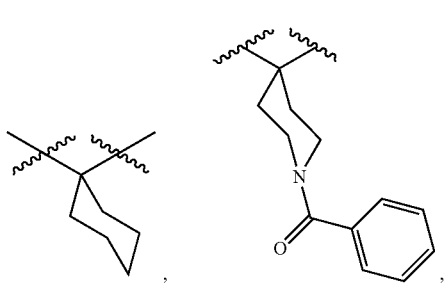
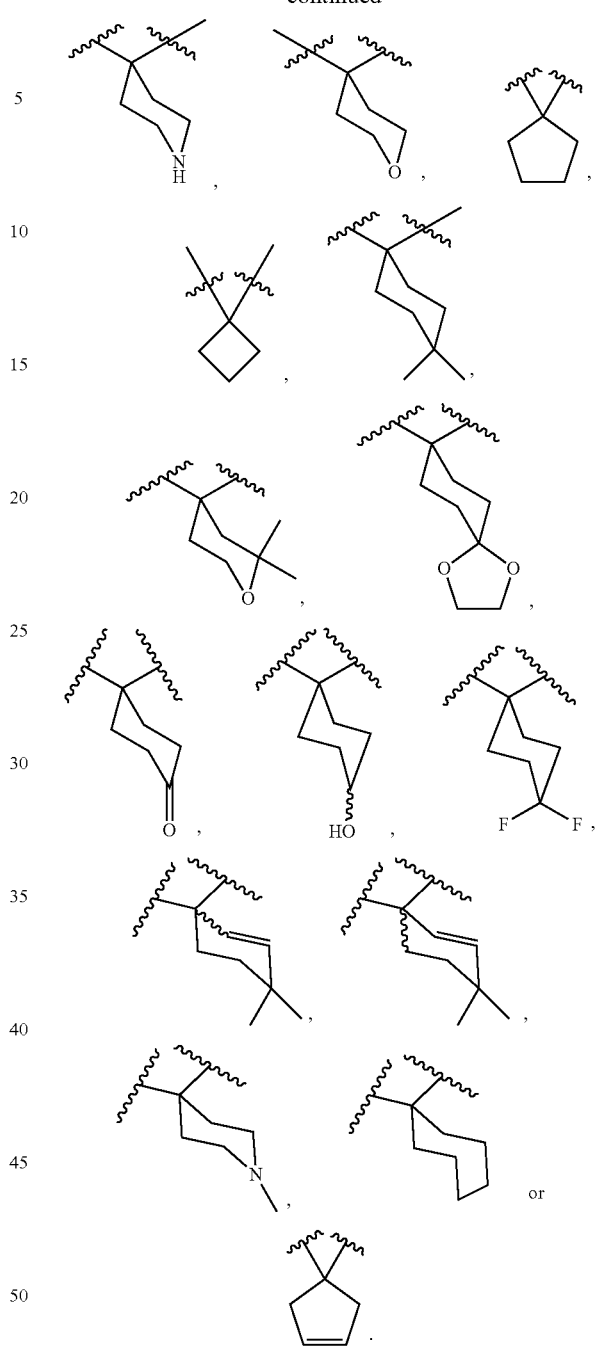
7. The compound of claim 1, wherein the compound has the Formula IB.
8. The compound of claim 7 wherein R¹ is selected from
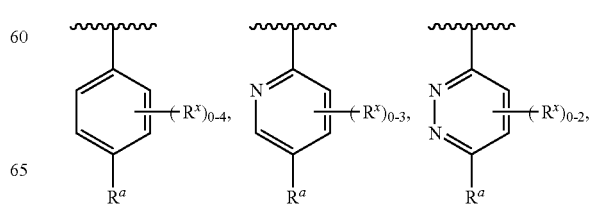

-continued
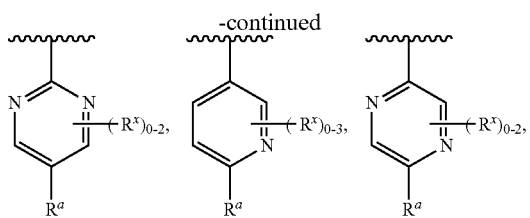
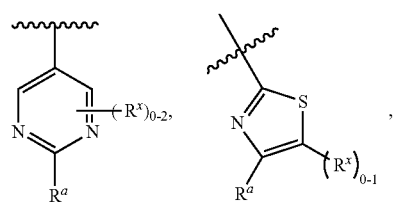
9. The compound of claim 8 wherein R¹ is selected from
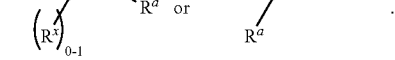
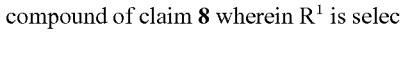
10. The compound of claim 7 wherein
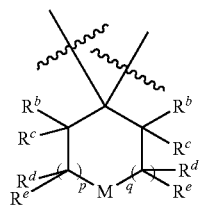
is selected from
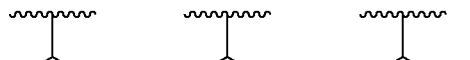
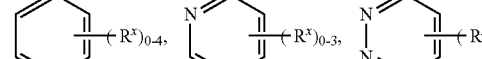
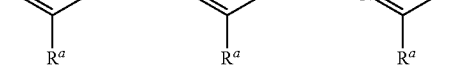
11. The compound of claim 1, wherein the compound has the Formula IC.
12. The compound of claim 11 wherein R¹ is selected from
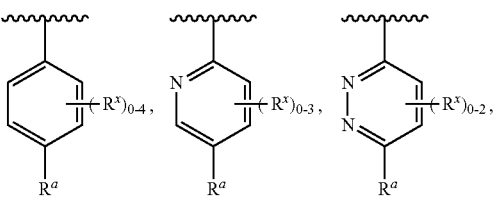

-continued
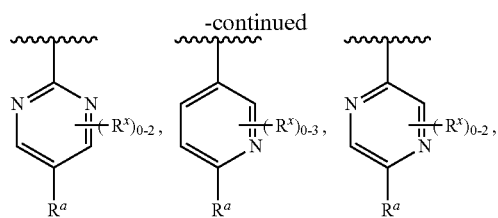
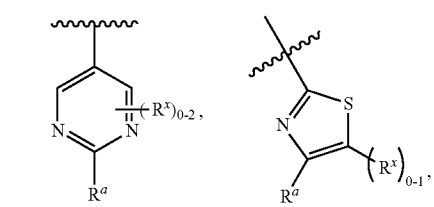
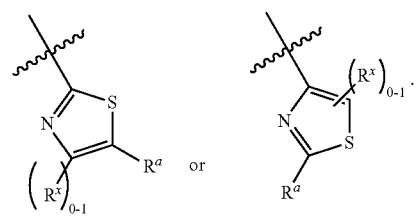 or
13. The compound of claim 12 wherein R¹ is selected from
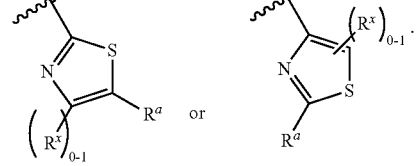
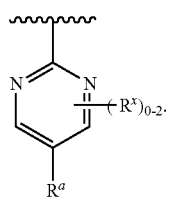
14. The compound of claim 11 wherein
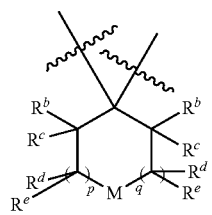
is selected from
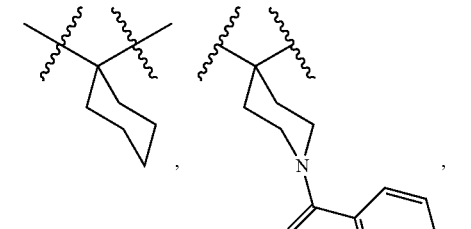
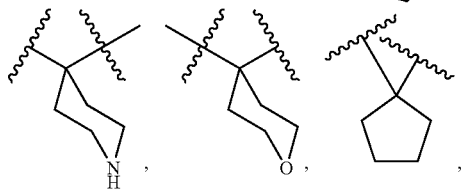
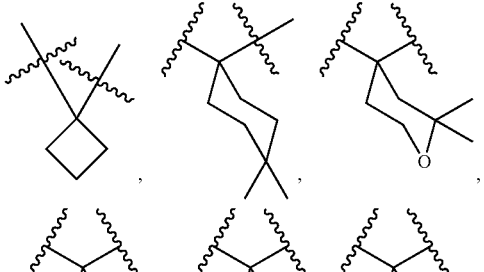
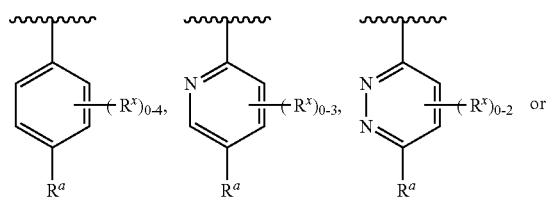
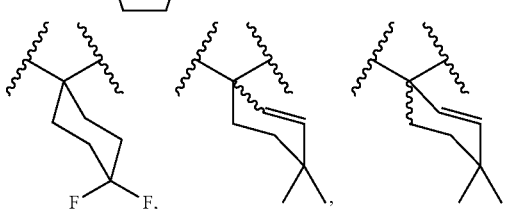
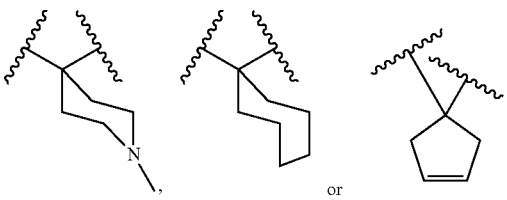 or
15. The compound of claim 1, wherein the compound has the Formula ID.
16. The compound of claim 15 wherein R¹ is selected from
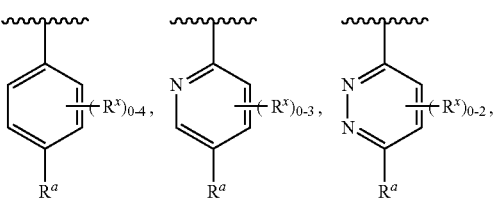

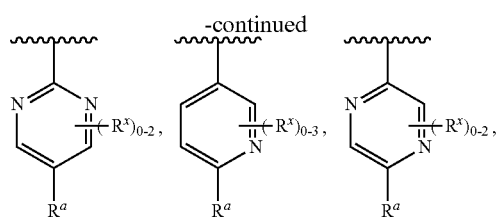
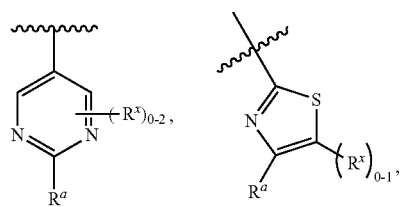
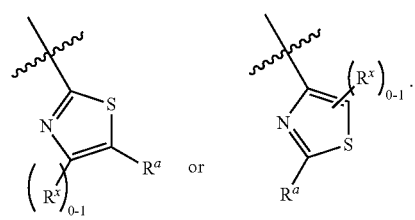
17. The compound of claim 16 wherein R¹ is selected from
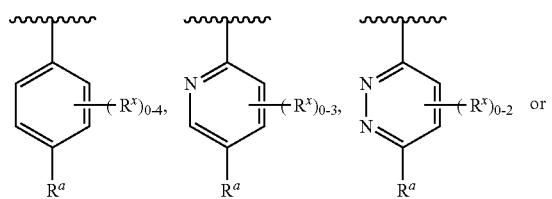
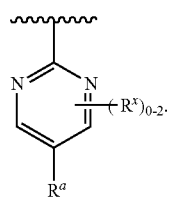
18. The compound of claim 15 wherein
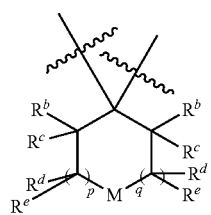
is selected from
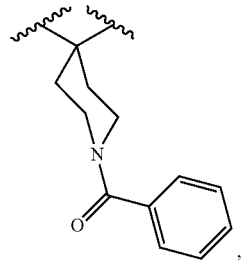
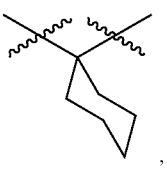
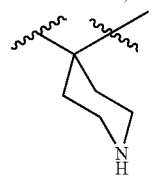
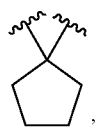
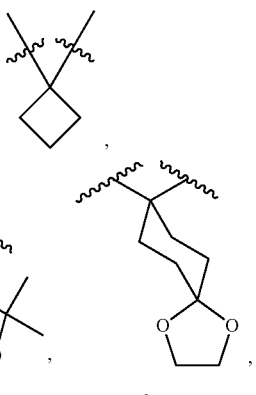
19. A compound or a pharmaceutically acceptable salt thereof selected from
4,4-dimethyl-N-(5-(1-piperazinyl)-2-pyridinyl)spiro[cyclohex-2-ene-1,9'-pyrido[4',3':3,4]cyclopenta[1,2-d]pyrimidin]-2'-amine;

4,4-dimethyl-N-(4-(1-piperazinyl)phenyl)spiro[cyclohex-2-ene-1,9'-pyrido[4',3':3,4]cyclopenta[1,2-d]pyrimidin]-2'-amine;

N-(6-(4-(dimethylamino)-1-piperidinyl)-3-pyridinyl)-4,4-dimethylspiro[cyclohex-2-ene-1,9'-pyrido[4',3':3,4]cyclopenta[1,2-d]pyrimidin]-2'-amine;

4,4-dimethyl-N-(6-(4-methyl-1-piperazinyl)-3-pyridinyl)spiro[cyclohex-2-ene-1,9'-pyrido[4',3':3,4]cyclopenta[1,2-d]pyrimidin]-2'-amine;

N-(6-(1-piperazinyl)-3-pyridinyl)spiro[cyclohexane-1,9'-pyrido[4',3':3,4]cyclopenta[1,2-d]pyrimidin]-2'-amine;

N-(4-(1-piperazinylcarbonyl)-1,3-thiazol-2-yl)spiro[cyclohexane-1,9'-pyrido[4',3':3,4]cyclopenta[1,2-d]pyrimidin]-2'-amine;

N-(4-(1-piperazinyl)phenyl)spiro[indeno[2,1-d]pyrimidine-9,4'-piperidin]-2-amine;

N-(4-(1-piperidinyl)phenyl)spiro[indeno[2,1-d]pyrimidine-9,4'-piperidin]-2-amine;

N-(4-(4-morpholinyl)phenyl)spiro[indeno[2,1-d]pyrimidine-9,4'-piperidin]-2-amine;

1'-methyl-N-(4-(4-methyl-1-piperazinyl)phenyl)spiro[indeno[2,1-d]pyrimidine-9,4'-piperidin]-2-amine;

N-(4-(1-piperazinyl)phenyl)-2',3',5',6'-tetrahydrospiro[indeno[2,1-d]pyrimidine-9,4'-pyran]-2-amine;

N-(4-(4-methyl-1-piperazinyl)phenyl)-2',3',5',6'-tetrahydrospiro[indeno[2,1-d]pyrimidine-9,4'-pyran]-2-amine;

N-(3-fluoro-4-(4-methyl-1-piperazinyl)phenyl)-2',3',5',6'-tetrahydrospiro[indeno[2,1-d]pyrimidine-9,4'-pyran]-2-amine;

tert-butyl 4-(4-(spiro[cyclohexane-1,9'-indeno[2,1-d]pyrimidin]-2'-ylamino)phenyl)-1-piperazinecarboxylate;

N-(4-(1-piperazinyl)phenyl)spiro[cyclohexane-1,9'-indeno[2,1-d]pyrimidin]-2'-amine;

N-(5-(1-piperazinyl)-2-pyridinyl)spiro[cyclopentane-1,9'-pyrido[4',3':3,4]cyclopenta[1,2-d]pyrimidin]-2'-amine;

9,9-diethyl-N-(5-(1-piperazinyl)-2-pyridinyl)-9H-pyrido[4',3':3,4]cyclopenta[1,2-d]pyrimidin-2-amine;

N-(5-(1-piperazinyl)-2-pyridinyl)-2,3,5,6-tetrahydrospiro[pyran-4,9'-pyrido[4',3':3,4]cyclopenta[1,2-d]pyrimidin]-2'-amine;

N-(5-(1-piperazinyl)-2-pyridinyl)spiro[cycloheptane-1,9'-pyrido[4',3':3,4]cyclopenta[1,2-d]pyrimidin]-2'-amine;

N-(5-(1-piperazinyl)-2-pyridinyl)spiro[cyclohexane-1,9'-pyrido[4',3':3,4]cyclopenta[1,2-d]pyrimidin]-2'-amine;

(3R)-1-(6-(spiro[cyclohexane-1,9'-pyrido[4',3':3,4]cyclopenta[1,2-d]pyrimidin]-2'-ylamino)-3-pyridazinyl)-3-pyrrolidinol;

4,4-dimethyl-N-(6-(4-(dimethylamino)piperidin-1-yl)-3-pyridinyl)spiro[cyclohex-2-ene-1,9'-pyrido[4',3':3,4]cyclopenta[1,2-d]pyrimidin]-2'-amine;

4,4-dimethyl-N-(6-(4-(dimethylamino)piperidin-1-yl)-pyridazin-3-yl)spiro[cyclohex-2-ene-1,9'-pyrido[4',3':3,4]cyclopenta[1,2-d]pyrimidin]-2'-amine; or 4,4-dimethyl-N-(6-(cis-3,5-dimethylpiperazin-1-yl)pyridin-3-yl)spiro[cyclohex-2-ene-1,9'-pyrido[4',3':3,4]cyclopenta[1,2-d]pyrimidin]-2'-amine.

20. A pharmaceutical composition comprising the compound of claim 1 together with a pharmaceutically acceptable vehicle, adjuvant or diluent.

* * * * *